US008920928B2

(12) United States Patent
He et al.

(10) Patent No.: US 8,920,928 B2
(45) Date of Patent: Dec. 30, 2014

(54) PHOTOCHROMIC COMPOUNDS AND COMPOSITIONS

(75) Inventors: Meng He, Murrysville, PA (US); Darrin R. Dabideen, Pittsburgh, PA (US); Sujit Mondal, Gibsonia, PA (US); Xiao-Man Dai, Export, PA (US); Ruisong Xu, Murrysville, PA (US); Wenjing Xiao, Murrysville, PA (US); Massimiliano Tomasulo, Monroeville, PA (US); Huayun Yu, Monroeville, PA (US); Anu Chopra, Pittsburgh, PA (US); Anil Kumar, Murrysville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 400 days.

(21) Appl. No.: 13/325,285

(22) Filed: Dec. 14, 2011

(65) Prior Publication Data
US 2012/0156508 A1  Jun. 21, 2012

Related U.S. Application Data

(60) Provisional application No. 61/459,634, filed on Dec. 16, 2010.

(51) Int. Cl.
| | |
|---|---|
| G02B 1/04 | (2006.01) |
| G02C 7/02 | (2006.01) |
| G02C 7/10 | (2006.01) |
| G02C 7/14 | (2006.01) |
| C07D 311/92 | (2006.01) |
| C07D 311/94 | (2006.01) |

(52) U.S. Cl.
CPC ............... *C07D 311/94* (2013.01); *G02B 1/04* (2013.01); *G02C 7/102* (2013.01); *C07D 311/92* (2013.01); *G02C 7/02* (2013.01); *G02C 7/14* (2013.01)
USPC ............ 428/411.1; 428/423.1; 428/447; 428/522; 252/586; 549/381; 549/382

(58) Field of Classification Search
None
See application file for complete search history.

(56) References Cited

U.S. PATENT DOCUMENTS

| | | | |
|---|---|---|---|
| 4,556,605 | A | 12/1985 | Mogami et al. |
| 4,931,220 | A | 6/1990 | Haynes et al. |
| 5,645,767 | A | 7/1997 | Van Gemert |
| 5,658,501 | A | 8/1997 | Kumar et al. |
| 5,698,141 | A | 12/1997 | Kumar |
| 5,723,072 | A | 3/1998 | Kumar |
| 5,869,658 | A | 2/1999 | Lin et al. |
| 5,955,520 | A | 9/1999 | Heller et al. |
| 5,961,892 | A | 10/1999 | Gemert et al. |
| 5,962,617 | A | 10/1999 | Slagel |
| 6,022,497 | A | 2/2000 | Kumar |
| 6,025,026 | A | 2/2000 | Smith et al. |
| 6,060,001 | A | 5/2000 | Welch et al. |
| 6,096,375 | A | 8/2000 | Ouderkirk et al. |
| 6,113,814 | A | 9/2000 | Gemert et al. |
| 6,150,430 | A | 11/2000 | Walters et al. |
| 6,153,126 | A | 11/2000 | Kumar |
| 6,187,444 | B1 | 2/2001 | Bowles, III et al. |
| 6,268,055 | B1 | 7/2001 | Walters et al. |
| 6,280,838 | B1 * | 8/2001 | Bernards et al. ............ 428/325 |
| 6,296,785 | B1 | 10/2001 | Nelson et al. |
| 6,432,544 | B1 | 8/2002 | Stewart et al. |
| 6,436,525 | B1 | 8/2002 | Welch et al. |
| 6,506,488 | B1 | 1/2003 | Stewart et al. |
| 6,531,076 | B2 | 3/2003 | Crano et al. |
| 6,555,028 | B2 | 4/2003 | Walters et al. |
| 6,602,603 | B2 | 8/2003 | Welch et al. |
| 6,641,874 | B2 | 11/2003 | Kuntz et al. |
| 6,660,727 | B1 | 12/2003 | Mann et al. |
| 6,683,709 | B2 | 1/2004 | Mann et al. |
| 6,736,998 | B2 | 5/2004 | Petrovskaia et al. |
| 7,008,568 | B2 | 3/2006 | Qin |
| 7,166,357 | B2 | 1/2007 | Kumar et al. |
| 7,256,921 | B2 | 8/2007 | Kumar et al. |
| 7,262,295 | B2 | 8/2007 | Walters et al. |
| 7,320,826 | B2 | 1/2008 | Kumar et al. |
| 7,557,208 | B2 | 7/2009 | Walters et al. |
| 2004/0068071 | A1 | 4/2004 | Hoff et al. |
| 2006/0228557 | A1 | 10/2006 | Kim et al. |
| 2010/0014010 | A1 | 1/2010 | He et al. |
| 2011/0140056 | A1 | 6/2011 | He et al. |
| 2012/0156521 | A1 | 6/2012 | He et al. |

FOREIGN PATENT DOCUMENTS

| | | |
|---|---|---|
| DE | 19741705 A1 | 4/1999 |
| EP | 1731947 A1 | 12/2006 |
| WO | 9614596 A1 | 5/1996 |
| WO | 9748762 A1 | 12/1997 |
| WO | 0119813 A1 | 3/2001 |
| WO | 0170719 A2 | 9/2001 |
| WO | 2004085568 A2 | 10/2004 |

OTHER PUBLICATIONS

Araujo et al., "Photochronnism," Techniques in Chemistry, 1971, pp. 734-853, vol. III, Chapter 3, Glenn H. Brown, Editor, Wiley-Interscience a Division of John Wiley & Sons, Inc.
"Friedel-Crafts and Related Reactions," George A. Olah, Interscience Publishers, 1964, p. 1, vol. 3, Chapter XXXI (Aromatic Ketone Synthesis).
Ishihara et al., "Regioselective Friedel-Crafts Acylation of 1,2,3,4-Tetrahydroquinoline and Related Nitrogen Heterocycles: Effects of NH Protective Groups and Ring Size," J. Chem. Soc. Perkin Trans., 1992, pp. 3401-3406, vol. 1.
Wang et al., "Addition of Grignard Reagents to Aryl Acid Chlorides: An Efficient Synthesis of Aryl Ketones," Organic Letters, 2005, pp. 5593-5595, vol. 7, No. 25.
Hattori et al., "Practical Synthesis of 4'-Methylbiphenyl-2-carboxylic Acid," Synthesis, Jan. 1995, pp. 41-43.
Furrow et al., Practical Procedures for the Preparation of N-tert-Butyldimethylsilylhydrazones and Their Use in Modified Wolff-Kishner Reductions and in the Synthesis of Vinyl Halides and gem-Dihalides, J. Am. Chem. Soc., 2004, pp. 5436-5445, vol. 126, No. 17.
Hattori et al., "Facile Construction of the 1-Phenylnaphthyl Skeleton via an Ester-mediated Nucleophilic Aromatic Substitution Reaction. Applications to the Synthesis of Phenylnaphthalide Lignans," J. Chem. Soc. Perkin Trans., 1995, pp. 235-241, vol. 1.

* cited by examiner

*Primary Examiner* — Ramsey Zacharia
(74) *Attorney, Agent, or Firm* — The Webb Law Firm

(57) ABSTRACT

Described herein are compounds generally comprising an indeno[2',3':3,4]naptho[1,2-b]pyran structure. Such compounds may be useful for their photochromic properties, and be used in certain photochromic compositions. Such compositions may further comprise other photochromic compositions and/or materials. Additionally, such compounds and/or compositions may be suitable for preparing certain photochromic articles.

26 Claims, No Drawings

PHOTOCHROMIC COMPOUNDS AND COMPOSITIONS

CROSS REFERENCE TO RELATED APPLICATIONS

This application claims the benefit of priority of U.S. Provisional Patent Application No. 61/459,634, filed Dec. 16, 2010, all of which document is hereby incorporated herein by reference.

BACKGROUND

The present invention relates generally to photochromic compounds and to devices and elements made using the photochromic compounds disclosed herein.

Conventional photochromic compounds have at least two states, a first state having a first absorption spectrum and a second state having a second absorption spectrum that differs from the first absorption spectrum, and are capable of switching between the two states in response to at least actinic radiation. Further, conventional photochromic compounds can be thermally reversible. That is, conventional photochromic compounds are capable of switching between a first state and a second state in response to at least actinic radiation and reverting back to the first state in response to thermal energy. As used herein "actinic radiation" means electromagnetic radiation, such as but not limited to ultraviolet and visible radiation that is capable of causing a response. More specifically, conventional photochromic compounds can undergo a transformation in response to actinic radiation from one isomer to another, with each isomer having a characteristic absorption spectrum, and can further revert back to the first isomer in response to thermal energy (i.e., be thermally reversible). For example, conventional thermally reversible photochromic compounds are generally capable of switching from a first state, for example a "clear state," to a second state, for example a "colored state," in response to actinic radiation and reverting back to the "clear" state in response to thermal energy.

It would be advantageous to provide photochromic compounds, such as but not limited to thermally reversible photochromic compounds, that can exhibit useful photochromic properties in at least one state, and that can be used in a variety of applications to impart photochromic properties.

BRIEF SUMMARY OF THE DISCLOSURE

Described herein are compounds represented by the following graphic Formula

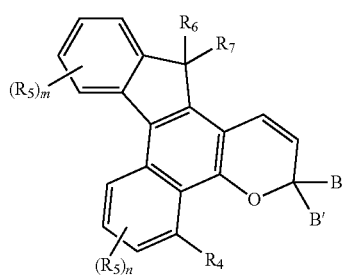

Formula III wherein
R$_4$ is selected from hydroxy, halogen, optionally substituted alkyl, optionally substituted alkenyl, optionally substituted alkynyl, optionally substituted aryl, optionally substituted heteroaryl, optionally substituted alkoxy, cyano, nitro, alkoxycarbonyl, aminocarbonyl, carboxy, optionally substituted amino, carbamidyl, ureido, thioureido, silyl, —SH, siloxy, sulfanyl, and azido;
R$_5$ for each occurrence, is independently selected from chiral or achiral groups selected from formyl, alkylcarbonyl, alkoxycarbonyl, aminocarbonyl, arylcarbonyl, aryloxycarbonyl, aminocarbonyloxy, alkoxycarbonylamino, aryloxycarbonylamino, boronic acid, boronic acid esters, cycloalkoxycarbonylamino, heterocycloalkyloxycarbonylamino, heteroaryloxycarbonylamino, optionally substituted alkyl, optionally substituted alkenyl, optionally substituted alkynyl, halogen, optionally substituted cycloalkyl, optionally substituted aryl, optionally substituted heteroaryl, optionally substituted alkoxy, optionally substituted heteroalkyl, optionally substituted heterocycloalkyl, and optionally substituted amino;
m is an integer from 0 to 4;
n is an integer from 0 to 3;
R$_6$ and R$_7$ are each independently selected from hydrogen, hydroxy and chiral or achiral groups selected from optionally substituted heteroalkyl, optionally substituted alkyl, optionally substituted alkenyl, optionally substituted alkynyl, optionally substituted aryl, optionally substituted heteroaryl, optionally substituted cycloalkyl, optionally substituted heterocycloalkyl, halogen, optionally substituted amino, carboxy, alkylcarbonyl, alkoxycarbonyl, optionally substituted alkoxy, and aminocarbonyl, or R$_1$ and R$_2$ may be taken together with any intervening atoms to form a group selected from oxo, optionally substituted cycloalkyl, and optionally substituted heterocycloalkyl; and
B and B' are each independently selected from hydrogen, halogen, and chiral or achiral groups selected from metallocenyl, optionally substituted alkyl, optionally substituted alkenyl, optionally substituted alkynyl, optionally substituted heteroalkyl, optionally substituted alkoxy, optionally substituted aryl, optionally substituted heteroaryl, optionally substituted heterocycloalkyl, and optionally substituted cycloalkyl, or wherein B and B' are taken together with any intervening atoms to form a group selected from optionally substituted cycloalkyl and optionally substituted heterocycloalkyl.

Also provided herein are photochromic compositions and photochromic articles comprising at least one compound of Formula II as described above.

DETAILED DESCRIPTION

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

"Alkyl" by itself or as part of another substituent refers to a saturated or unsaturated, branched, or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop- 1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group comprises from 1 to 20 carbon atoms, in certain embodiments, from 1 to 10 carbon atoms, in certain embodiments, from 1 to 8 or 1 to 6 carbon atoms, and in certain embodiments from 1 to 3 carbon atoms.

"Acyl" by itself or as part of another substituent refers to a radical —C(O)$R^{30}$, where $R^{30}$ is hydrogen, alkyl, heteroalkyl, cycloalkyl, heterocycloalkyl, cycloalkylalkyl, heterocycloalkylalkyl, aryl, heteroaryl, arylalkyl, or heteroarylalkyl, which can be substituted, as defined herein. Examples of acyl groups include, but are not limited to, formyl, acetyl, cyclohexylcarbonyl, cyclohexylmethylcarbonyl, benzoyl, benzylcarbonyl, and the like.

"Alkoxy" by itself or as part of another substituent refers to a radical —O$R^{31}$ where $R^{31}$ is alkyl, cycloalkyl, cycloalkylalkyl, aryl, or arylalkyl, which can be substituted, as defined herein. In some embodiments, alkoxy groups have from 1 to 18 carbon atoms. Examples of alkoxy groups include, but are not limited to, methoxy, ethoxy, propoxy, butoxy, cyclohexyloxy, and the like.

"Alkoxycarbonyl" by itself or as part of another substituent refers to a radical —C(O)O$R^{31}$ where $R^{31}$ is alkyl, cycloalkyl, cycloalkylalkyl, aryl, or arylalkyl, which can be substituted, as defined herein.

"Amino" refers to the radical —$NH_2$.

"Aminocarbonyl" by itself or as part of another substituent refers to radical of the formula —NC(O)$R^{60}$ where each $R^{60}$ is selected from hydrogen, alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl "Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl, or alkynyl moiety of the arylalkyl group is $C_{1-10}$ and the aryl moiety is $C_{6-20}$, and in certain embodiments, an arylalkyl group is $C_{7-20}$ arylalkyl, e.g., the alkanyl, alkenyl, or alkynyl moiety of the arylalkyl group is $C_{1-8}$ and the aryl moiety is $C_{6-12}$.

"Carboxamidyl" by itself or as part of another substituent refers to a radical of the formula —C(O)N$R^{60}R^{61}$ where each $R^{60}$ and $R^{61}$ are independently hydrogen, alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or $R^{60}$ and $R^{61}$ together with the nitrogen atom to which they are bonded form a heterocycloalkyl, substituted heterocycloalkyl, heteroaryl, or substituted heteroaryl ring.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, and in certain embodiments, $C_{3-12}$ cycloalkyl or $C_{5-12}$ cycloalkyl.

"Cycloalkylalkyl" by itself or as part of another substituent refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{7-30}$ cycloalkylalkyl, e.g., the alkanyl, alkenyl, or alkynyl moiety of the cycloalkylalkyl group is $C_{1-10}$ and the cycloalkyl moiety is $C_{6-20}$, and in certain embodiments, a cycloalkylalkyl group is $C_{7-20}$ cycloalkylalkyl, e.g., the alkanyl, alkenyl, or alkynyl moiety of the cycloalkylalkyl group is $C_{1-8}$ and the cycloalkyl moiety is $C_{4-20}$ or $C_{6-12}$.

"Halogen" refers to a fluoro, chloro, bromo, or iodo group.

"Heteroalkyl" by itself or as part of another substituent refer to an alkyl group in which one or more of the carbon atoms (and any associated hydrogen atoms) are independently replaced with the same or different heteroatomic groups. In some embodiments, heteroalkyl groups have from 1 to 8 carbon atoms. Examples of heteroatomic groups include, but are not limited to, —O—, —S—, —S—S—, —NR$^{38}$, =N—N=, —N=N—, —N=N—NR$^{39}$R$^{40}$, —PR$^{41}$—, —P(O)$_2$—, —POR$^{42}$—, —O—P(O)$_2$—, —SO—, —SO$_2$—, —SnR$^{43}$R$^{44}$— and the like, where R$^{38}$, R$^{39}$, R$^{40}$, R$^{41}$, R$^{42}$, R$^{43}$, and R$^{44}$ are independently hydrogen, alkyl, substituted alkyl, aryl, substituted aryl, arylalkyl, substituted arylalkyl, cycloalkyl, substituted cycloalkyl, heterocycloalkyl, substituted heterocycloalkyl, heteroalkyl, substituted heteroalkyl, heteroaryl, substituted heteroaryl, heteroarylalkyl, or substituted heteroarylalkyl. Where a specific level of saturation is intended, the nomenclature "heteroalkanyl," "heteroalkenyl," or "heteroalkynyl" is used. In certain embodiments, R$^{38}$, R$^{39}$, R$^{40}$, R$^{41}$, R$^{42}$, R$^{43}$, and R$^{44}$ are independently chosen from hydrogen and C$_{1-3}$ alkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which can be aromatic or non-aromatic in which at least one ring atom is a heteroatom. Heteroaryl encompasses 5- to 12-membered aromatic, such as 5- to 7-membered, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl, or heteroarylalkynyl is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like.

"Heterocycloalkylalkyl" by itself or as part of another substituent refers to an acyclic alkyl radical in which one of the hydrogen atoms bonded to a carbon atom, typically a terminal or sp$^3$ carbon atom, is replaced with a heterocycloalkyl group. Where specific alkyl moieties are intended, the nomenclature heterocycloalkylalkanyl, heterocycloalkylalkenyl, or heterocycloalkylalkynyl is used. In certain embodiments, a heterocycloalkylalkyl group is a 6- to 30-membered heterocycloalkylalkyl, e.g., the alkanyl, alkenyl, or alkynyl moiety of the heterocycloalkylalkyl is 1- to 10-membered and the heterocycloalkyl moiety is a 5- to 20-membered heterocycloalkyl, and in certain embodiments, 6- to 20-membered heterocycloalkylalkyl, e.g., the alkanyl, alkenyl, or alkynyl moiety of the heterocycloalkylalkyl is 1- to 8-membered and the heterocycloalkyl moiety is a 5- to 12-membered heterocycloalkyl.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one, or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Perhaloalkyl" is a subset of substituted alkyl wherein each hydrogen atom is replaced with the same or different halogen atom. Examples of perhaloalkyl includes, but is not limited to, —$CF_3$, —$CF_2CF_3$, and —$C(CF_3)_3$.

"Perhaloalkoxy" is a subset of substituted alkoxy wherein each hydrogen atom of $R^{31}$ is replaced with the same or different halogen atom. Examples of perhaloalkoxy includes, but is not limited to, —$OCF_3$, —$OCF_2CF_3$, and —$OC(CF_3)_3$.

"Protecting group" refers to a grouping of atoms, which when attached to a reactive group in a molecule masks, reduces, or prevents that reactivity. Examples of protecting groups can be found in Wuts and Greene, "Protective Groups in Organic Synthesis," John Wiley & Sons, 4th ed. 2006; Harrison et al., "Compendium of Organic Synthetic Methods," Vols. 1-11, John Wiley & Sons 1971-2003; Larock "Comprehensive Organic Transformations," John Wiley & Sons, 2nd ed. 2000; and Paquette, "Encyclopedia of Reagents for Organic Synthesis," John Wiley & Sons, 11th ed. 2003. Examples of amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Examples of hydroxy protecting groups include, but are not limited to, those in which the hydroxy group is either acylated or alkylated such as benzyl, and trityl ethers as well as alkyl ethers, tetrahydropyranyl ethers, trialkylsilyl ethers, and allyl ethers.

"Silyl" by itself or as part of another substituent refers to a radical of the formula —$SiR^{30}R^{31}R^{31}$ where each of $R^{30}$, $R^{31}$, and $R^{31}$ is independently selected from alkyl, alkoxyl, and phenyl, which can each be substituted, as defined herein.

"Siloxy" by itself or as part of another substituent refers to a radical of the formula —$OSiR^{30}R^{31}R^{31}$ where each of $R^{30}$, $R^{31}$, and $R^{31}$ is independently selected from alkyl, alkoxyl, and phenyl, which can each be substituted, as defined herein.

"Substituted" refers to a group in which one or more hydrogen atoms are independently replaced with the same or different substituent(s). Examples of substituents include, but are not limited to, —$R^{64}$, —$R^{60}$, —$O^-$, (—OH), =O, —$OR^{60}$, —$SR^{60}$, —$S^-$, =S, —$NR^{60}R^{61}$, =$NR^{60}$, —$CX_3$, —CN, —$CF_3$, —OCN, —SCN, —NO, —$NO_2$, =$N_2$, —$N_3$, —$S(O)_2O^-$, —$S(O)_2OH$, —$S(O)_2R^{60}$, —$OS(O_2)O^-$, —$OS(O)_2R^{60}$, —$P(O)(O^-)_2$, —$P(O)(OR^{60})(O)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$, —$C(NR^{62})NR^{60}R^{61}$, —$S(O)_2$, $NR^{60}R^{61}$, —$NR^{63}S(O)_2R^{60}$, —$NR^{63}C(O)R^{60}$, and —$S(O)R^{60}$ where each —$R^{64}$ is independently a halogen; each $R^{60}$ and $R^{61}$ are independently hydrogen, alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or $R^{60}$ and $R^{61}$ together with the nitrogen atom to which they are bonded form a heterocycloalkyl, substituted heterocycloalkyl, heteroaryl, or substituted heteroaryl ring, and $R^{62}$ and $R^{63}$ are independently hydrogen, alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl, or substituted heteroarylalkyl, or $R^{62}$ and $R^{63}$ together with the atom to which they are bonded form one or more heterocycloalkyl, substituted heterocycloalkyl, heteroaryl, or substituted heteroaryl rings. In certain embodiments, a tertiary amine or aromatic nitrogen may be substituted with one or more oxygen atoms to form the corresponding nitrogen oxide.

"Sulfonate" by itself or as part of another substituent refers to a sulfur radical of the formula —$S(O)_2O^-$.

"Sulfonyl" by itself or as part of another substituent refers to a sulfur radical of the formula —$S(O)_2R^{60}$ where $R^{60}$ may be selected from hydrogen, alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, and substituted heteroarylalkyl.

In certain embodiments, substituted aryl and substituted heteroaryl include one or more of the following substitute groups: F, Cl, Br, $C_{1-3}$ alkyl, substituted alkyl, $C_{1-3}$ alkoxy, —$S(O)_2NR^{50}R^{51}$, —$NR^{50}R^{51}$, —$CF_3$, —$OCF_3$, —CN, —$NR^{50}S(O)_2R^{51}$, —$NR^{50}C(O)R^{51}$, $C_{5-10}$ aryl, substituted $C_{5-10}$ aryl, $C_{5-10}$ heteroaryl, substituted $C_{5-10}$ heteroaryl, —$C(O)OR^{50}$, —$NO_2$, —$C(O)R^{50}$, —$C(O)NR^{50}R^{51}$, —$OCHF_2$, $C_{1-3}$ acyl, —$SR^{50}$, —$S(O)_2OH$, —$S(O)_2R^{50}$, —$S(O)R^{50}$, —$C(S)R^{50}$, —$C(O)O^-$, —$C(S)OR^{50}$, —$NR^{50}C(O)NR^{51}R^{52}$, —$NR^{50}C(S)NR^{51}R^{52}$, and —$C(NR^{50})NR^{51}R^{52}$, $C_{3-8}$ cycloalkyl, and substituted $C_{3-8}$ cycloalkyl, wherein $R^{50}$, $R^{51}$, and $R^{52}$ are each independently selected from hydrogen and $C_1$-$C_4$ alkyl.

As used in this specification and the appended claims, the articles "a," "an," and "the" include plural referents unless expressly and unequivocally limited to one referent.

Unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

All numerical ranges herein include all numerical values and ranges of all numerical values within the recited range of numerical values. Further, while the numerical ranges and parameters setting forth the broad scope of the disclosure are approximations as discussed above, the numerical values set forth in the Examples section are reported as precisely as possible. It should be understood, however, that such numerical values inherently contain certain errors resulting from the measurement equipment and/or measurement technique.

The phrase "an at least partial coating" means an amount of coating covering from a portion to the complete surface of the substrate. The phrase "an at least partially cured coating" refers to a coating in which the curable or crosslinkable components are at least partially cured, crosslinked and/or reacted. In alternate non-limiting embodiments, the degree of reacted components, can vary widely, e.g., from 5% to 100% of all the possible curable, crosslinkable and/or reactable components.

The phrase "an at least partially abrasion resistant coating or film" refers to a coating or film that demonstrates a Bayer Abrasion Resistance Index of from at least 1.3 to 10.0 in ASTM F-735 Standard Test Method for Abrasion Resistance of Transparent Plastics and Coatings Using the Oscillating Sand Method. The phrase "an at least partially antireflective coating" is a coating that at least partially improves the antireflective nature of the surface to which it is applied by increasing the percent transmittance as compared to an uncoated surface. The improvement in percent transmittance can range from 1 to 9 percent above the untreated surface. Put another way, the percent transmittance of the treated surface can range from a percentage greater than the untreated surface up to 99.9.

As previously discussed, conventional thermally reversible photochromic compounds are adapted to switch from a first state to a second state in response to actinic radiation, and to revert back to the first state in response to thermal energy. More specifically, conventional thermally reversible, photochromic compounds are capable of transforming from one isomeric form (for example and without limitation, a closed form) to another isomeric form (for example and without limitation, an open form) in response to actinic radiation, and reverting back to the closed form when exposed to thermal energy. As previously mentioned, the present invention is directed to a compound of Formula III:

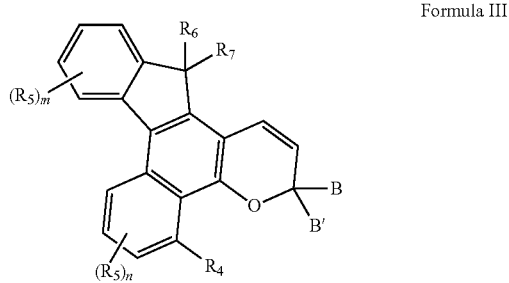

Formula III

With reference to Formula III above, $R_4$ is selected from hydroxy, halogen, optionally substituted alkyl, optionally substituted alkenyl, optionally substituted alkynyl, optionally substituted aryl, optionally substituted heteroaryl, optionally substituted alkoxy, cyano, nitro, alkoxycarbonyl, aminocarbonyl, carboxy, optionally substituted amino, carbamidyl, ureido, thioureido, silyl, —SH, siloxy, sulfanyl, and azido. Typically, $R_4$ is selected from chloro, fluoro, bromo, methyl, ethyl, phenyl, perfluoroalkoxy, and perfluoroalkyl. In a particular embodiment, $R_4$ is selected from chloro, fluoro, bromo, and trifluoromethyl.

Also, $R_5$ for each occurrence, is independently selected from chiral or achiral groups selected from formyl, alkylcarbonyl, alkoxycarbonyl, aminocarbonyl, arylcarbonyl, aryloxycarbonyl, aminocarbonyloxy, alkoxycarbonylamino, aryloxycarbonylamino, boronic acid, boronic acid esters, cycloalkoxycarbonylamino, heterocycloalkyloxycarbonylamino, heteroaryloxycarbonylamino, optionally substituted alkyl, optionally substituted alkenyl, optionally substituted alkynyl, halogen, optionally substituted cycloalkyl, optionally substituted aryl, optionally substituted heteroaryl, optionally substituted alkoxy, optionally substituted heteroalkyl, optionally substituted heterocycloalkyl, and optionally substituted amino. Typically, $R_5$ for each occurrence, is independently selected from alkylcarbonyl, alkoxycarbonyl, aminocarbonyl, optionally substituted alkyl, boronic acid ester, halogen, optionally substituted cycloalkyl, optionally substituted aryl, optionally substituted alkoxy, optionally substituted heterocycloalkyl, and optionally substituted amino. In a particular embodiment of the present invention, $R_5$ for each occurrence is independently selected from methyl, ethyl, bromo, chloro, fluoro, methoxy, ethoxy and $CF_3$.

Further, with reference to Formula III, m is an integer from 0 to 4, such as from 0 to 3, or from 0 to 2; and n is an integer from 0 to 3, such as from 0 to 2.

Additionally with reference to Formula III, $R_6$ and $R_7$ are each independently selected from hydrogen, hydroxy and chiral or achiral groups selected from optionally substituted heteroalkyl, optionally substituted alkyl, optionally substituted alkenyl, optionally substituted alkynyl, optionally substituted aryl, optionally substituted heteroaryl, optionally substituted cycloalkyl, optionally substituted heterocycloalkyl, halogen, optionally substituted amino, carboxy, alkylcarbonyl, alkoxycarbonyl, optionally substituted alkoxy, and aminocarbonyl, or $R_1$ and $R_2$ may be taken together with any intervening atoms to form a group selected from oxo, optionally substituted cycloalkyl, and optionally substituted heterocycloalkyl. Typically, $R_6$ and $R_7$ are each independently selected from hydrogen, hydroxy, and chiral groups selected from optionally substituted heteroalkyl, optionally substituted alkyl, optionally substituted aryl, optionally substituted cycloalkyl, halogen, carboxy, alkylcarbonyl, alkoxycarbonyl, optionally substituted alkoxy, and aminocarbonyl or $R_1$ and $R_2$ may be taken together with any intervening atoms to form a group selected from oxo and optionally substituted cycloalkyl. In a particular embodiment of the present invention, $R_6$ and $R_7$ are each independently selected from methyl, ethyl, propyl and butyl.

Substitutents B and B' of Formula III are each independently selected from hydrogen, halogen, and chiral or achiral groups selected from metallocenyl, optionally substituted alkyl, optionally substituted alkenyl, optionally substituted alkynyl, optionally substituted heteroalkyl, optionally substituted alkoxy, optionally substituted aryl, optionally substituted heteroaryl, optionally substituted heterocycloalkyl, and optionally substituted cycloalkyl, or B and B' are taken together with any intervening atoms to form a group selected from optionally substituted cycloalkyl and optionally substituted heterocycloalkyl. Typically, B and B' are each independently selected from hydrogen, chiral groups selected from optionally substituted alkyl, optionally substituted alkenyl, optionally substituted aryl, optionally substituted heteroaryl, and optionally substituted cycloalkyl, or B and B' are taken together with any intervening atoms to form a group selected from optionally substituted cycloalkyl. In a particular embodiment of the present invention, B and B' are each independently selected from phenyl substituted with one or more groups independently selected from aryl, heteroaryl, heterocycloalkyl, alkyl, alkenyl, alkynyl, alkoxy, halogen, amino, alkylcarbonyl, carboxy, and alkoxycarbonyl.

Specific examples of the compound of the present invention can include, but are not limited to those be selected from:
3,3-bis(4-methoxyphenyl)-5,7-dibromo-13,13-dimethyl-3H,13H-indeno[2',3':3,4]naphtho[1,2-b]pyran;
3,3-bis(4-methoxyphenyl)-5,7-dichloro-13,13-dimethyl-3H,13H-indeno[2',3':3,4]naphtho[1,2-b]pyran;
3-(4-butoxyphenyl)-3-(4-methoxyphenyl)-5,7-dibromo-11-trifluoromethyl-13,13-dimethyl-3H,13H-indeno[2',3':3,4[naphtho]1,2-b]pyran;
3-(4-fluorophenyl)-3-(4-(N-piperidinyl)phenyl) 5,7-difluoro-10,12-dibromo-13,13-dimethyl-3H,13H-indeno[2',3':3,4]naphtho[1,2-b]pyran;
3,3-bis(4-methoxyphenyl)-5-chloro-6-methoxy-7-hydroxy-10,12-di(trifluoromethyl)-13,13-dimethyl-3H,13H-indeno[2',3':3,4]naphtho[1,2-b]pyran;

3-(4-butoxyphenyl)-3-phenyl-5-chloro-6-methoxy-7-hydroxy-10,12-di(trifluoromethyl)-13,13-dimethyl-3H,13H-indeno[2',3':3,4]naphtho[1,2-b]pyran;

3,3-bis(4-butoxyphenyl)-5-chloro-6-methoxy-7-hydroxy-10,12-di(trifluoromethyl)-13,13-dimethyl-3H,13H-indeno[2',3':3,4]naphtho[1,2-b]pyran;

3,3-bis(4-fluorophenyl)-5,7-di(trifluoromethyl)-12-bromo-13,13-dimethyl-3H,13H-indeno[2',3':3,4]naphtho[1,2-b]pyran;

3,3-bis(4-fluorophenyl)-5,7-di(trifluoromethyl)-10-bromo-13,13-dimethyl-3H,13H-indeno[2',3':3,4]naphtho[1,2-b]pyran 3-phenyl-3-(4-morpholinophenyl)-5,6,7-trimethoxy-13,13-dimethyl-3H,13H-indeno[2,1-f]naphtho[1,2-b]pyran;

3-phenyl-3-(4-morpholinophenyl)-5,6,7-trimethoxy-10,12-di(trifluoromethyl)-13,13-dimethyl-3H,13H-indeno[2,1-f]naphtho[1,2-b]pyran;

3-(4-methoxyphenyl)-3-(4-morpholinophenyl)-5-methoxy-11-phenyl-13,13-dimethyl-3H,13H-indeno[2,1-f]naphtho[1,2-b]pyran;

3,3-bis-(4-methoxyphenyl)-5-methoxy-11-phenyl-13,13-dimethyl-3H,13H-indeno[2',3':3,4]naphtho[1,2-b]pyran;

3-(4-methoxyphenyl)-3-(4-morpholinophenyl)-5,6,7-trimethoxy-10,12-di(fluoro)-13,13-dimethyl-3H,13H-indeno[2,1-f]naphtho[1,2-b]pyran;

3-(4-methoxyphenyl)-3-(4-morpholinophenyl)-5,6,7-trimethoxy-11-phenyl-13,13-diethyl-3H,13H-indeno[2,1-f]naphtho[1,2-b]pyran;

3-(4-fluorophenyl)-3-phenyl-5,7-difluoro-11-methoxy-13,13-dimethyl-3H,13H-indeno[2',3':3,4]naphtho[1,2-b]pyran;

3-(4-methoxyphenyl)-3-phenyl-5,7-difluoro-11-methoxy-13,13-dimethyl-3H,13H-indeno[2',3':3,4]naphtho[1,2-b]pyran;

3-(4-butoxyphenyl)-3-(4-methoxyphenyl)-5,7-difluoro-11-methoxy-13,13-dimethyl-3H,13H-indeno[2',3':3,4]naphtho[1,2-b]pyran;

3-phenyl-3-(4-methoxyphenyl)-5-methoxy-7-fluoro-11-methoxy-13,13-dimethyl-3H,13H-indeno[2',3':3,4]naphtho[1,2-b]pyran;

3-phenyl-3-(4-methoxyphenyl)-5,7-dimorpholino-11-methoxy 13,13-dimethyl-3H,13H-indeno[2',3':3,4]naphtho[1,2-b]pyran;

3-phenyl-3-(4-methoxyphenyl)-5-morpholino-7-fluoro-11-methoxy-13,13-dimethyl-3H,13H-indeno[2',3':3,4]naphtho[1,2-b]pyran;

3-(4-butoxyphenyl)-3-(4-methoxyphenyl)-5-methoxy-7-fluoro-11-methoxy-13,13-dimethyl-3H,13H-indeno[2',3':3,4]naphtho[1,2-b]pyran;

3-(4-butoxyphenyl)-3-(4-methoxyphenyl)-5,7-difluoro-11-hydroxy-13,13-dimethyl-3H,13H-indeno[2',3':3,4]naphtho[1,2-b]pyran;

3-(4-butoxyphenyl)-3-(4-methoxyphenyl)-5-methoxy-7-fluoro-11-(5-methylthiophen-2-yl)-13,13-dimethyl-3H,13H-indeno[2',3':3,4]naphtho[1,2-b]pyran;

3-phenyl-3-(4-methoxyphenyl)-5,7-difluoro-11-hydroxy-13,13-dimethyl-3H,13H-indeno[2',3':3,4]naphtho[1,2-b]pyran; and 3-phenyl-3-(4-methoxyphenyl)-5,7-difluoro-11-phenyl-13,13-dimethyl-3H,13H-indeno[2',3':3,4]naphtho[1,2-b]pyran.

Any of the previously described compounds may be useful alone, as mixtures, or in combination with other compounds, compositions, and/or materials.

Methods for obtaining the novel compounds described herein will be apparent to those of ordinary skill in the art, suitable procedures being described, for example, in the reaction schemes and examples below, and in the references cited herein.

In the schemes and examples below, the following abbreviations have the following meanings. If an abbreviation is not defined, it has its generally accepted meaning.

Bi(OtF)$_3$=bismuth triflate
DHP=3,4-dihydro-2H-pyran
DCM=dichloromethane
DBSA=dodecylbenzehesulfonic acid
DMF=N,N-dimethylformamide
DMSO=dimethylsulfoxide
EtMgBr=ethyl magnesium bromide
Et$_2$O=diethylether
g=gram
h=hour
HPLC=high-performance liquid chromatography
(iPr)$_2$NH=diisopropyl amine
HOAc=acetic acid
LDA=lithium diisopropylamide
M=molar (molarity)
MeLi=methyl lithium
mg=milligram
min=minutes
mL=milliliter
mmol=millimoles
mM=millimolar
NatOBu=sodium tert-butoxide
N=normal (normality)
ng=nanogram
nm=nanometer
nM=nanomolar
NMP=N-methylpyrrolidone
NMR=nuclear magnetic resonance
PPTS=pyridine p-toluenesulfonate
pTSA=p-toluenesulfohic acid
THF=tetrahyrdofuran
TLC=thin layer chromatography
t-BuOH=t-butanol
(Tf)$_2$O=trifluoromethanesulfonic acid anhydride
μL=microliter
μM=micromolar As discussed in the schemes outlined further below, compound 105 represents one intermediate that may serve as the basis for preparing the photochromic dichroic dyes described herein. For example, it can be prepared as shown in Scheme 1, 2, 3, 4 and 5. Once prepared, the hydroxy functionality of compound 105 can be used for pyran formation as observed in Scheme 6.

Scheme 1

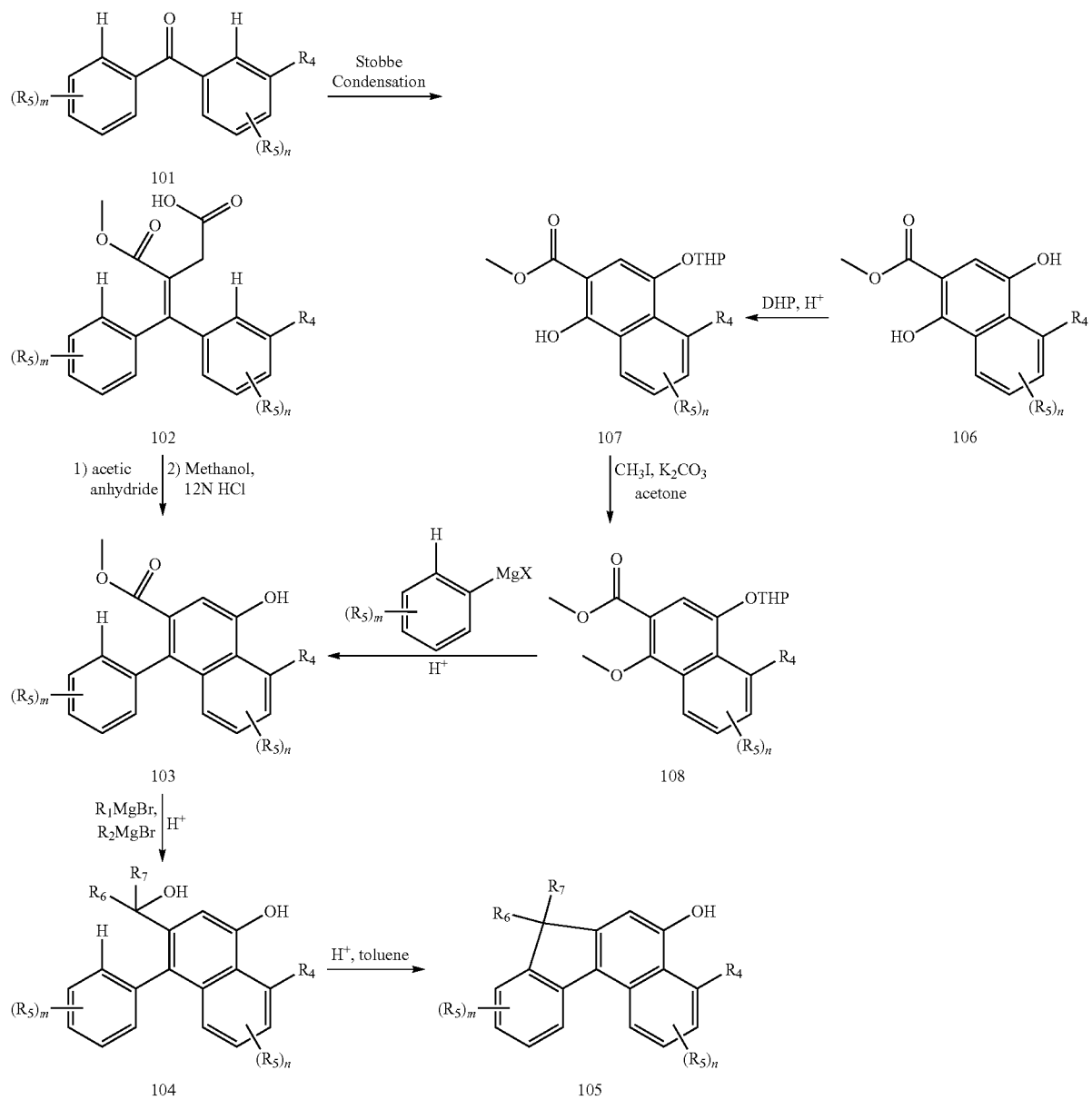

Scheme 1 shows one way of preparing compound 105. $R_6$ and $R_7$ may be selected from optionally substituted chiral or achiral groups such as heteroalkyl, alkyl, perfluoroalkyl, alkenyl, alkynyl, aryl, heteroaryl, cycloalkyl, and heterocycloalkyl.

The aryl ketone 101 can either be purchased or prepared by Friedel-Crafts methods or Grignard or Cuperate methods known in the art. For example, see the publication *Friedel-Crafts and Related Reactions*, George A. Olah, Interscience Publishers, 1964, Vol. 3, Chapter XXXI (Aromatic Ketone Synthesis); "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992; "Addition of Grignard Reagents to Aryl Acid Chlorides: An efficient synthesis of aryl ketones" by Wang, Xiao-jun et al, Organic Letters, Vol. 7, No. 25, 5593-5595, 2005, and references cited therein, which disclosures related to the aforementioned synthetic methods are incorporated herein by reference in their entireties. A Stobbe reaction of aryl ketone 101 with dimethyl succinate in the presence of potassium t-butoxide provides the condensed product of compound 102, which undergoes a ring closure reaction in acetic anhydride followed by methanolysis to form the product of compound 103.

Compound 103 can also be prepared from an ester-mediated nucleophilic aromatic substitution reaction starting from compound 106 by methods known to those skilled in the art, for example, as further described in Synthesis, January 1995, pages 41-43; The Journal of Chemistry Society Perkin Transaction 1, 1995, pages 235-241 and U.S. Pat. No. 7,557,208 B2, which disclosures related to such synthetic methods are incorporated herein by reference in their entireties.

Once prepared, compound 103 can be further converted to indeno-fused product of compound 105 with various substitutions on the bridge carbon via various multistep reactions that can be found in U.S. Pat. Nos. 5,645,767; 5,869,658; 5,698,141; 5,723,072; 5,961,892; 6,113,814; 5,955,520; 6,555,028; 6,296,785; 6,555,028; 6,683,709; 6,660,727; 6,736,998; 7,008,568; 7,166,357; 7,262,295; 7,320,826 and 7,557,208, which disclosures related to the substituents on the bridge carbon are incorporated herein by reference in their entireties. What is shown in Scheme 1 illustrates that compound 103 reacts with Grignard reagent followed by a ring closure reaction to provide compound 105.

obtained. The carbonyl of compound 202 can react with a nucleophile, like Grignard reagent, Organo lithium reagent, or perfluoalkyl trimethylsilane to form compound 203. $R_6$ may be selected from optionally substituted chiral or achiral groups such as heteroalkyl, alkyl, perfluoroalkyl, alkenyl, alkynyl, aryl, heteroaryl, cycloalkyl and heterocycloalkyl. The hydroxyl group of compound 203 can be easily converted into $R_7$, which may be selected from halogen and optionally substituted chiral or achiral groups such as alkoxy, silanoxy, heteroaryloxy and aryloxy.

Scheme 2

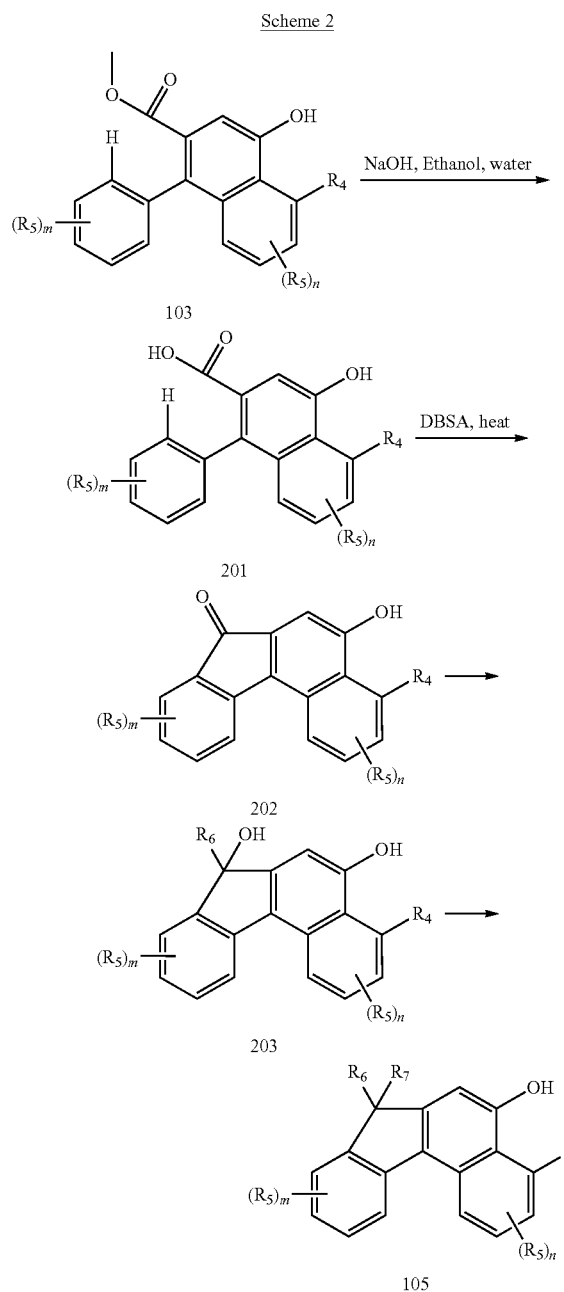

Scheme 3

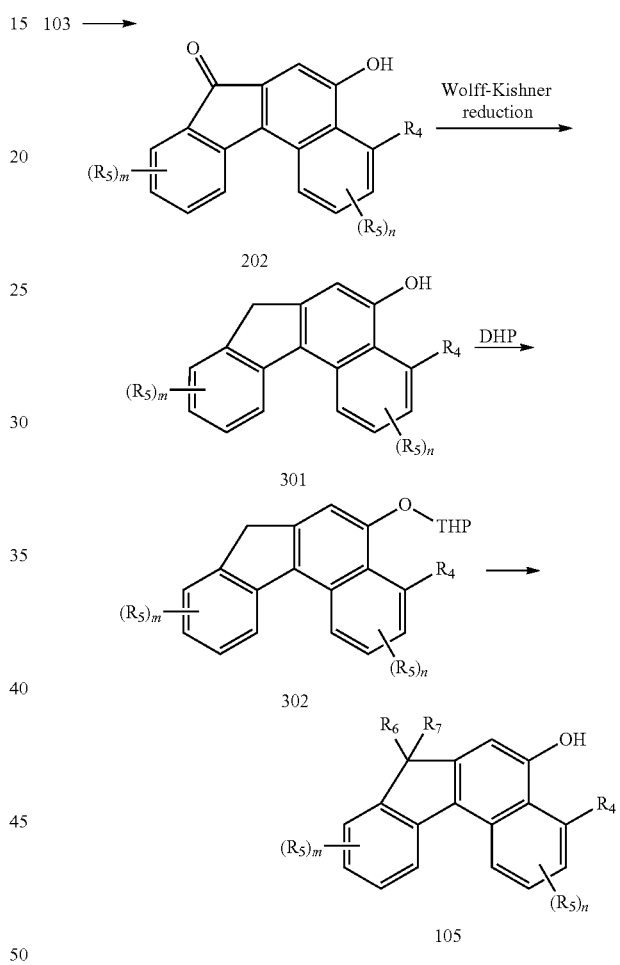

Scheme 2 illustrates a second way of converting compound 103 to compound 105. After hydrolysis of compound 103 followed by a ring closure reaction, compound 202 was Scheme 3 illustrates a third way of converting compound 103 to compound 105. Compound 202 from Scheme 2 can be reduced to 301 using a Wolff-Kishner reduction or its modified version. Examples can be found in "Practical procedures for the preparation of N-tert-butyldimethylsilylhydrozones and their use in modified Wolff-Kishner reductions and in the synthesis of vinyl halides and gem-dihalides" by Myers, Andrew. G. et al, 126, 5436-5445, 2004 and references therein, which disclosures related to the Wolff-Kishner reduction are incorporated herein by reference. After hydroxy protection, compound 302 has a very nucleophilic gem-carbon once deprotonated by base like LDA or methyl Grignard reagent. By those skilled in the art, the deprotonated compound 302 can be converted to $R_6$ and $R_7$ by reacting it with electrophiles such as alkyl halides, carbon dioxide, acid chlorides, nitriles and chloroformate derivatives. As a result, compound 105 can be prepared with $R_6$ and $R_7$ selected from hydrogen, optionally substituted chiral or achiral groups selected from heteroalkyl, alkyl, cycloalkyl, carboxy, alkylcarbonyl, alkoxycarbonyl, alkylcarbonyl, alkoxycarbonyl, aminocarbonyl, arylcarbonyl, aryloxycarbonyl, or $R_6$ and $R_7$ may be taken together with any intervening atoms to form a group selected from oxo, optionally substituted cycloalkyl, and optionally substituted heterocycloalkyl.

Schemes 4 and 5 summarize two novel methods of preparing compound 105, which are not believed to have been previously described.

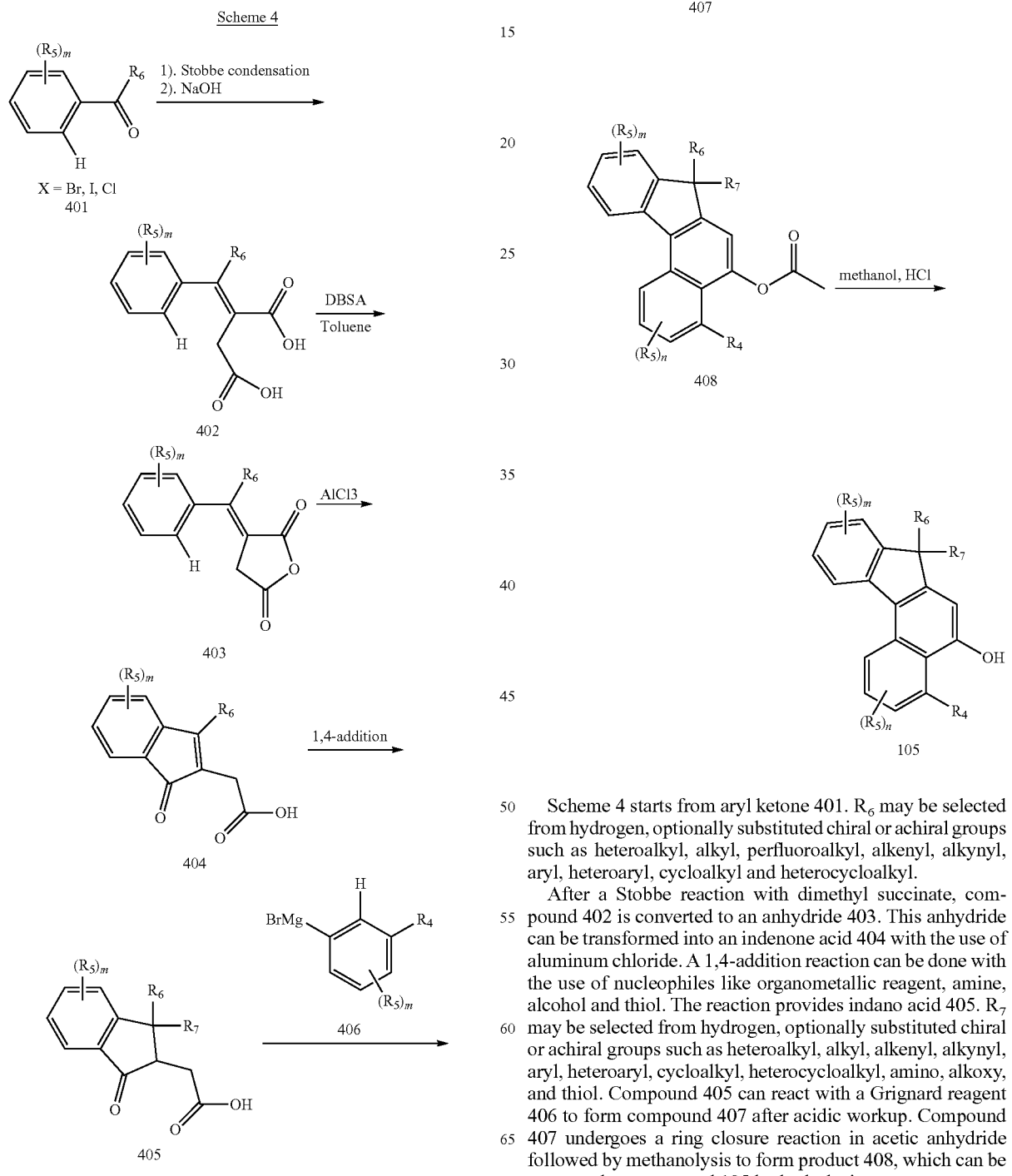

Scheme 4 starts from aryl ketone 401. $R_6$ may be selected from hydrogen, optionally substituted chiral or achiral groups such as heteroalkyl, alkyl, perfluoroalkyl, alkenyl, alkynyl, aryl, heteroaryl, cycloalkyl and heterocycloalkyl.

After a Stobbe reaction with dimethyl succinate, compound 402 is converted to an anhydride 403. This anhydride can be transformed into an indenone acid 404 with the use of aluminum chloride. A 1,4-addition reaction can be done with the use of nucleophiles like organometallic reagent, amine, alcohol and thiol. The reaction provides indano acid 405. $R_7$ may be selected from hydrogen, optionally substituted chiral or achiral groups such as heteroalkyl, alkyl, alkenyl, alkynyl, aryl, heteroaryl, cycloalkyl, heterocycloalkyl, amino, alkoxy, and thiol. Compound 405 can react with a Grignard reagent 406 to form compound 407 after acidic workup. Compound 407 undergoes a ring closure reaction in acetic anhydride followed by methanolysis to form product 408, which can be converted to compound 105 by hydrolysis.

Scheme 5

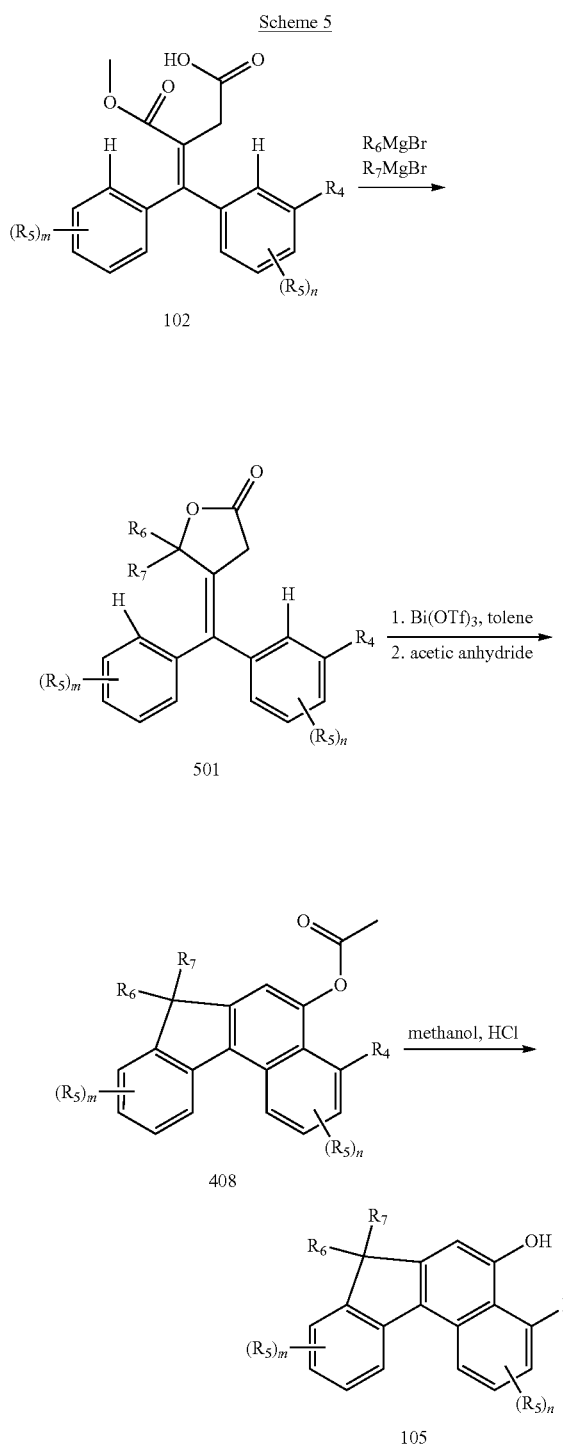

Scheme 6

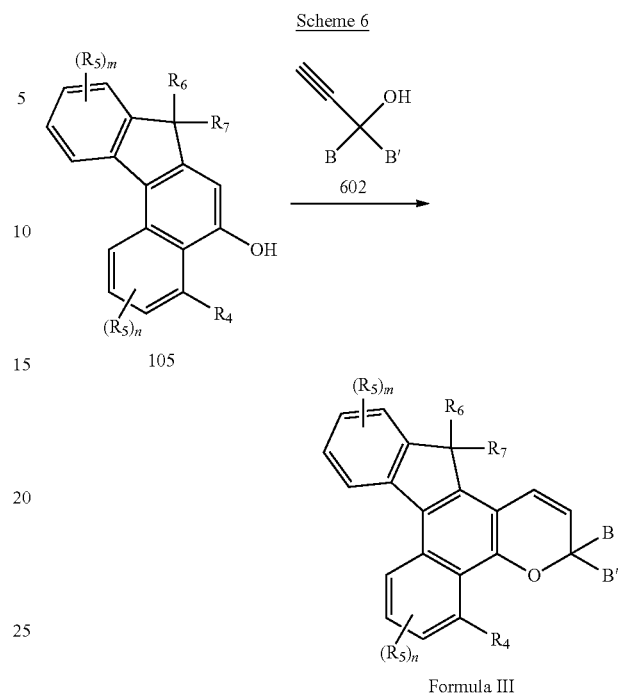

Scheme 6 illustrates methods of converting compounds 105 into Formula III. The pyran ring of Formula III is formed with the coupling with a propargyl alcohol 602. B and B' may be each independently selected from hydrogen, halogen, and optionally substituted chiral or achiral groups such as metallocenyl, alkyl or perfluoroalkyl, alkenyl, alkynyl, heteroalkyl, alkoxy, perfluoroalkoxy, aryl, heteroaryl, heterocycloalkyl, and cycloalkyl, or wherein B and B' are taken together with any intervening atoms to form a group such as optionally substituted cycloalkyl and optionally substituted heterocycloalkyl.

In all Schemes from 1 to 6, $R_4$ is installed before the formation of the naphthol. The following Scheme 7 and Scheme 8 show that $R_4$ can also be installed at the naphthol stage or after the photochromic compound is prepared.

In Scheme 7, the starting naphthol acetate 701 can be prepared using Scheme 1 to Scheme 5 with $R_4$ being a hydrogen with an alkoxy ortho to it. $R_8$ is an alkyl.

Scheme 7

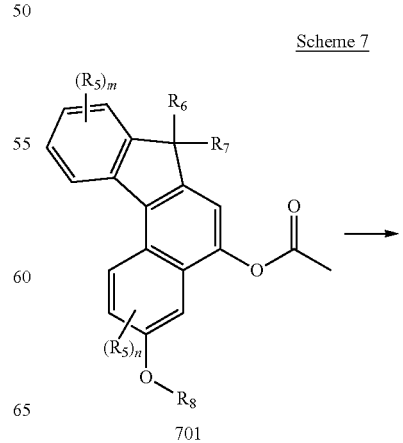

Scheme 5 starts from Stobbe product 102, which reacts with Grignard reagent to provide compound 501. $R_6$ and $R_7$ may be selected from optionally substituted chiral or achiral groups such as heteroalkyl, alkyl, perfluoroalkyl, alkenyl, alkynyl, aryl, heteroaryl, cycloalkyl and heterocycloalkyl. After treating with bismuth triflate in toluene and then acetic anhydride, two ring closure reactions occur in the same pot sequentially. The efficient reaction results in compound 408, which can be converted into compound 105.

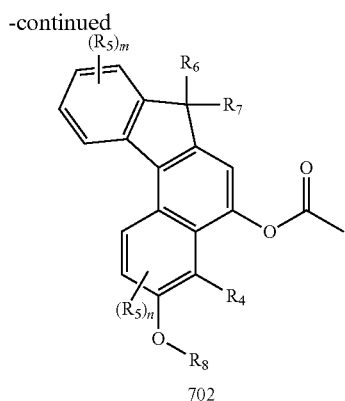

702

When 701 is treated with an electrophile like N-bromosuccinimide or N-chlorosuccinimide, $R_4$ is substituted on 702 as bromine or chlorine. Examples 5-7 were prepared using this method.

In Scheme 8, the photochromic dye 801 can be prepared using Scheme 1 to Scheme 6. The fluorine at the 5-position can be replaced with $R_4$ being an alkylamine or alkoxide neucleophile to provide 802 and 803, in which $R_8$ and $R_9$ are alkyls. Examples 19-22 and 24 were prepared this way.

(f) a photochromic polymer; or
(g) mixtures thereof.

The present invention further provides a photochromic article comprising an organic material and a photochromic compound/composition of the present disclosure connected to at least a portion of the organic host material. As used herein the term "connected to" means in direct contact with an object or indirect contact with an object through one or more other structures or materials, at least one of which is in direct contact with the object. Further, the photochromic compound can be connected to at least a portion of the host by incorporation into the host material or by application onto the host material, for example, as part of a coating or layer. In addition to the photochromic compound, the photochromic composition may further comprise at least one additive chosen from dyes, alignment promoters, antioxidants, kinetic enhancing additives, photoinitiators, thermal initiators, polymerization inhibitors, solvents, light stabilizers, e.g., ultraviolet light absorbers and hindered amines stabilizers, heat stabilizers, mold release agents, rheology control agents, leveling agents, free radical scavengers, gelators and adhesion promoters.

Non-limiting examples of organic host materials that may be used in conjunction with various non-limiting embodiments disclosed herein include liquid crystal materials and polymeric materials.

Scheme 8

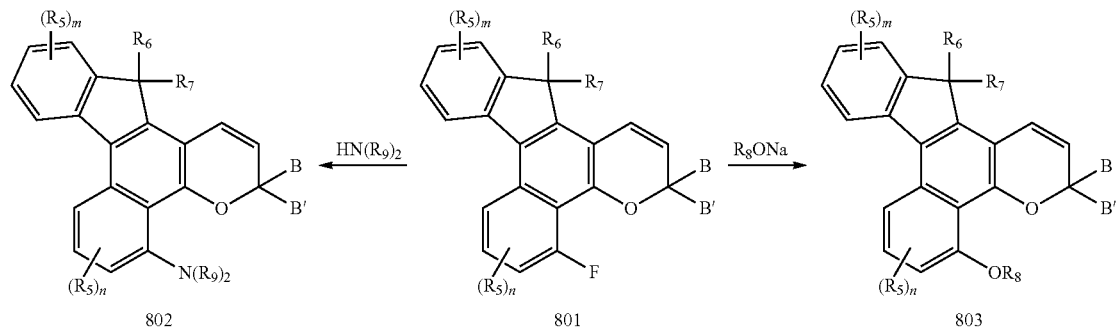

The compounds described herein may be useful as photochromic materials, such as thermally reversible photochromic compounds and/or compositions according to various non-limiting embodiments disclosed herein. Such compounds may be useful in a variety of applications to provide photochromic and, where applicable, photochromic-dichroic properties.

The photochromic compositions of the present invention may comprise at least one of the compounds described herein, and optionally at least one other photochromic compound. The photochromic composition can be chosen from a variety of materials. Examples of such materials may be selected from:
(a) a single photochromic compound;
(b) a mixture of photochromic compounds;
(c) a material comprising at least one photochromic compound such as a polymeric resin or an organic monomer solution;
(d) a material such as a monomer or polymer to which at least one photochromic compound is chemically bonded;
(e) material (c) or (d) further comprising a coating to substantially prevent contact of the at least one photochromic compound with external materials;

Examples of suitable polymeric materials include homopolymers and copolymers, prepared from the monomers and mixtures of monomers disclosed in U.S. Pat. No. 5,962,617 and in U.S. Pat. No. 5,658,501 from column 15, line 28 to column 16, line 17, wherein the disclosures of such polymeric materials in these U.S. patents are specifically incorporated herein by reference, an oligomeric material, a monomeric material or a mixture or combination thereof. Polymeric materials can be thermoplastic or thermoset polymeric materials, can be transparent or optically clear, and can have any refractive index required. Non-limiting examples of such disclosed monomers and polymers include: polyol(allyl carbonate) monomers, e.g., allyl diglycol carbonates such as diethylene glycol bis(allyl carbonate), which monomer is sold under the trademark CR-39 by PPG Industries, Inc.; polyurea-polyurethane (polyurea-urethane) polymers, which are prepared, for example, by the reaction of a polyurethane prepolymer and a diamine curing agent, a composition for one such polymer being sold under the trademark TRIVEX by PPG Industries, Inc.; polyol(meth)acryloyl terminated carbonate monomer; diethylene glycol dimethacrylate monomers; ethoxylated phenol methacrylate monomers; diisopropenyl benzene monomers; ethoxylated trimethylol propane triacrylate monomers; ethylene glycol bismethacrylate monomers; poly(ethylene glycol) bismethacrylate monomers; urethane acrylate monomers; poly(ethoxylated bisphenol A dimethacrylate); poly(vinyl acetate); poly(vinyl alcohol); poly(vinyl chloride); poly(vinylidene chloride); polyethylene; polypropylene; polyurethanes; polythiourethanes; thermoplastic polycarbonates, such as the carbonate-linked resin derived from bisphenol A and phosgene, one such material being sold under the trademark LEXAN; polyesters, such as the material sold under the trademark MYLAR; poly (ethylene terephthalate); polyvinyl butyral; poly(methyl methacrylate), such as the material sold under the trademark PLEXIGLAS, and polymers prepared by reacting polyfunctional isocyanates with polythiols or polyepisulfide monomers, either homopolymerized or co- and/or terpolymerized with polythiols, polyisocyanates, polyisothiocyanates and optionally ethylenically unsaturated monomers or halogenated aromatic-containing vinyl monomers. Also contemplated are copolymers of such monomers and blends of the described polymers and copolymers with other polymers, for example, to form block copolymers or interpenetrating network products. Polymeric materials can also be self-assembled materials.

The polymer may be a block or non-block copolymer. Such block copolymers may comprise hard blocks and soft blocks. Further, the polymer may be a non-block copolymer (i.e., a copolymer that does not have large blocks of specific monomer residues), such as a random copolymer, an alternating copolymer, periodic copolymers, and statistical copolymers. The present disclosure is also intended to cover copolymers of more than two different types of co-monomer residues.

The organic host material can be chosen from polyacrylates, polymethacrylates, poly($C_1$-$C_{12}$)alkyl methacrylates, polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), poly(vinylpyrrolidone), poly((meth)acrylamide), poly(dimethyl acrylamide), poly(hydroxyethyl methacrylate), poly((meth)acrylic acid), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, mono-functional acrylate monomers, mono-functional methacrylate monomers, polyfunctional acrylate monomers, polyfunctional methacrylate monomers, diethylene glycol dimethacrylate monomers, diisopropenyl benzene monomers, alkoxylated polyhydric alcohol monomers and diallylidene pentaerythritol monomers.

Also, the organic host material can be a homopolymer or copolymer of monomer(s) chosen from acrylates, methacrylates, methyl methacrylate, ethylene glycol bis methacrylate, ethoxylated bisphenol A dimethacrylate, vinyl acetate, vinylbutyral, urethane, thiourethane, diethylene glycol bis(allyl carbonate), diethylene glycol dimethacrylate, diisopropenyl benzene, and ethoxylated trimethylol propane triacrylate. Ther polymeric material most often comprises liquid crystal materials, self-assembling materials, polycarbonate, polyamide, polyimide, poly(meth)acrylate, polycyclic alkene, polyurethane, poly(urea)urethane, polythiourethane, polythio(urea)urethane, polyol(allyl carbonate), cellulose acetate, cellulose diacetate, cellulose triacetate, cellulose acetate propionate, cellulose acetate butyrate, polyalkene, polyalkylene-vinyl acetate, poly(vinylacetate), poly(vinyl alcohol), poly (vinyl chloride), poly(vinylformal), poly(vinylacetal), poly (vinylidene chloride), poly(ethylene terephthalate), polyester, polysulfone, polyolefin, copolymers thereof, and/or mixtures thereof.

Further, the organic host material can form an optical element or portion thereof. Non-limiting examples of optical elements include ophthalmic elements, display elements, windows, and mirrors. As used herein the term "optical" means pertaining to or associated with light and/or vision. For example, although not limiting herein, according to various non-limiting embodiments, the optical element or device can be chosen from ophthalmic elements and devices, display elements and devices, windows, mirrors, packaging material such as shrinkwrap, and active and passive liquid crystal cell elements and devices.

As used herein the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intraocular lenses, magnifying lenses, and protective lenses or visors. As used herein the term "display" means the visible or machine-readable representation of information in words, numbers, symbols, designs or drawings. Non-limiting examples of display elements and devices include screens, monitors, and security elements, including without limitation, security marks and authentication marks. As used herein the term "window" means an aperture adapted to permit the transmission of radiation therethrough. Non-limiting examples of windows include automotive and aircraft transparencies, filters, shutters, and optical switches. As used herein the term "mirror" means a surface that specularly reflects a large fraction of incident light.

For example, the organic host material can be an ophthalmic element, and more particularly, an ophthalmic lens.

Further, it is contemplated that the photochromic compounds disclosed herein can be used alone or in conjunction with at least one other complementary organic photochromic compound having at least one activated absorption maxima within the range of 300 nm to 1000 nm, inclusive (or substances containing the same). For example, the photochromic compound disclosed herein can be combined with at least one other conventional organic photochromic compound such that the combination of photochromic compound, when activated, exhibits a desired hue. Non-limiting examples of suitable conventional organic photochromic compounds include the pyrans, oxazines, fulgides and fulgimides described hereinafter.

Non-limiting examples of thermally reversible complementary photochromic pyrans include benzopyrans, naphthopyrans, e.g., naphtho[1,2-b]pyrans, naphtho[2,1-b]pyrans, indeno-fused naphthopyrans, such as those disclosed in U.S. Pat. No. 5,645,767, and heterocyclic-fused naphthopyrans, such as those disclosed in U.S. Pat. Nos. 5,723,072, 5,698,141, 6,153,126, and 6,022,497, which are hereby incorporated by reference for the disclosure of such naphthopyrans; spiro-9-fluoreno[1,2-b]pyrans; phenanthropyrans; quinopyrans; fluoroanthenopyrans: spiropyrans, e.g., spiro (benzindoline)naphthopyrans, spiro(indoline)benzopyrans, spiro(indoline)naphthopyrans, spiro(indoline)quinopyrans and spiro(indoline)pyrans. More specific examples of naphthopyrans and the complementary organic photochromic substances are described in U.S. Pat. No. 5,658,501, the disclosures of which are hereby specifically incorporated by reference. Spiro(indoline)pyrans are also described in the text, *Techniques in Chemistry*, Volume III, "Photochromism", Chapter 3, Glenn H. Brown, Editor, John Wiley and Sons, Inc., New York, 1971, the disclosure of which is hereby incorporated by reference.

Non-limiting examples of thermally reversible complementary photochromic oxazines include benzoxazines, naphthoxazines, and spiro-oxazines, e.g., spiro(indoline)naphthoxazines, spiro(indoline)pyridobenzoxazines, spiro(benzindoline)pyridobenzoxazines, spiro(benzindoline)naphthoxazines, spiro(indoline)benzoxazines, spiro(indoline)fluoranthenoxazine, and spiro(indoline)quinoxazine.

More non-limiting examples of thermally reversible complementary photochromic fulgides include: fulgimides, and the 3-furyl and 3-thienyl fulgides and fulgimides, which are disclosed in U.S. Pat. No. 4,931,220 (wherein the disclosures of such fulgimides are hereby specifically incorporated by reference) and mixtures of any of the aforementioned photochromic materials/compounds.

For example, it is contemplated that the photochromic compounds disclosed herein can be used alone or in conjunction with another conventional organic photochromic compound (as discussed above), in amounts or ratios such that the organic host material into which the photochromic compounds are incorporated, or onto which the organic host materials are applied, can exhibit a desired color or colors, either in an activated or a "bleached" state. Thus the amount of the photochromic compounds used is not critical provided that a sufficient amount is present to produce a desired photochromic effect. As used herein, the term "photochromic amount" refers to the amount of the photochromic compound necessary to produce the desired photochromic effect.

The present invention also provides a photochromic article comprising a substrate, and an at least partial coating of a coating composition having a photochromic amount of a photochromic compound of the present disclosure connected to at least a portion of at least one surface thereof of the substrate. Further, although not limiting herein, at least a portion of the at least partial coating can be at least partially set. As used herein the term "set" means to fix in a desired orientation.

For example, according to the above-mentioned non-limiting embodiment, the coating composition can be chosen from, without limitation, polymeric coating compositions, paints, and inks. Further, in addition to the photochromic compounds disclosed herein, the coating compositions according to various non-limiting embodiments can further comprise at least one other conventional organic photochromic compounds having at least one activated absorption maxima within the range of 300 nm to 1000 nm, inclusive.

Non-limiting examples of suitable substrates to which the coating composition comprising the photochromic amount of the photochromic compounds can be applied include glass, masonry, textiles, ceramics, metals, wood, paper and polymeric organic materials. Non-limiting examples of suitable polymeric organic materials are set forth above.

Further provided are optical elements comprising a substrate and an at least partial coating comprising at least one photochromic compound of the present disclosure connected to at least a portion of the substrate. Non-limiting examples of optical elements include, ophthalmic elements, display elements, windows, and mirrors. For example, the optical element can be an ophthalmic element, and the substrate can be an ophthalmic substrate chosen from corrective and non-corrective lenses, partially formed lenses, and lens blanks.

Although not limiting herein, the optical elements can comprise any amount of the photochromic compound necessary to achieve the desired optical properties, such as but not limited to, photochromic properties and dichroic properties.

Other non-limiting examples of substrates that are suitable for use in conjunction with the foregoing non-limiting embodiment include untinted substrates, tinted substrates, photochromic substrates, tinted-photochromic substrates, linearly polarizing substrates, circularly polarizing substrates, elliptically polarizing substrates, reflective substrates, and wave plates or retarder substrates, e.g., quarter wave plate and half wave plate. As used herein with reference to substrates the term "untinted" means substrates that are essentially free of coloring agent additions (such as, but not limited to, conventional dyes) and have an absorption spectrum for visible radiation that does not vary significantly in response to actinic radiation. Further, with reference to substrates the term "tinted" means substrates that have a coloring agent addition (such as, but not limited to, conventional dyes) and an absorption spectrum for visible radiation that does not vary significantly in response to actinic radiation.

As used herein the term "linearly polarizing" with reference to substrates refers to substrates that are adapted to linearly polarize radiation (i.e., confine the vibrations of the electric vector of light waves to one direction). As used herein the term "circularly polarizing" with reference to substrates refers to substrates that are adapted to circularly polarize radiation. As used herein the term "elliptically polarizing" with reference to substrates refers to substrates that are adapted to elliptically polarize radiation. As used herein with the term "photochromic" with reference to substrates refers to substrates having an absorption spectrum for visible radiation that varies in response to at least actinic radiation and is thermally reversible. Further, as used herein with reference to substrates, the term "tinted-photochromic" means substrates containing a coloring agent addition as well as a photochromic compound, and having an absorption spectrum for visible radiation that varies in response to at least actinic radiation and is thermally reversible. Thus for example, the tinted-photochromic substrate can have a first color characteristic of the coloring agent and a second color characteristic of the combination of the coloring agent and the photochromic compound when exposed to actinic radiation.

The present invention also is directed to an optical element comprising a substrate and an at least partial coating comprising at least one photochromic compound of the present disclosure connected to at least a portion of the substrate. As discussed above, the optical elements according to the present invention can be display elements, such as, but not limited to screens, monitors, and security elements. For example, the optical element can be a display element comprising a first substrate having a first surface, a second substrate having a second surface, wherein the second surface of the second substrate is opposite and spaced apart from the first surface of the first substrate so as to define a gap; and a fluid material comprising at least one photochromic compound of the present disclosure positioned within the gap defined by the first surface of the first substrate and the second surface of the second substrate.

The first and second substrates can be independently chosen from untinted substrates, tinted substrates, photochromic substrates, tinted-photochromic substrates, linearly polarizing substrates, circularly polarizing substrates, elliptically polarizing substrates and reflective substrates and retarder substrates.

The present invention also provides a security element comprising a substrate and at least one photochromic compound of the present disclosure connected to at least a portion of the substrate. Non-limiting examples of security elements include security marks and authentication marks that are connected to at least a portion of a substrate, such as and without limitation: access cards and passes, e.g., tickets, badges, identification or membership cards, debit cards etc.; negotiable instruments and non-negotiable instruments e.g., drafts, checks, bonds, notes, certificates of deposit, stock certificates, etc.; government documents, e.g., currency, licenses, identification cards, benefit cards, visas, passports, official certificates, deeds etc.; consumer goods, e.g., software, compact discs ("CDs"), digital-video discs ("DVDs"), appliances, consumer electronics, sporting goods, cars, etc.; credit cards; and merchandise tags, labels and packaging.

Although not limiting herein, the security element can be connected to at least a portion of a substrate chosen from a transparent substrate and a reflective substrate. Alternatively, wherein a reflective substrate is required, if the substrate is not reflective or sufficiently reflective for the intended application, a reflective material can be first applied to at least a portion of the substrate before the security mark is applied thereto. For example, a reflective aluminum coating can be applied to the at least a portion of the substrate prior to forming the security element thereon. Still further, security element can be connected to at least a portion of a substrate chosen from untinted substrates, tinted substrates, photochromic substrates, tinted-photochromic substrates, linearly polarizing, circularly polarizing substrates, and elliptically polarizing substrates.

Furthermore, the aforementioned security element can further comprise one or more other coatings or sheets to form a multi-layer reflective security element with viewing angle dependent characteristics as described in U.S. Pat. No. 6,641,874, which disclosure related to multireflective films is hereby specifically incorporated by reference herein.

The photochromic articles and optical elements described above can be formed by methods known in the art. Although not limiting herein, it is contemplated that the photochromic compounds disclosed herein can be connected to a substrate or host by incorporation into the host material or application onto the host or substrate, such as in the form of a coating.

For example, the photochromic compound can be incorporated into an organic host material by dissolving or dispersing the photochromic compound within the host material, e.g., casting it in place by adding the photochromic compound to the monomeric host material prior to polymerization, imbibition of the photochromic compound into the host material by immersion of the host material in a hot solution of the photochromic compound or by thermal transfer. As used herein the term "imbibition" includes permeation of the photochromic compound alone into the host material, solvent assisted transfer of the photochromic compound into a porous polymer, vapor phase transfer, and other such transfer methods.

Additionally, the photochromic compound disclosed herein can be applied to the organic host material or other substrate as part of a coating composition (as discussed above) or a sheet comprising the photochromic compound. As used herein the term "coating" means a supported film derived from a flowable composition, which may or may not have a uniform thickness. As used herein the term "sheet" means a pre-formed film having a generally uniform thickness and capable of self-support. In such cases ultraviolet light absorbers can be admixed with the photochromic materials before their addition to the coating or sheet or such absorbers can be superposed, e.g., superimposed, as a coating or film between the photochromic article and the incident light.

Non-limiting methods of applying coating compositions comprising the photochromic compounds disclosed herein include those methods known in the art for applying coatings, such as, spin coating, spray coating, spray and spin coating, curtain coating, flow coating, dip coating, injection molding, casting, roll coating, wire coating, and overmolding. The coating (which may be in the form of a coating composition) comprising the photochromic compound can be applied to a mold and the substrate can be formed on top of the coating (i.e., overmolding). Additionally or alternatively, a coating composition without the photochromic compound can be first applied to the substrate or organic host material using any of the aforementioned techniques and thereafter imbibed with the photochromic compound as described above.

Non-limiting examples of coating compositions of film forming polymers that can include photochromic materials are as follows: photochromic/dichroic liquid crystal coatings, such as those described in U.S. Pat. No. 7,256,921 at column 2, line 60 to column 94, line 23; photochromic polyurethane coatings, such as those described in U.S. Pat. No. 6,187,444 at column 3, line 4 to column 12, line 15; photochromic aminoplast resin coatings, such as those described in U.S. Pat. No. 6,432,544 at column 2, line 52 to column 14, line 5 and U.S. Pat. No. 6,506,488 at column 2, line 43 to column 12, line 23; photochromic polysiloxane coatings, such as those described in U.S. Pat. No. 4,556,605 at column 2, line 15 to column 7, line 27; photochromic poly(meth)acrylate coatings, such as those described in U.S. Pat. No. 6,602,603 at column 3, line 15 to column 7, line 50, U.S. Pat. No. 6,150,430 at column 8, lines 15-38, and U.S. Pat. No. 6,025,026 at column 8, line 66 to column 10, line 32; polyanhydride photochromic coatings, such as those described in U.S. Pat. No. 6,436,525 at column 2, line 52 to column 11, line 60; photochromic polyacrylamide coatings such as those described in U.S. Pat. No. 6,060,001 at column 2, line 6 to column 5, line 40; photochromic epoxy resin coatings, such as those described in U.S. Pat. No. 6,268,055 at column 2, line 63 to column 15, line 12; and photochromic poly(urea-urethane) coatings, such as those described in U.S. Pat. No. 6,531,076 at column 2, line 60 to column 10, line 49. The disclosures in the aforementioned U.S. Patents that relate to the film-forming polymers are hereby incorporated herein by reference.

Non-limiting methods of applying sheets comprising the photochromic compound disclosed herein to a substrate include, for example, at least one of: laminating, fusing, in-mold casting, and adhesively bonding the polymeric sheet to the at least a portion of the substrate. As used herein, the in-mold casting includes a variety of casting techniques, such as but not limited to: overmolding, wherein the sheet is placed in a mold and the substrate is formed (for example by casting) over at least a portion of the substrate; and injection molding, wherein the substrate is formed around the sheet. Further, it is contemplated that the photochromic compound can be applied to the sheet as a coating, incorporated into the sheet by imbibition or by other suitable methods, either prior to applying the sheet to the substrate or thereafter.

The polymeric sheet can comprise a polymeric composition of any of a wide variety of polymers, including both thermosetting polymers and thermoplastic polymers. As used herein, the term "polymer" is intended to include both polymers and oligomers, as well as both homopolymers and copolymers. Such polymers can include, for example, acrylic polymers, polyester polymers, polyurethane polymers, poly(urea)urethane polymers, polyamine polymers, polyepoxide polymers, polyamide polymers, polyether polymers, polysiloxane polymers, polysulfide polymers, copolymers thereof, and mixtures thereof. Generally these polymers can be any polymers of these types made by any method known to those skilled in the art.

The polymers used to form the polymeric sheet also may comprise functional groups including, but not limited to, carboxylic acid groups, amine groups, epoxide groups, hydroxyl groups, thiol groups, carbamate groups, amide groups, urea groups, isocyanate groups (including blocked isocyanate groups) mercaptan groups, groups having ethylenic unsaturation e.g., acrylate groups), vinyl groups, and combinations thereof. Appropriate mixtures of film-forming resins may also be used in the preparation of the coating compositions. If the polymer composition from which the polymeric sheet is formed comprises functional group-containing polymers (such as any of the previously mentioned functional group-containing polymers), the polymer composition can further comprise a material having functional groups reactive with those of said polymer. Reaction may be facilitated, for example, by thermal, photoinitiated, oxidative, and/or radiative curing techniques. Also contemplated are mixtures of any of the foregoing polymers.

Further non-limiting examples of polymers suitable for use in forming the polymeric sheet of the present invention are the thermoplastic block copolymers of polyalkyl(meth)acrylate and polyamide described in Published U.S. Patent Application 2004/0068071 A1 at paragraphs [0020]-[0042], the specified portions of which is incorporated by reference herein; and U.S. Pat. No. 6,096,375 at column 18, line 8 to column 19, line 5, the specified portions of which are incorporated by reference herein.

The polymeric sheet can comprise an elastomeric polymer, for example thermoplastic elastomeric polymers. As used herein, by "elastomeric polymer" is meant a polymer that has a high degree of resiliency and elasticity such that it is capable of at least partially reversible deformation or elongation. In some instances, when stretched, the molecules of an elastomer are aligned and can take on aspects of a crystalline arrangement; and upon release, the elastomer can, to some extent, return to its natural disordered state. For purposes of the present invention, elastomeric polymers can include thermoplastic, thermoplastic elastomeric polymers, and thermosetting polymers provided such polymers fall within the description provided above for "elastomeric polymer".

The elastomeric polymer can comprise any of wide variety of art recognized elastomers including but not limited to copolymers of any of the previously mentioned polymers. In an embodiment of the present invention, the elastomeric polymer can comprise a block copolymer having ether and/or ester linkages in the polymer backbone. Examples of suitable block copolymers can include, but are not limited to, poly(amide-ether) block copolymers, poly(ester-ether) block copolymers, poly(ether-urethane) block copolymers, poly(ester-urethane) block copolymers, and/or poly(ether-urea) block copolymers. Suitable specific examples of such elastomeric polymers can include, but are not limited to, those commercially available under the tradenames DESMOPAN® and TEXIN® from Bayer Material Science; ARNITEL® from Royal DSM; and PEBAX® from Atofina Chemicals or Cordis Corporation.

Moreover, as discussed above, the photochromic compounds disclosed herein can be incorporated or applied alone, or in combination with at least one other conventional organic photochromic compound, which can also be applied or incorporated into the host materials and substrates as described above. Additional coatings may be applied to the photochromic article including other photochromic coatings, anti-reflective coatings, linearly polarizing coatings, transitional coatings, primer coatings, adhesive coatings, mirrored coatings and protective coatings including antifogging coatings, oxygen barrier coatings and ultraviolet light absorbing coatings.

The embodiments described herein are further illustrated by the following non-limiting examples.

EXAMPLES

The present invention has been described with reference to specific details of particular embodiments thereof. It is not intended that such details be regarded as limitations upon the scope of the invention except insofar as to the extent that they are included in the accompanying claims.

Examples

In Part 1 of the Examples, the synthesis procedures used to make photochromic materials according to various non-limiting embodiments disclosed herein are set forth in Examples 1-26 as well as the Comparative Examples (CE)1-7. Part 2 describes the photochromic performance testing and results for Examples 1-22, 24 and 26 and CE 1-7.

Part 1

Synthesis Procedures

Example 1

Step 1

Magnesium (2 g) was placed in a dry flask equipped with a dropping funnel which contained a mixture of tribromobenzene (27.5 g) and THF (200 ml). The solution (20 ml) in the dropping funnel was added to the flask. A few drops of dibromoethane were also added to the flask and in a few minutes the contents in the reaction flask started to boil. The rest of the solution in the dropping funnel was added drop wise. Ice water was used occasionally to cool the reaction mixture. After the addition, the mixture was stirred at room temperature for two hours. At 0° C., bis[2-(N,N-dimethylamino)ethyl]ether (14 g) was added and stirred for 30 minutes. Benzoyl chloride (12.3 g) was added in one portion and the mixture was stirred for 4 hours at 0° C. Water (500 ml) was added to the mixture. 3N HCl was used to adjust pH to ~5. Ethyl acetate was added to the mixture (500 ml). The resulting organic layer was collected, washed with water, washed with sodium bicarbonate, dried over magnesium sulfate and concentrated. The product was purified by a silica gel plug column using 8/2; v/v of hexanes/ethyl acetate (EtOAc) as eluent. Viscous oil (8 g) was obtained as the product. NMR indicated that the product had a structure consistent with 3,5-dibromobenzophenone. The same reaction was scaled up so that sufficient product for the next step was obtained.

Step 2

The product from Step 1 (30 g), dimethyl succinate (17 g) and toluene (500 ml) were added to a reaction flask equipped with a mechanical stirrer, a solid addition funnel and a nitrogen blanket. The mixture was stirred at room temperature until the solids dissolved. Potassium t-butoxide (11 g) was added through the solid addition funnel and the mixture was stirred at room temperature for 2 hours. The resulting reaction mixture was poured into 1 L of water and the aqueous layer, which contained the product, was collected. The toluene layer was extracted with 200 ml water. The combined water solution was washed with toluene. HCl (3 N) was added to the water solution to adjust the pH to 5. The resulting mixture was extracted with ethyl acetate, dried over magnesium sulfate, concentrated and dried in vacuum. Light yellow solid was obtained as the product. It was used directly in the next step.

Step 3

The product from Step 2 and acetic anhydride (200 ml) was mixed and refluxed in a reaction flask equipped with a condenser. After two hours, the acetic anhydride was removed by vacuum evaporation and the recovered oil was used directly in the next step.

Step 4

To a reaction flask containing the oil obtained from Step 3 was added methanol (200 mL) and HCl (12 N, 2 ml). The mixture was refluxed for two hours. Methanol was removed by vacuum evaporation. The recovered oil was dissolved in ethyl acetate, washed with sodium bicarbonate saturated water, dried over magnesium sulfated, concentrated until white crystals started to form from a hot solution. The mixture was cooled to room temperature. White crystals were collected and dried (8.8 g). Proton Nuclear Magnetic Resonance (NMR) indicated that the product had a structure consistent with 2,4-dibromo-7,7-dimethyl-7H-benzo[c]fluoren-5-ol.

Step 5

The product (8.8 g) from Step 4 was dissolved in anhydrous THF (200 ml) in an oven dried flask equipped with a dropping funnel and a magnetic stir bar. The mixture was stirred at room temperature and 1.4 M THF solution of methyl magnesium bromide (43 ml) was added dropwise. After the addition, the mixture was stirred at room temperature for about 4 hours. The reaction mixture was then poured into 200 ml of ice water and the pH was adjusted to ~5 using HCl (3 N). Ethyl acetate (200 mL) was added and the resulting organic layer was separated, dried over magnesium sulfate, concentrated and dried in vacuum. The recovered white solid was used directly in the next step.

Step 6

The product from Step 5, bismuth triflate (0.5 g) and toluene (100 mL) were added to a reaction flask equipped with a magnetic stir bar. The mixture was refluxed for one hour. The reaction mixture was then used directly in the next step.

Step 7

Half amount of the product from Step 6 was transferred to another reaction flask. To the flask was added 1,1-bis(4-methoxyphenyl)prop-2-yn-1-ol (2.7 g) and a few crystals of p-toluenesulfonic acid. The mixture was stirred at room temperature for one hour. The product was purified using a CombiFlash Rf from Teledyne ISCO followed by recrystallization from acetone. Yellow crystals were obtained as the product (2.54 g). NMR analysis indicated that the product had a structure consistent with 3,3-bis(4-methoxyphenyl)-5,7-dibromo-13,13-dimethyl-3H,13H-indeno[2',3':3,4]naphtho[1,2-b]pyran represented by the following graphic formula:

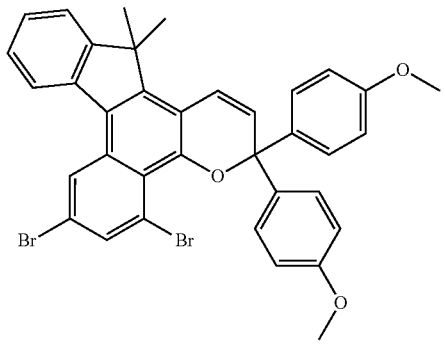 [SMILES: COc1ccc(C2(c3ccc(OC)cc3)C=Cc3c4c(c5cc(Cl)cc(Cl)c5c3O2)-c2ccccc2C4(C)C)cc1]

Example 2

Step 1

Magnesium (5.38 g) and THF (50 ml) were placed in a dry flask equipped with a dropping funnel which contained a mixture of 1-bromo-3,5-dichlorobenzene (50 g) and THF (300 ml). The solution in the dropping funnel (30 ml) was added to the flask. A few drops of dibromoethane was also added and a few minutes later the contents in the reaction flask started to boil. The remainder of the solution in the dropping funnel was added drop wise. Ice water was used occasionally to cool the reaction mixture. After the addition, the mixture was stirred at room temperature for two hours. Benzonitrile (22.82 g) was then added to the reaction mixture and the resulting mixture was refluxed for 2 days. 3 N HCl (300 ml) was added. The mixture was stirred for 4 hours and then extracted using ethyl acetate. The resulting organic layer was collected by a seperatory funnel and then concentrated. The recovered oil (49 g) was used in the next step without further purification.

Step 2

The product from Step 1 (47 g), dimethyl succinate (36 g) and toluene (500 ml) were added to a reaction flask equipped with a mechanical stirrer, a solid addition funnel and a nitrogen blanket. The mixture was stirred at room temperature until the solids were dissolved. Solid potassium t-butoxide (23.1 g) was added through the solid addition funnel and the mixture was stirred at room temperature for 4 hours. The resulting reaction mixture was poured into 1 L of water and the resulting aqueous layer, which contained the product, was collected. The recovered toluene layer was extracted with 200 ml water. The combined water solutions were washed with toluene. HCl (3 N) was added to the resulting water solution to adjust the pH to 5. The resulting mixture was extracted with ethyl acetate, dried over magnesium sulfate, concentrated and dried in vacuum. Oil was obtained as product. It was used directly in the next step.

Step 3

The product from Step 2 and acetic anhydride (200 ml) was mixed and refluxed in a reaction flask equipped with a condenser. After one hour, the acetic anhydride was removed by vacuum evaporation and the resulting oil was used directly in the next step.

Step 4

To a reaction flask containing the product from Step 3 was added methanol (500 mL) of and HCl (12 N, 1 ml). The mixture was refluxed for two hours. Methanol was removed by vacuum evaporation. The recovered oil was dissolved in methylene chloride, washed with sodium bicarbonate saturated water, dried over magnesium sulfate, concentrated and dried under vacuum. Clear oil (48 g) was obtained. Ethyl acetate/hexane (1/9) was used to crystallize the product. White crystals (12 g) were obtained as the product. NMR indicated that the product had a structure consistent with 2,4-dichloro-7,7-dimethyl-7H-benzo[c]fluoren-5-ol.

Step 5

The procedures from Step 5 to 7 of Example 1 were followed except that 2,4-dichloro-7,7-dimethyl-7H-benzo[c] fluoren-5-ol was used in place of 2,4-dibromo-7,7-dimethyl-7H-benzo[c]fluoren-5-ol. Off-white crystals were obtained as the product. NMR analysis indicated that the product had a structure consistent with 3,3-bis(4-methoxyphenyl)-5,7-dichloro-13,13-dimethyl-3H,13H-indeno[2',3':3,4]naphtho[1,2-b]pyran represented by the following graphic formula:

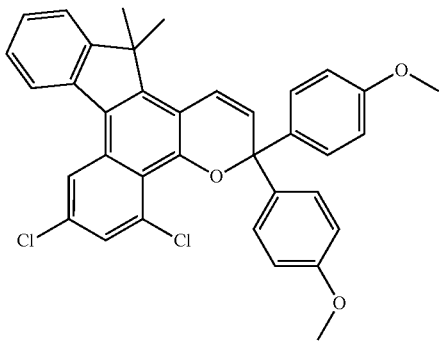

Example 3

Step 1

A 2 L flask with tribromobenzene (100 g) and a magnetic stir bar was dried in a vacuum oven at 80° C. for 4 hours. Dry THF (500 ml) was added and the resulting mixture was stirred. After the solids dissolved, a NaCl saturated ice bath was applied with the use of NaCl (1 Kg) and ice (2.45 Kg). 3M Isopropyl magnesium chloride (160 ml) was added drop wise at a rate that the kept the reaction temperature controlled to ~0° C. over about a 30 minutes to 1 hour interval. The mixture was stirred for half an hour at the same temperature. After lowering the temperature to −20-0 C, bis[2-(N,N-dimethylamino)ethyl]ether (61 g) was added slowly over 5 minutes. A large amount of precipitate formed. The suspension was stirred for 20 minutes and a mixture of 4-trifluoromethylbenzoyl chloride (73 g) and THF (100 ml) was added over 5 minutes. The mixture was stirred overnight and water (100 ml) was added slowly to quench the reaction. 3N HCl was used to adjust the pH to 2. The resulting organic layer was collected using a separatory funnel, washed with 5% NaOH/water and NaCl/water, dried and concentrated. To the recovered oil, methanol (300 ml) was added, crystallization was induced and white crystals were collected by filtration. NMR showed that the recovered white crystals (87 g) had a structure consistent with 3,5-dibromo-4'-trifluoromethylbenzophenone.

Step 2

The product of Step 1 (75 g), dimethyl succinic ester (32.2 g) and toluene (800 ml) were placed in a three neck 5 L flask equipped with a mechanical stir. Potassium t-butoxide (22.6 g) was added batch wise in half an hour. Heat generation and a large amount of precipitate was observed. After two hours, water (500 ml) was added and the pH of the resulting milky mixture was adjusted to ~2 using 3 N HCl. After stirring at room temperature for 10 minutes, the resulting organic layer was collected using a separatory funnel, washed with NaCl/HCl, dried over MgSO4. After concentration, hexanes were added to the product and the white crystals that formed were collected by filtration. NMR showed that the obtained product (62 grams) had a structure consistent with (E)-4-(3,5-dibromophenyl)-3-(methoxycarbonyl)-4-(4-(trifluoromethyl)phenyl)but-3-enoic acid.

Step 3

Anhydrous lanthanum (III) chloride (100 g) was ground to a very fine powder and then mixed with lithium chloride (52 g) and dry THF (1 liter) in a 5 liter three-neck flask equipped with a mechanical stir and a dropping funnel. The mixture was refluxed for a few hours until the solids dissolved. The product of Step 2 (106 g) was dissolved in the mixture. The mixture was then cooled to −15° C. A solution of 3M methyl magnesium chloride (238 ml) was placed in the dropping funnel. The first 30% of the Grignard was added into the mixture slowly. Generation of gas bubbles was observed. After the temperature dropped back to −15° C., the remainder of the Grignard reagent was added into the mixture over 2 minutes. After 30 minutes, water (1 L) was added slowly to the mixture and the pH was adjusted to 4 using acetic acid. The mixture became clear with formation of two layers. The water layer was drained off. The organic layer was washed with NaCl/water four times and then concentrated to dry. Light yellowish solid was obtained. The solid was re-dissolved in toluene, filtered through a silica gel plug column using toluene as the element. The resulting clear solution was concentrated to form a white solid product that was used in the next step without further purification. A sample was recrystallized from methanol and an NMR spectrum showed the purified crystals to have a structure consistent with (E)-4-((3,5-dibromophenyl)(4-(trifluoromethyl)phenyl)methylene)-5,5-dimethyldihydrofuran-2(3H)-one.

Step 4

All of the product of Step 3, toluene (500 ml), bismuth triflate (20 g) and acetic acid (0.24 g) were added to a reaction flask and stirred at reflux for 1 hour. After it cooled to room temperature, acetic anhydride (100 ml) was added. The mixture was heated to reflux again. After one hour, the mixture was cooled to room temperature and filtered through a silica gel plug column using toluene as the eluent. The recovered clear solution was concentrated to dry. Acetone (50 ml) was added to the obtained solid and a slurry was obtained. To the slurry mixture, methanol (250 ml) was added. The mixture was cooled and white crystals formed and were collected to yield (58 g) after drying. NMR showed that the product had a structure consistent with 8,10-dibromo-7,7-dimethyl-3-(trifluoromethyl)-7H-benzo[c]fluoren-5-yl acetate, which was the undesired regio-isomer for this example. The desired isomer was in the mother liquor. The mother liquor was concentrated to oil and used directly in the next step.

Step 5

To a reaction flask containing all of the product from Step 4 was added methanol (200 mL) and HCl (12 N, 2 ml). The mixture was refluxed for two hours. Methanol was removed by vacuum evaporation. The recovered oil was purified by a silica gel plug column followed by recrystallization from hexanes. White crystals were collected and dried (7.2 g). NMR indicated that the product had a structure consistent with 2,4-dibromo-7,7-dimethyl-9-(trifluoromethyl)-7H-benzo[c]fluoren-5-ol.

Step 6

To a chloroform solution (100 mL) of the product from Step 5, (4.86 g) was added 1-(4-butoxyphenyl)-1-(4-methoxyphenyl)prop-2-yn-1-ol (3.72 g) and 4-dodecylbenzenesulfonic acid (0.33 g). The solution was heated to reflux for 3 h. The reaction mixture was concentrated under reduced pressure to provide an oily residue. The residue was purified by column chromatography using 4:1 hexane toluene mixtures as the eluent. Fractions containing the desired material were grouped and concentrated to a purple foam (5.4 g) which solidified. NMR analysis of the purple solid indicated a structure that was consistent with 3-(4-butoxyphenyl)-3-(4-methoxyphenyl)-5,7-dibromo-11-trifluoromethyl-13,13-dimethyl-3H,13H-indeno[2',3':3,4]naphtho[1,2-b]pyran represented by the following graphic formula:

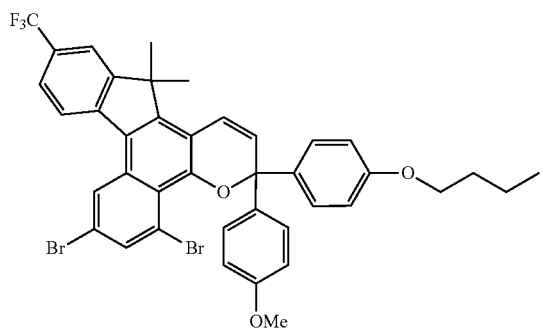 [SMILES: CCCCOc1ccc(C2(c3ccc(OC)cc3)C=Cc3c4c(c5cc(Br)cc(Br)c5c3O2)-c2ccc(C(F)(F)F)cc2C4(C)C)cc1]

Example 4

Step 1

The procedures from Step 1 to Step 5 of Example 3 were followed except that in Step 1, 3,5-difluorobenzoyl chloride was used in place of 4-trifluoromethylbenzoyl chloride; in Step 4, the mixture of products was used directly in Step 5; and in Step 5, the desired 8,10-dibromo-2,4-difluoro-7,7-dimethyl-7H-benzo[c]fluoren-5-ol was recrystallized out using ethyl acetate as solvent. NMR indicated that the product had a structure consistent with 8,10-dibromo-2,4-difluoro-7,7-dimethyl-7H-benzo[c]fluoren-5-ol.

Step 2

The procedure from Step 6 of Example 3 was followed except that the product of Step 1 above was used in place of 2,4-dibromo-7,7-dimethyl-9-(trifluoromethyl)-7H-benzo[c]fluoren-5-ol; and 1-(4-fluorophenyl)-1-(4-(N-piperidinyl)phenyl)prop-2-yn-1-ol was used in place of 1-(4-methoxyphenyl)-1-(4-butoxyphenyl)prop-2-yn-1-ol. NMR indicated that the product had a structure consistent with 3-(4-fluorophenyl)-3-(4-(N-piperidinyl)phenyl) 5,7-difluoro-10,12-dibromo-13,13-dimethyl-3H,13H-indeno[2',3':3,4]naphtho[1,2-b]pyran represented by the following graphic formula:

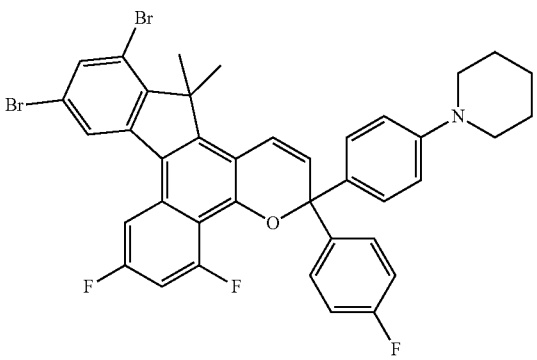 [SMILES: CC1(C)c2c(Br)cc(Br)cc2-c2c1c1c(c3c(F)cc(F)cc23)OC(c2ccc(F)cc2)(c2ccc(N3CCCCC3)cc2)C=C1]

Example 5

Step 1

Magnesium (Mg) turnings (13.5 g, 0.55 mol) were added to a round bottom flask fitted with a condenser and a magnetic stir bar and was kept under $N_2$. 4-Bromo-1,2-dimethoxybenzene [100 g (66.3 mL), 0.46 mol] was added into THF (200 mL); a portion (30 mL) of this solution was added into the Mg turnings. Then dibromoethane (DBE, 1 mL) was added and the flask was put into an ice bath to control the temperature. The rest of the solution of 4-bromo-1,2-dimethoxybenzene was added drop wise into the reaction mixture. After the Mg turnings dissolved, the solution color became light yellow. As the reaction mixture got thicker more THF (100 mL) was added. Then 2,2'-oxybis(N,N-dimethylethanamine) [82 g (98 mL), 0.51 mol] was added drop wise with stirring at 0° C. The mixture was stirred for ~10 minutes. 3,5-Bis(trifluoromethyl) benzoyl chloride [141 g (92.4 mL), 0.51 mol] was diluted with THF (200 mL) and was added drop wise with stirring at 0° C. and white solid formed. After stirring overnight, the reaction mixture was added into ice-water (1.5 L) with 10 wt % NaCl, stirred for 15-20 min. and then acidified to pH ~4 using HCl. The resulting mixture was extracted with ethyl acetate (EtOAc, 1 L) and passed through anhydrous $MgSO_4$ and a silica bed using EtOAc as the eluent. The solvent was evaporated out and the resulting dark thick gummy material (157 g) containing (3,5-bis(trifluoromethyl)phenyl)(3,4-dimethoxyphenyl)methanone was used for the next step.

Step 2

The product of Step 1 (157 g) and dimethyl succinate (80 g, 73 mL) were added to a round bottom flask under $N_2$ that was fitted with an overhead mechanical stirrer. Tetrahydrofuran (1 L) was added. Potassium t-butoxide (52 g) was added over 0.5-1 h to control the temperature of the reaction mixture, which was kept at 15-20° C. in an ice-water bath. After 2 h stirring, the reaction mixture was added into ice-water with 10 wt % NaCl. The whole mixture was stirred for 15-20 min. The top organic layer was separated and the aqueous layer was acidified to pH ~4 using HCl and then extracted with EtOAc and passed through an anhydrous $MgSO_4$ bed. The solvent was evaporated off and the resulting dark thick gummy material (197 g) containing 4-(3,5-bis(trifluoromethyl)phenyl)-4-(3,4-dimethoxyphenyl)-3-(methoxycarbonyl)but-3-enoic acid (mixture of E and Z) was used for the next step.

Step 3

The product of Step 2 (197 g, 0.4 mol) and acetic anhydride [270 g (250 mL), 2.64 mol] were added to a reaction flask containing CH$_2$Cl$_2$ (1 L). Bismuth triflate (18.2 g, 0.028 mol) was added and the reaction mixture was stirred at room temperature for ½ h. The resulting solution was filtered solution and the solvent evaporated to provide a dark colored gummy product. Iso-propanol (0.5 L) wash of the gummy material generated an off-white crystallized product. The product was isolated and dried under vacuum (135 g, 0.26 mol). NMR analysis indicated that the product had a structure consistent with methyl 4-acetoxy-1-(3,5-bis(trifluoromethyl)phenyl)-6,7-dimethoxy-2-naphthoate.

Step 4

The product of Step 3 (135 g) was dissolved in THF (1 L) and the methylmagnesium chloride (MeMgCl) [525 mL (22 wt % in THF), 1.56 mol] was added drop wise with stirring under N$_2$ atmosphere. The reaction mixture was stirred at room temperature for ~3 h and added into ice-water (1.5 L) with 10 wt % NaCl. The whole mixture was stirred for ~15 min, acidified to pH ~3 using HCl and extracted with EtOAc (1 L). The resulting organic layer was separated and washed with NaHCO$_3$ solution (0.5 L) and passed through an anhydrous MgSO$_4$ bed. The solvent was evaporated off and the resulting dark thick gummy material was solidified using MeOH wash. NMR analysis indicated that the product (101 g) had a structure consistent with 4-(3,5-bis(trifluoromethyl)phenyl)-6,7-dimethoxy-3-(prop-1-en-2-yl)naphthalen-1-ol.

Step 5

The product of Step 4 (180 g) and bismuth triflate (13.12 g) were added to xylene (1.8 L) in a round bottom flask equipped with a condenser. The reaction mixture was refluxed with stirring under N$_2$ overnight. The resulting mixture was filtered, solvent evaporated off and passed through a silica gel plug column using EtOAc:Hexanes=1:3 mixture as an eluting solvent. The product was isolated (105 g) after hexane wash. NMR analysis indicated that the product had a structure consistent with 2,3-dimethoxy-7,7-dimethyl-8,10-bis(trifluoromethyl)-7H-benzo[c]fluoren-5-ol.

Step 6

Methylmagnesium bromide 1.4 (M) in toluene/THF (75/25) (860 mL) and 2,6-dimethylpiperidine (40.8 g (50 mL)) were added to a round bottom flask under N$_2$. More THF was added to make the ratio toluene/THF=1/1.2 (v/v) in the rxn mixture maintained at 35° C. The product of Step 5 (108 g) was added in several portions with stirring. The reaction mixture was refluxed overnight, added into ice-water with 10 wt % NaCl and a precipitate formed. After acidifying with 1(N)HCl, the precipitate dissolved at pH~6 and a light brown colored oil formed. The mixture was extracted with EtOAc. The resulting organic layer was separated and washed with NaHCO$_3$ solution, passed through anhydrous MgSO$_4$ bed, dried, and the resulting dark thick gummy material was solidified by using hexanes wash. NMR analysis indicated that the product (64 g) had a structure consistent with 3-methoxy-7,7-dimethyl-8,10-bis(trifluoromethyl)-7H-benzo[c]fluorene-2,5-diol.

Step 7

The product of Step 6 (50 g; 0.11 mol) was added to a reaction flask containing CH$_2$Cl$_2$ (0.5 L) under nitrogen atmosphere with stirring. Pyridine (22 g; 0.28 mol) was added into the reaction mixture and the resulting reaction mixture was cooled using an ice-water bath. Acetyl chloride (19 g; 0.24 mol) was added slowly into the reaction mixture and the reaction temperature was brought to room temperature. After 15 minutes, the solvent was evaporated off and the resulting material was washed with MeOH, dried in a vacuum oven and used for the next step. NMR analysis indicated that the product (55 g) had a structure consistent with 3-methoxy-7,7-dimethyl-8,10-bis(trifluoromethyl)-7H-benzo[c]fluorene-2,5-diyl diacetate.

Step 8

The product from Step 7 (25 g; 0.05 mol) was dissolved into N,N-dimethylformamide (250 mL), and N-chlorosuccinimide (8.01 g; 0.06 mol) was added into the reaction mixture. The reaction mixture was warmed to about 80° C. and stirred. After 30 minutes, the reaction mixture was added into ice cold water, and extracted with EtOAc. The resulting organic layer was separated, dried over anhydrous MgSO$_4$ and filtered. The filtrate was dried and the resulting material was washed with MeOH to obtain a solid (22.4 g). NMR analysis indicated that the product had a structure consistent with 4-chloro-3-methoxy-7,7-dimethyl-8,10-bis(trifluoromethyl)-7H-benzo[c]fluorene-2,5-diyldiacetate.

Step 9

The product of Step 8 (21 g; 0.037 mol) was added to dry THF (200 mL) under nitrogen with stirring in a reaction flask and cooled using an ice-water bath. MeMgCl (3 M solution in THF) (37 mL; 0.112 mol) was added slowly using a syringe. After completion of the reaction the mixture was added to cold water, acidified with HCL to pH ~4, and extracted with EtOAc. The organic portion was collected and dried over anhydrous MgSO4 and solvent was evaporated. Light greenish yellow solid (11.9 g) containing 4-chloro-3-methoxy-7,7-dimethyl-8,10-bis(trifluoromethyl)-7H-benzo[c]fluorene-2,5-diol formed using hexanes as a solvent and was used in the next step as is.

Step 10

The product of Step 9 (3.3 g; 7.0 mmol) was added to CH$_2$Cl$_2$ (100 mL) under nitrogen in a reaction flask. Pyridinium p-toluenesulfonate (0.44 g; 1.75 mmol) and tri-iso-propylorthoformate (2.7 g; 14 mmol) were added to the reaction mixture with stirring. The reaction mixture was heated to ~30° C. and 1,1-bis(4-methoxyphenyl)prop-2-yn-1-ol (1.9 g; 7 mmol) in CH$_2$Cl$_2$ (20 mL) was added slowly to the reaction mixture with stirring. The solution color turned dark and was refluxed for ~2 h. and more 1,1-bis(4-methoxyphenyl)prop-2-yn-1-ol (0.5 g; 1.8 mmol) solution in CH$_2$Cl$_2$ (10 mL) was added and refluxed for another hour. After cooling to room temperature the reaction mixture was passed through a silica gel plug column using CH$_2$Cl$_2$ (100 mL) as an eluting solvent. Then solvent was evaporated off and a quick silica flash column was done using CH$_2$Cl$_2$:Hexane (1:1) as an eluting solvent. The product (2.5 g) was isolated through precipitation from MeOH. NMR analysis indicated that the product had a structure consistent with 3,3-bis(4-methoxyphenyl)-5-chloro-6-methoxy-7-hydroxy-10,12-di(trifluoromethyl)-13,13-dimethyl-3H,13H-indeno[2',3':3,4]naphtho[1,2-b]pyran shown in the following graphic formula:

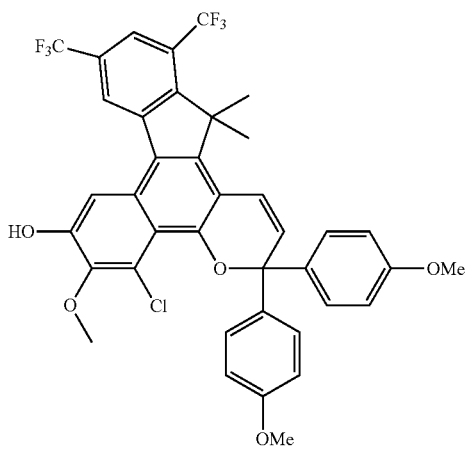 [SMILES: COc1ccc(C2(c3ccc(OC)cc3)C=Cc3c4c(c5cc(O)c(OC)c(Cl)c5c3O2)-c2cc(C(F)(F)F)cc(C(F)(F)F)c2C4(C)C)cc1]

Example 6

The procedure of Example 5 was followed except that in Step 10 1-(4-butoxyphenyl)-1-phenylprop-2-yn-1-ol was used in place of 1,1-bis(4-methoxyphenyl)prop-2-yn-1-ol to make the product. NMR analysis indicated that the product had a structure consistent with 3-(4-butoxyphenyl)-3-phenyl-5-chloro-6-methoxy-7-hydroxy-10,12-di(trifluoromethyl)-13,13-dimethyl-3H,13H-indeno[2',3':3,4]naphtho[1,2-b]pyran shown in the following graphic formula:

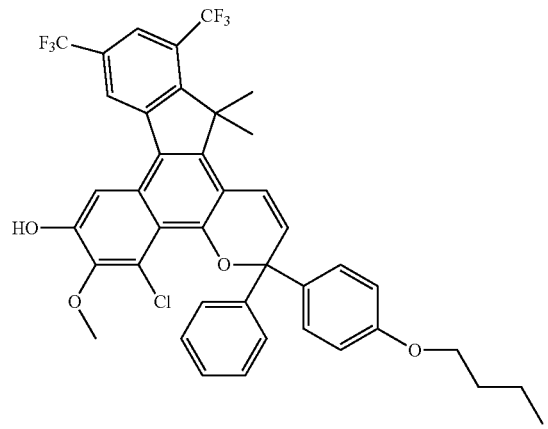 [SMILES: CCCCOc1ccc(C2(c3ccccc3)C=Cc3c4c(c5cc(O)c(OC)c(Cl)c5c3O2)-c2cc(C(F)(F)F)cc(C(F)(F)F)c2C4(C)C)cc1]

Example 7

The procedure of Example 5 was followed except that in Step 10, 1,1-bis(4-butoxyphenyl)prop-2-yn-1-ol was used in place of 1,1-bis(4-methoxyphenyl)prop-2-yn-1-ol to make product. NMR analysis indicated that the product had a structure consistent with 3,3-bis(4-butoxyphenyl)-5-chloro-6-methoxy-7-hydroxy-10,12-di(trifluoromethyl)-13,13-dimethyl-3H,13H-indeno[2',3':3,4]naphtho[1,2-b]pyran shown in the following graphic formula:

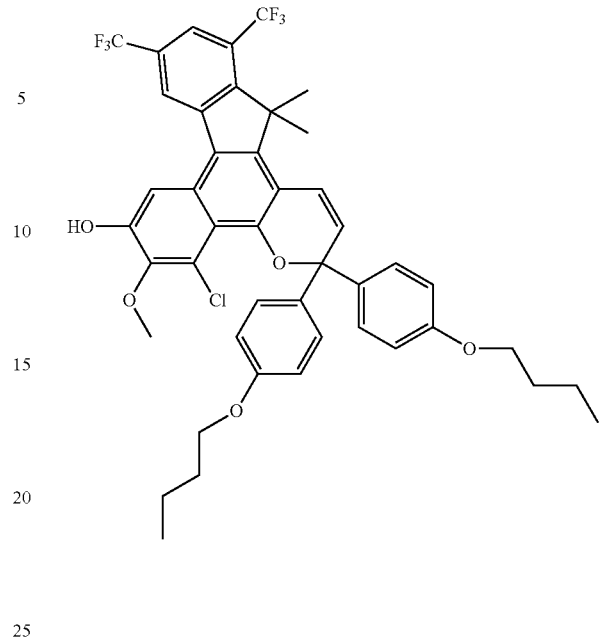

Example 8

Step 1

Magnesium (3.5 g) and THF (20 ml) were placed in a dry flask equipped with a dropping funnel which contained a mixture of 1-bromo-3,5-bis(trifluoromethyl)benzene (35 g) and THF (~100 ml). A portion of the solution in the dropping funnel (10 ml) was added to the flask. A few drops of dibromoethane were also added to the flask and a few minutes later, the contents of the reaction flask started to boil. The rest of the solution in the dropping funnel was added drop wise. Ice water was used occasionally to cool the reaction mixture. After the addition, the mixture was stirred at room temperature for two hours. At 0° C., a solution of bis[2-(N,N-dimethylamino)ethyl]ether (25 ml) in THF (250 ml) was added, stirred for 15 minutes and a solution of 3-bromobenzoyl chloride (25 g) in THF (50 ml) was added in one portion. The resulting mixture was stirred for 3 hours at 0-10° C., and quenched with aqueous ammonium chloride. After extraction of the mixture with EtOAc, the extract was dried over $MgSO_4$ and concentrated. The residue was a oil. The product was purified using a silica gel plug column using EtOAc as the eluent. Viscous oil (41.1 g) was obtained as the product. NMR indicated that the product had a structure consistent with (3,5-bis(trifluoromethyl)phenyl)(3-bromophenyl)methanone.

Step 2

The product from Step 1 (41 g), dimethyl succinate (21 g) and THF (500 ml) were added to a reaction flask equipped with a mechanical stirrer, a solid addition funnel and a nitrogen blanket. The mixture was stirred at room temperature until the solids were dissolved. Solid potassium t-butoxide (15 g) was added through the solid addition funnel and the mixture was stirred at 0° C. After the addition, the mixture was allowed to warm to room temperature and stirred for 4 hours. The resulting reaction mixture was poured into 200 ml of water. Some ethyl acetate was added and the resulting organic layer was separated. The aqueous layer, which contained the product, was collected. The organic layer was extracted with 200 ml water. HCl (2 N) was added to the combined water solution to adjust pH to 5. The resulting mixture was extracted with ethyl acetate, dried over magnesium sulfate, concentrated and dried in vacuum. A high viscosity material was obtained as the product. It was used directly in the next step.

Step 3

To a reaction flask equipped with a condenser containing a solution of the product from Step 2 (23 g) in THF (133 mL) was added a solution of methylmagnesium bromide (24 g) in toluene (140 ml). The mixture was refluxed for 4 hours and then 50 ml of water was added. The mixture was neutralized using 2N HCl, exacted with ethyl acetate, washed with water, concentrated to yield oil (7.1 g) which was used directly in the next step.

Step 4

To a reaction flask containing the product from Step 3 (7.0 g) in Xylene (70 ml) was added Bismuth(III) trifluoromethanesulfonate (Bi(CF$_3$OSO$_2$)$_3$) (0.5 g). After TLC showed that the reaction was completed and it cooled to room temperature, acetic anhydride (5.8 g) was added with mixing and the reaction mixture was refluxed in a reaction flask equipped with a condenser for one hour. After cooling to room temperature, the acetic anhydride was removed by vacuum evaporation and the resulting oil was used directly in the next step.

Step 5

To a reaction flask containing the product of Step 4 (6.1 g) was added methanol (50 mL) and HCl (12 N, 1 ml). The mixture was refluxed for two hours. Methanol was removed by vacuum evaporation. The residue was dissolved in a little methylene chloride, and 40 ml of hexanes was added. After removal of methylene chloride, the suspension was allowed to cool to the room temperature. The solid was collected (2.1 g) and purified by CombiFlash® Rf from Teledyne ISCO to give 2 solids, the first product which weighed 295 mg and a second product of 197 mg in weight.

Step 6

To a reaction flask containing the first product (295 mg) from Step 5 was added 1,1-bis(4-fluorophenyl)prop-2-yn-1-ol 1 (150 mg) and a few crystals of p-toluenesulfonic acid. The mixture was stirred at room temperature for one hour. The product was purified using a CombiFlash® Rf from Teledyne ISCO followed by recrystallization from methanol. Crystals were obtained as the product (295 mg). NMR analysis indicated that the product had a structure consistent with 3,3-bis(4-fluorophenyl)-5,7-di(trifluoromethyl)-12-bromo-13,13-dimethyl-3H,13H-indeno[2',3':3,4]naphtho[1,2-b]pyran represented by the following graphic formula:

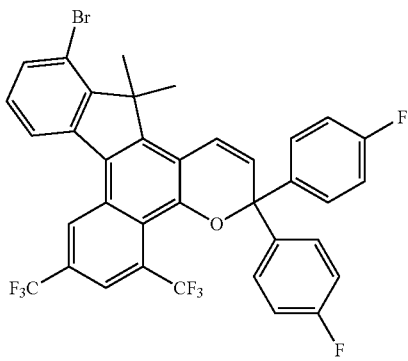 [SMILES: CC1(C)c2c(Br)cccc2-c2c1c1c(c3c(C(F)(F)F)cc(C(F)(F)F)cc23)OC(c2ccc(F)cc2)(c2ccc(F)cc2)C=C1]

Example 9

Step 1

The procedure from Step 6 of Example 8 was followed except that the second product (197 mg) of Step 5 of Example 8 was used in place of the first product. Crystals were obtained as the product. NMR analysis indicated that the product had a structure consistent with 3,3-bis(4-fluorophenyl)-5,7-di(trifluoromethyl)-10-bromo-13,13-dimethyl-3H, 13H-indeno[2',3':3,4]naphtho[1,2-b]pyran represented by the following graphic formula:

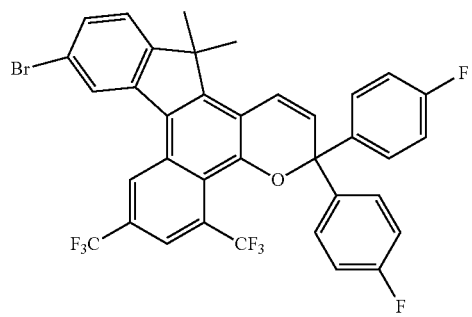 [SMILES: CC1(C)c2ccc(Br)cc2-c2c1c1c(c3c(C(F)(F)F)cc(C(F)(F)F)cc23)OC(c2ccc(F)cc2)(c2ccc(F)cc2)C=C1]

Example 10

Step 1

Phenylmagnesium bromide/diethyl ether (3M, 100 mL) solution was added to a 2 L two-neck reaction flask equipped with an additional funnel and magnetic stirrer in an ice bath. Tetramethyl ethylene diamine (58 ml)/THF (100 ml) was added to the flask slowly. The mixture was stirred for 1 hour. 3,4,5-Trimethoxybenzoyl chloride (69 g)/THF (200 ml) was dropped to the flask over 30 minutes. The cooling bath was removed 1 hour after the addition. The resulting mixture was stirred at room temperature overnight. The resulting yellow cloudy mixture was poured into ice water (1 L). Concentrated HCl (37%, 200 mL) was added to the mixture slowly. The resulting mixture was extracted with ethyl acetate twice (400+200 mL). The top layers were recovered, washed with water and brine. The organic solutions were combined and dried over Na$_2$SO$_4$. Part of the ethyl acetate was stripped off and hexane was added to the concentrated solution. Solid product containing 3,4,5-trimethoxybenzophenone was precipitated out and recovered by filteration (74 g).

Step 2

The product from Step 1 (74 g), potassium t-butoxide (69 g) and toluene (900 mL) were added to a 2 L three-neck reaction flask equipped with a mechanical stirrer under a nitrogen blanket. Dimethyl succinate (70 g) in toluene (100 mL) was added to the flask through an addition funnel and the resulting mixture was stirred at room temperature for 20 hours. The reaction mixture was poured into 600 mL of water. The bottom aqueous layer, which contained the product, was collected. HCl (12 N, 50 mL) was added to the water solution and yellow oil precipitated. The resulting mixture was extracted with ethyl acetate (800 mL). The top organic layer was recovered, washed with water and brine, then dried over sodium sulfate, concentrated and dried in vacuum. Yellow glassy oil (112 g) was obtained as product. Mass spectroscopy indicated the desired molecular weight of 368. The product was used in the next step without further purification.

Step 3

The product of Step 2 (112 g) was dissolved in acetic anhydride (150 mL) in a single-neck 1 L reaction flask equipped with a condenser. The mixture was heated under refluxing condition for 15 hours. The acetic anhydride was removed by vacuum evaporation and 152 grams of oil was obtained as the product. It was used in the next step without further purification.

Step 4

To a 1 L reaction flask containing the 150 grams of the product from Step 3 was added methanol (500 mL) and HCl (12 N, 5 mL). The mixture was heated under refluxing condition for 5 hours. Methanol was removed by vacuum evaporation. The residue oil was purified by chromatography to provide 107 grams of oily product. Solid product (70 g) that precipitated out from the oily mixture was dried. Mass spectroscopy indicated the desired molecular weight of 368.

Step 5

The product (35 g) from Step 4 was dissolved in 500 mL of anhydrous tetrahydrofuran (THF) in an oven dried flask equipped with addition funnel and magnetic stir bar. The flask was seated in ice bath, and methyl magnesium chloride in a THF solution (3 M, 180 mL) was added dropwise. After the addition, the mixture was heated under refluxing for 2 hours. The reaction mixture was cooled to room temperature and poured into 400 mL of ice water. The mixture was acidified by HCl (12 N, 70 mL). The resulting mixture was extracted with ethyl acetate twice (400+200 mL). The top organic layers were recovered, combined, dried over sodium sulfate, concentrated and dried in vacuum. The product (35 g of oil) was used in the next step without further purification.

Step 6

The product from Step 5 (35 g) and xylene (80 mL) were added to a 500 mL reaction flask equipped with Dean-Stark trap, water condenser and a magnetic stir bar. Bismuth(III) trifluoromethanesulfonate (0.1 g) was added and the resulting mixture was heated under refluxing for 4 hours. The reaction mixture was concentrated and the residue was filtered through a silica gel plug using ethyl acetate and hexanes as eluent. The product (30 g) was obtained as off-yellow oil. The product was used in the next step without further purification.

Step 7

The product from Step 6 (5 g) and dodecyl benzene sulfonic acid (1 drop) was dissolved in $CHCl_3$ (50 mL) in a 250 mL reaction flask. To the flask was added 1-phenyl-1-(4-morpholinophenyl)prop-2-yn-1-ol (4.5 g). The mixture was heated under refluxing for 2 hours. The reaction mixture was purified by chromatography. Two solid products were isolated. NMR analysis indicated that the desired product had a structure consistent with 3-phenyl-3-(4-morpholinophenyl)-5,6,7-trimethoxy-13,13-dimethyl-3H,13H-indeno[2,1-f]naphtho[1,2-b]pyran represented by the following graphic formula:

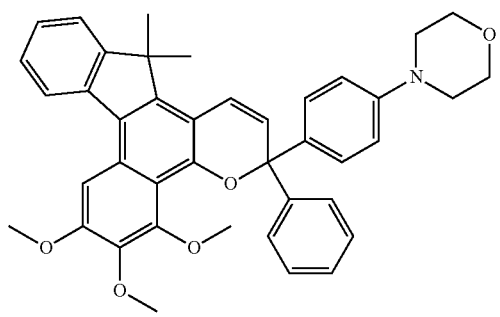 [SMILES: COc1cc2c3c(c4c(c2c(OC)c1OC)OC(c1ccccc1)(c1ccc(N2CCOCC2)cc1)C=C4)C(C)(C)c1ccccc1-3]

Example 11

Step 1

To a single-neck flask with 3,5-bistrifluoromethylphenyl magnesium bromide (76 g, made in situ) in anhydrous THF (200 mL)/diethyl Ether (100 mL) seated in an ice bath, was added tetramethylethylene diamine (47 mL)/anhydrous THF solution (50 mL) over 15 minutes. The reaction mixture was stirred for 30 minutes. 3,4,5-Trimethoxy benzoyl chloride (55 g)/anhydrous THF (150 mL) solution was added to the flask over 10 minutes. The ice bath was removed upon completion of the addition. The resulting mixture was stirred at room temperature overnight. The resulting brown mixture was poured into ice water (400 mL). Concentrated HCl (37%, 50 mL) was added to the mixture slowly. The resulting mixture was extracted with ethyl acetate twice (400+200 mL). The top layer was recovered, washed with brine (150 mL), and dried over $Na_2SO_4$ and solvent was stripped off under vacuum. The residue was filtered through a short silica gel plug using ethyl acetate and hexanes as eluent. Off-yellow solid product (80 g) containing 3,5-bistrifluoromethyl-3',4',5'-trimethoxybenzophenone was obtained from the major fraction.

Step 2

The product from Step 1 (80 g) and potassium t-butoxide (26 g) were dissolved in anhydrous THF (400 mL) in a 1 L three-neck reaction flask equipped with a mechanical stirrer under a nitrogen blanket. Dimethyl succinate (34 mL) was added to the flask through addition funnel slowly. The resulting mixture was stirred at room temperature for 20 hours and the reaction mixture was poured into 400 mL of water. The bottom aqueous layer, which contained the product, was collected. HCl (12 N, 60 mL) was added to the water solution and yellow oil precipitated. The resulting mixture was extracted with ethyl acetate twice (250+250 mL). The top organic layer was washed with brine, then dried over sodium sulfate, concentrated and dried in vacuum. Yellow glassy oil (80 g) was obtained as product. The product was used in the next step without further purification.

Step 3

The product of Step 2 (80 g) was dissolved in acetic anhydride (200 mL) in a single-neck 1 L reaction flask equipped with a condenser. The mixture was heated under refluxing for 5 hours. The acetic anhydride was removed by vacuum evaporation. The product was filtered through a short silica gel plug using ethyl acetate and hexanes as eluent. The major fraction was condensed to an oily product (85 g). It was used in the next step without further purification.

Step 4

To a 1 L single-neck flask containing the product from Step 3 was added to methanol (400 mL) and HCl (12 N, 10 mL). The mixture was heated under refluxing for 5 hours. Methanol was removed by vacuum evaporation. The product was filtered through a short silica gel plug using ethyl acetate and hexanes as eluent. The major fraction was condensed to yield an oily product (70 g). It was used in the next step without further purification.

Step 5

To a 2 L oven dried flask equipped with addition funnel and magnetic stir bar, was added the product (70 g) from Step 4 in 200 mL of anhydrous THF. The flask was seated in an ice bath. A solution of methyl magnesium chloride (3 M) in THF (230 mL) was added to the flask dropwise. The ice bath was removed upon the addition. The mixture was heated under refluxing for 1 hour. The reaction mixture was cooled to room temperature and poured into ice water (1 L). The mixture was acidified by HCl (12 N, 70 mL). The resulting mixture was extracted with ethyl acetate twice (300+200 mL). The top organic layers were combined, washed with brine, dried over sodium sulfate, concentrated and dried in vacuum. The product (65 g of oil) was used in the next step without further purification.

Step 6

The product from Step 5 (65 g) and xylene (200 mL) were added to a 500 mL reaction flask equipped with Dean-Stark trap, water condenser and a magnetic stir bar. Bismuth trifluoromethyl sulfonamate (0.9 g) was added and the resulting mixture was heated under refluxing for 20 hours. The reaction mixture was concentrated and the residue was filtered through a silica gel plug using ethyl acetate and hexanes as eluent. The product (30 g) was obtained as an off-yellow oil. The product was used in next step without further purification.

Step 7

The product from Step 6 (8 g), bismuth trifluoromethyl sulfonamate (0.4 g) and trimethylorthoformate (5 mL) were dissolved in dichloroethane (ClCH$_2$CH$_2$Cl) (30 mL) in a 250 mL reaction flask. To the flask was added 1-phenyl-1-(4-morpholinophenyl)prop-2-yn-1-ol (5 g). The mixture was heated under refluxing for 20 hours. The reaction mixture was purified by silica gel chromatography using a mixture of ethyl acetate/hexanes). Solid product (2 g) was obtained from the major fraction. NMR analysis indicated that the product had a structure consistent with 3-phenyl-3-(4-morpholinophenyl)-5,6,7-trimethoxy-10,12-di(trifluoromethyl)-13,13-dimethyl-3H,13H-indeno[2,1-f]naphtho[1,2-b]pyran represented by the following graphic formula:

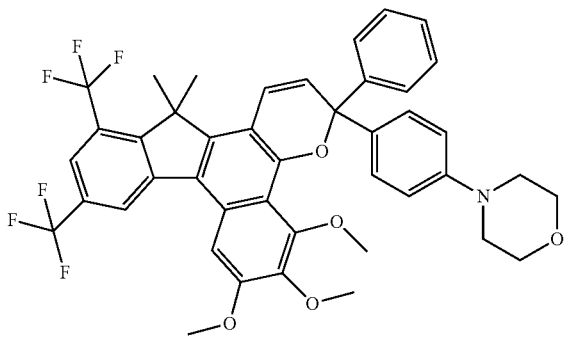 [SMILES: COc1cc2c3c(c4c(c2c(OC)c1OC)OC(c1ccccc1)(c1ccc(N2CCOCC2)cc1)C=C4)C(C)(C)c1c-3cc(C(F)(F)F)cc1C(F)(F)F]

Example 12

Step 1

In an oven-dried flask placed under a nitrogen atmosphere, 3-anisoyl chloride (195 g) and biphenyl (190 g) were stirred in dichloromethane (1.4 L). The flask was placed in an ice bath and to it was added anhydrous aluminum chloride (172 g) in portions, each spaced 10 minutes apart. After the aluminum chloride addition was complete the reaction mixture was heated to reflux for 2 hours. After cooling to room temperature, the reaction mixture was slowly poured into a beaker containing a 10% aqueous solution of hydrochloric acid (1.5 L) and ice while stirring vigorously. A separatory funnel was used to separate the organic and aqueous layers. The recovered organic layer was then washed with deionized water three times with 1 liter each time, hereinafter designated as (3×1 L), dried over sodium sulfate and concentrated by rotary evaporation. Crystals formed while sitting overnight and were collected by vacuum filtration. A recrystallization was then performed by dissolving the crystals in a solution of 10% methanol/90% dichloromethane and subsequently removing nearly all of the solvent by rotary evaporation. Crystals formed while sitting overnight and were collected by vacuum filtration yielding 153 g of [1,1'-biphenyl]-4-yl(3-methoxyphenyl)methanone.

Step 2

In an oven-dried flask placed under a nitrogen atmosphere, the product of Step 1 (153 g) and potassium tert-butoxide (95.3 g) were stirred in toluene (1850 mL) using a mechanical stirrer. To this was added dimethyl succinate (120 mL) via addition funnel slowly over a 1 hour period of time. The reaction mixture was then heated to 40° C. for 2 hours. It was cooled to room temperature and then slowly poured into a beaker containing deionized water (2 L) and ice while stirring vigorously. Concentrated hydrochloric acid was slowly added to the mixture while stirring until pH 1 was reached. A separatory funnel was used to separate the organic and aqueous layers. The aqueous layer was extracted with ethyl acetate (2×1 L). The organic layers were combined, washed with deionized water (2×1 L), dried over magnesium sulfate and concentrated by rotary evaporation to yield an amber colored oil containing a mixture of (E and Z) 4-([1,1'-biphenyl]-4-yl)-3-methoxycarbonyl-4-(3-methoxyphenyl)but-3-enoic acid (260 g) which was used in the next reaction as is.

Step 3

The product of Step 2 (214 g) was stirred in a flask containing acetic anhydride (856 mL). The reaction mixture was heated to reflux for 3 hours. After cooling to room temperature, the acetic anhydride was subsequently removed via rotary evaporation. A dark reddish-brown oil (300 g) was isolated which contained a mixture of 3 isomers: methyl 1-([1,1'-biphenyl]-4-yl)-4-acetoxy-7-methoxy-2-naphthoate and methyl 1-([1,1'-biphenyl]-4-yl)-4-acetoxy-5-methoxy-2-naphthoate and methyl-4-acetoxy-1-(3-methoxyphenyl)-6-phenyl-2-naphthoate, and was used in the next reaction as is.

Step 4

The product from Step 3 was added to an oven-dried flask placed under a nitrogen atmosphere and stirred in methanol (1100 mL). To this was added concentrated hydrochloric acid (20 mL). The reaction mixture was heated to reflux for 4 hours and then cooled to room temperature. It was then partially concentrated by rotary evaporation, diluted with methylene chloride (1.5 L), washed with deionized water (2×1 L) followed by a saturated aqueous solution of sodium bicarbonate (750 mL), dried over sodium sulfate and concentrated by rotary evaporation. The resulting residue was divided in half and each portion was chromatographed on silica gel (1100 g) eluting with a solution of 25% ethyl acetate/75% hexanes. Fractions containing the isomer that eluted first were combined and concentrated by rotary evaporation. The resulting product weighed 23 g. NMR analysis indicated that the product has a structure consistent with 1-([1,1'-biphenyl]-4-yl)-4-hydroxy-5-methoxy-2-naphthoate.

Step 5

In an oven-dried flask placed under a nitrogen atmosphere, the product of Step 4 (23 g) was stirred in anhydrous tetrahydrofuran (230 mL). The flask was placed in an ice bath, and to it was added a 3.0M solution of methylmagnesium chloride in anhydrous tetrahydrofuran (120 mL) slowly drop-wise using an addition funnel over a 45 minute period. The reaction mixture was heated to reflux for 2 hours and then cooled to room temperature. It was then slowly poured into a beaker containing a saturated aqueous solution of ammonium chloride (600 mL) and ice while stirring. A separatory funnel was used to separate the aqueous and organic layers. The recovered aqueous layer was extracted with ethyl acetate (2×250 mL). The resulting organic layers were combined and washed with a saturated aqueous solution of sodium bicarbonate (600 mL), dried over sodium sulfate and concentrated by rotary evaporation to yield a solid. The solid was slurried in a minimal amount of methyl tert-butyl ether and collected by vacuum filtration yielding 20 g of 4-([1,1'-biphenyl]-4-yl)-3-(2-hydroxypropan-2-yl)-8-methoxynaphthalen-1-ol.

Step 6

In an oven-dried flask placed under a nitrogen atmosphere and equipped with a Dean-Stark trap, the product of Step 5 (20 g) was stirred in xylenes (300 mL). To this was added p-toluenesulfonic acid (990 mg). The reaction mixture was heated to reflux for 3 hours and then cooled to room temperature. It was transferred to a separatory funnel and washed with saturated aqueous solution of sodium bicarbonate (300 mL), dried over sodium sulfate and then concentrated by rotary evaporation to yield a solid. The solid was slurried in a minimal amount of methyl tert-butyl ether and collected by vacuum filtration yielding 12 g of 4-methoxy-7,7-dimethyl-9-phenyl-7H-benzo[C]fluoren-5-ol.

Step 7

The product from Step 6 (0.5 g), dodecylbenzene sulfonic acid (0.1 g) and 1-(4-methoxyphenyl-1-(4-morpholinophenyl)prop-2-yn-1-ol (0.9 g) were dissolved in xylene (10 mL) in a 50 mL reaction flask. The mixture was heated under refluxing for 2 hours. The reaction mixture was purified by silica gel chromatography using a mixture of ethyl acetate/hexanes as eluent. Off white solid product (100 mg) was recrystallized from the major fraction. NMR analysis indicated that the products had a structure consistent with 3-(4-methoxyphenyl)-3-(4-morpholinophenyl)-5-methoxy-11-phenyl-13,13-dimethyl-3H,13H-indeno[2,1-f]naphtho[1,2-b]pyran represented by the following graphic formula:

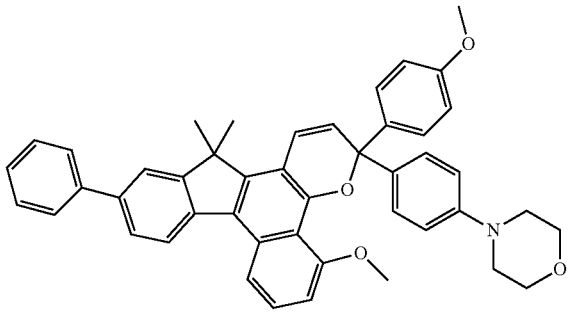 [SMILES: COc1ccc(C2(c3ccc(N4CCOCC4)cc3)C=Cc3c4c(c5cccc(OC)c5c3O2)-c2ccc(-c3ccccc3)cc2C4(C)C)cc1]

Example 13

The procedure of Step 1-6 of Example 12 were followed except that in Step 7, the product of Step 6 (5 g) of Example 12 was added with stirring to an oven-dried flask placed under a nitrogen atmosphere containing 1,2-dichloroethane (60 mL). To this was added trimethylorthoformate (4.4 g) and pyridinium p-toluene sulfonate (1.03 g). The reaction mixture was then heated to reflux. 1,1-Bis-(4-methoxyphenyl)-2-propyn-1-ol, (4.8 g) dissolved in 1,2-dichloroethane (40 mL) was very slowly added to the reaction mixture drop-wise using an addition funnel over 2 hours. After the addition was completed, additional 1,1-bis-(4-methoxyphenyl)-2-propyn-1-ol (4.8 g) dissolved in 1,2-dichloroethane (40 mL), was charged to the addition funnel and added to the reaction mixture slowly drop-wise over 2 hours. The reaction mixture was cooled to room temperature, transferred to a separatory funnel, washed with a saturated aqueous solution of sodium bicarbonate (100 mL), dried over sodium sulfate and concentrated by rotary evaporation. The resulting residue was purified by column chromatography on silica gel (400 g) eluting with a solution of 20% ethyl acetate/80% hexanes. Fractions containing product were combined and concentrated by rotary evaporation. The resulting residue was dissolved in diethyl ether and subsequently crystallization occurred. The crystals were collected by vacuum filtration and weighed 0.9 grams. NMR analysis showed that the product has a structure consistent with 3,3-bis-(4-methoxyphenyl)-5-methoxy-11- phenyl-13,13-dimethyl-3H,13H-indeno[2',3':3,4]naphtho[1,2-b]pyran shown in the following graphic formula:

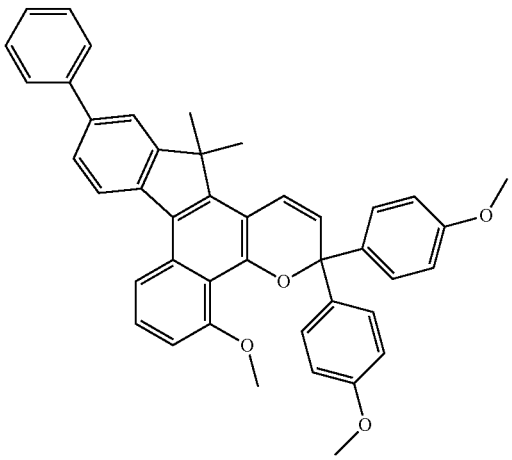 [SMILES: COc1ccc(C2(c3ccc(OC)cc3)C=Cc3c4c(c5cccc(OC)c5c3O2)-c2ccc(-c3ccccc3)cc2C4(C)C)cc1]

Example 14

Step 1

To a single-neck flask with 3,5-bisifluorophenyl magnesium bromide (45 g, made in situ) in anhydrous diethyl Ether (300 mL) seated in ice bath, was added tetramethylethylene diamine (36 mL)/anhydrous THF solution (50 mL) over 10 minutes. The reaction mixture was stirred for 30 minutes. 3,4,5-Trimethoxybenzoyl chloride (43 g) in anhydrous THF (150 mL) solution was added to flask over 10 minutes. The ice bath was removed upon the completion of addition. The resulting mixture was stirred at room temperature for 1 hour. The resulting brown mixture was poured into ice water (300 mL). Concentrated HCl (12N, 50 mL) was added to the mixture slowly. The top layer was recovered, washed with brine (150 mL), and dried over $Na_2SO_4$. Solvent was stripped off under vacuum. Off-yellow solid product (40 g) containing 3,5-bisfluoro-3',4',5'-trimethoxybenzophenone was recrystallized from the original product.

Step 2

The product from Step 1 (40 g) and potassium t-butoxide (20 g) were dissolved in anhydrous toluene (150 mL) in a 1 L three-neck reaction flask equipped with a mechanical stirrer under a nitrogen blanket. Dimethyl succinate (21 mL) was added slowly to the flask through the addition funnel. The resulting mixture was stirred at room temperature for 1 hour and was poured into water (200 mL). The bottom aqueous layer, which contained the product, was collected. HCl (12 N, 50 mL) was added to the water solution. Yellow oil precipitated. The resulting mixture was extracted with ethyl acetate (300 mL). The top organic layer was recovered, dried over sodium sulfate and concentrated (54 g). The resulting yellow glassy oil product was used in the next step without further purification.

Step 3

The product of Step 2 (54 g) was dissolved in acetic anhydride (80 mL) in a single-neck 1 L reaction flask equipped with a condenser. The mixture was heated under refluxing for 16 hours. The acetic anhydride was removed by vacuum evaporation. The resulting residue was dissolved in methanol (300 mL). Solid product (28 g) was recrystallized. NMR analysis indicated the desired product was in the mother liquor. The mother liquor was filtered through a short silica gel plug using ethyl acetate and hexanes as eluent. The major fraction was condensed to an oily product (18 g). It was used in the next step without further purification.

Step 4

To a 2 L oven dried flask equipped with addition funnel and magnetic stir bar, was added the product from Step 3 (18 g) in anhydrous THF (50 mL). The flask was seated in an ice bath. A 3 M solution of methyl magnesium chloride in THF (100 mL) was added to the flask drop wise. The ice bath was removed upon the addition. The mixture was stirred at room temperature for 2 hours. The reaction mixture was poured into ice water (400 mL). The mixture was acidified by HCl (12 N, 50 mL). The resulting mixture was extracted with ethyl acetate twice (200+100 mL). The top organic layers were recovered, combined, washed with brine (100 mL), dried over sodium sulfate, concentrated and dried in vacuum. The product (25 g of oil) was used in the next step without further purification.

Step 5

The product from Step 4 (25 g) and xylene (200 mL) were added to a 500 mL reaction flask equipped with Dean-Stark trap, water condenser and a magnetic stir bar. Bismuth trifluoromethyl sulfonate (0.1 g) was added and the resulting mixture was heated under refluxing for 3 hours. The reaction mixture was concentrated and the residue was filtered through a silica gel plug using ethyl acetate and hexanes as eluent. The product (20 g) was obtained as off-yellow oil. The product was used in next step without further purification.

Step 6

The product from Step 5 (2 g), dodecylbenzene sulfonic acid (0.1 g) and 1-(4-methoxyphenyl)-1'-(4-morpholinophenyl)prop-2-yn-1-ol (1 g) were dissolved in $ClCH_2CH_2Cl$ (30 mL) in a 250 mL reaction flask. The mixture was heated under refluxing for 1 hour. The reaction mixture was purified by silica gel chromatography using a mixture of ethyl acetate/hexanes as eluent. Solid product (2 g) was obtained from the major fraction recovered. NMR analysis indicated that the product had a structure consistent with 3-(4-methoxyphenyl)-3-(4-morpholinophenyl)-5,6,7-trimethoxy-10,12-di(fluoro)-13,13-dimethyl-3H,13H-indeno[2,1-f]naphtho[1,2-b]pyran represented by the following graphic formula:

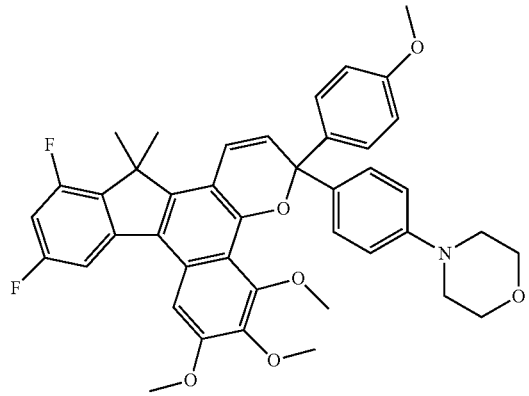 [SMILES: COc1ccc(C2(c3ccc(N4CCOCC4)cc3)C=Cc3c4c(c5cc(OC)c(OC)c(OC)c5c3O2)-c2cc(F)cc(F)c2C4(C)C)cc1]

Example 15

Step 1

To a single-neck flask with [1,1'-biphenyl]-4-ylmagnesium bromide (54 g, made in situ) in anhydrous THF (250 mL)/diethyl ether (300 mL) seated in an ice bath, was added tetramethylethylene diamine (40 mL)/anhydrous THF solution (50 mL) over 10 minutes. The reaction mixture was stirred for 30 minutes. 3, 4, 5-Trimethoxybenzoyl chloride (48 g)/anhydrous THF (150 mL) solution was added to flask over 30 minutes. The ice bath was removed upon the completion of the addition. The resulting mixture was heated under refluxing for 3 hours. The resulting brown mixture was poured into ice water (300 mL). HCl (12N, 50 mL) was added to the mixture slowly. The top layer was recovered, filtered, dried over magnesium sulfate and solvent was stripped off under vacuum. The product (77 g) containing 4-phenyl-3',4', 5'-trimethoxybenzophenone was used in the next step without further purification.

Step 2

The product from Step 1 (77 g) and dimethyl succinate (21 mL) were dissolved in anhydrous toluene (1 L) in a 2 L three-neck reaction flask equipped with a mechanical stirrer under a nitrogen blanket. Potassium t-butoxide (27 g) was added to the flask through addition funnel slowly. The resulting mixture was stirred at room temperature for 2 hours and poured into water (300 mL). The bottom aqueous layer, which contained the product, was collected. HCl (12 N, 100 mL) was added to the water solution. The resulting mixture was extracted with ethyl acetate (500 mL). The top organic layer was recovered, filtered over magnesium sulfate and concentrated to produce a yellow glassy oil (60 g). The product was used in the next step without further purification.

Step 3

The product of Step 2 (60 g) was dissolved in acetic anhydride (200 mL) in a single-neck 1 L reaction flask equipped with a condenser. The mixture was heated under refluxing for 8 hours. The acetic anhydride was removed by vacuum evaporation. The residue was filtered through a short silica gel plug using ethyl acetate and hexanes as eluent. One major fraction was collected. A first solid product (25 g) was recrystallized from the residue and a second solid (25 g) was recrystallized from the mother liquor. NMR analysis indicated that the structure of the second solid was consistent with 2,3,4-trimethoxy-9-phenyl-7,7-dimethyl-7H-benzo[c]fluoren-5-ol.

Step 4

To a 1 L oven dried single-neck flask equipped with addition funnel and magnetic stir bar, was added 2 M THF solution of ethyl magnesium chloride (260 mL). The second solid product obtained from Step 3 (25 g) in anhydrous THF (350 mL) was dropped to the flask in 15 minutes. The mixture was stirred at room temperature for 3 hours. The reaction mixture was poured into ice water (200 mL) and acidified by HCl (12 N, 50 mL). The resulting mixture was extracted with ethyl acetate (200 mL). The top organic layer was recovered, filtered over magnesium sulfate, concentrated and dried in vacuum. The product (25 g of oil) was used in the next step without further purification.

Step 5

The product from Step 4 (25 g) and cumene (100 mL) were added to a 250 mL reaction flask equipped with Dean-Stark trap, water condenser and a magnetic stir bar. Pyridinium p-toluene sulfonate (2 g) was added and the resulting mixture was heated under refluxing for 3 hours. The reaction mixture was concentrated and the residue was filtered through a silica gel plug using ethyl acetate and hexanes as eluent. The product (20 g) was obtained as off-yellow oil. The product was used in next step without further purification.

Step 6

The product from Step 5 (3 g), bismuth(III) trifluoromethanesulfonate (0.1 g) and 1-(4-methoxyphenyl)-1'-(4-morpholinophenyl)prop-2-yn-1-ol (2.5 g) were dissolved in toluene (30 mL) in a 250 mL reaction flask. The mixture was heated to 80° C. for 3 days. The reaction mixture was purified by silica gel chromatography using a mixture of ethyl acetate/hexanes as eluent. Solid product (2 g) was recrystallized from the major fraction recovered. NMR analysis indicated that the product had a structure consistent with 3-(4-methoxyphenyl)-3-(4-morpholinophenyl)-5,6,7-trimethoxy-11-phenyl-13, 13-diethyl-3H,13H-indeno[2,1-f]naphtho[1,2-b]pyran represented by the following graphic formula:

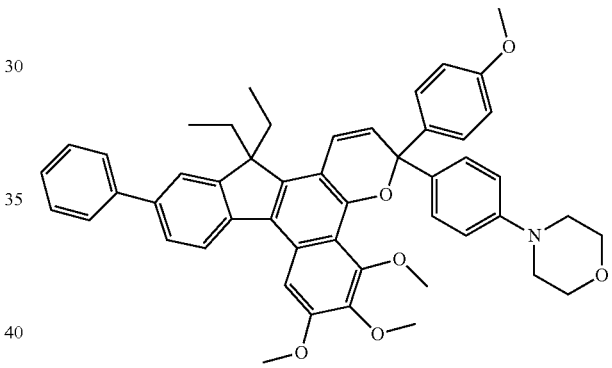

Example 16

Step 1

The procedure from Step 1 of Example 1 was followed except that: 1-bromo-3,5-difluorobenzene was used instead of tribromobenzene and 4-methoxybenzoyl carbonyl chloride was used in place of benzoyl chloride to provide a product with mass spectrum corresponding the structure of 3,5-difluoro-4'-methoxybenzophenone.

Step 2

The procedures from Step 2 to Step 5 of Example 3 were followed except that the product from Step 1 above was used instead of 3,5-dibromo-4'-trifluoromethylbenzophenone to provide a product with NMR analysis corresponding to the structure of 2,4-difluoro-9-methoxy-7,7-dimethyl-7H-benzo[c]fluoren-5-ol.

Step 3

The procedure from Step 6 of Example 3 was followed except that product from Step 2 above was used instead of 2,4-dibromo-7,7-dimethyl-9-(trifluoromethyl)-7H-benzo[c]fluoren-5-ol and 1-(4-fluorophenyl)-1-phenyl-prop-2-yn-1-ol was used in place of 1-(4-butoxyphenyl)-1-(4-methoxyphenyl)prop-2-yn-1-ol. NMR analysis indicated that the product had a structure consistent with 3-(4-fluorophenyl)-3-phenyl-5,7-difluoro-11-methoxy-13,13-dimethyl-3H,13H-indeno[2',3':3,4]naphtho[1,2-b]pyran represented by the following graphic formula:

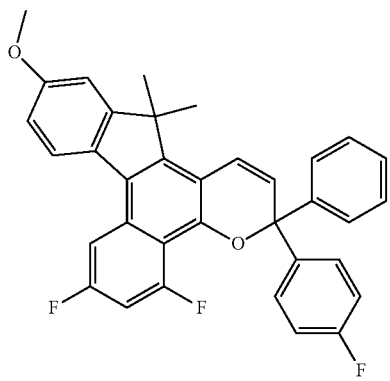 [SMILES: COc1ccc2c(c1)C(C)(C)c1c3c(c4c(F)cc(F)cc4c1-2)OC(c1ccccc1)(c1ccc(F)cc1)C=C3]

Example 17

The procedure from Step 3 of Example 16 was followed except that 1-(4-butoxyphenyl)-1-(4-methoxyphenyl)prop-2-yn-1-ol was used in place of 1-(4-fluorophenyl)-1-phenyl-prop-2-yn-1-ol. NMR analysis indicated that the product had a structure consistent with 3-(4-methoxyphenyl)-3-phenyl-5,7-difluoro-11-methoxy-13,13-dimethyl-3H,13H-indeno[2',3':3,4]naphtho[1,2-b]pyran represented by the following graphic formula:

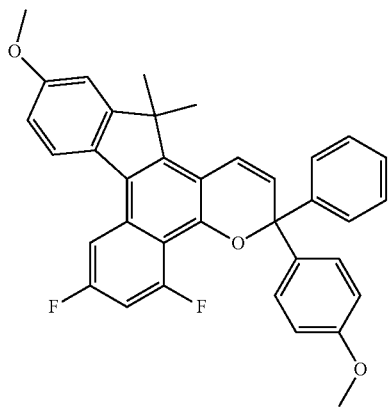 [SMILES: COc1ccc(C2(c3ccccc3)C=Cc3c4c(c5cc(F)cc(F)c5c3O2)-c2ccc(OC)cc2C4(C)C)cc1]

Example 18

The procedure from Step 3 of Example 16 was followed except that 1-(4-methoxyphenyl)-1-phenyl-prop-2-yn-1-ol was used in place of 1-(4-fluorophenyl)-1-phenyl-prop-2-yn-1-ol. NMR analysis indicated that the product had a structure consistent with 3-(4-butoxyphenyl)-3-(4-methoxyphenyl)-5,7-difluoro-11-methoxy-13,13-dimethyl-3H,13H-indeno[2',3':3,4]naphtho[1,2-b]pyran as represented by the following graphic formula:

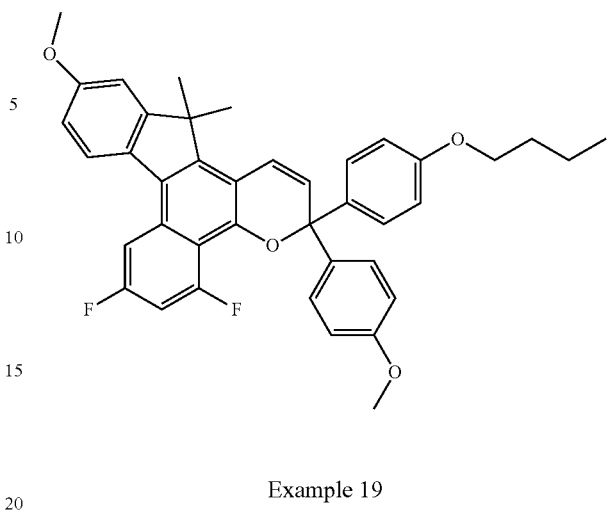

Example 19

The product of Example 17 (0.5 g) was dissolved in THF (40 mL) and 4 mL of 0.5M sodium methoxide (NaOMe) in MeOH were added. After refluxing for 12 h the solvents were evaporated and the residue purified by column chromatography using 1:10 hexane methylene chloride mixtures as the eluent. Fractions containing the desired material were grouped and concentrated (0.3 g). NMR and Mass spectrum analysis of the solid indicated a structure that was consistent with 3-phenyl-3-(4-methoxyphenyl)-5-methoxy-7-fluoro-11-methoxy-13,13-dimethyl-3H,13H-indeno[2',3':3,4]naphtho[1,2-b]pyran represented by the following graphic formula:

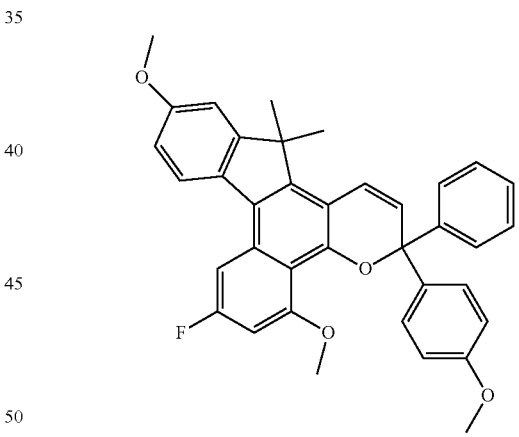

Example 20

In a dried flask, morpholine (2.3 mL) was dissolved in dry THF (4 mL) and then n-BuLi was slowly added using a syringe (addition time 0.5 min). After 2 minutes the product of Example 17 (0.7 g) was dissolved in dry THF (10 mL) and added to the reaction mixture. After 5 min, the reaction was quenched with saturated NH$_4$Cl (50 mL) and extracted with ethyl acetate. The residue was purified by column chromatography using 1:1 methylene chloride ethyl acetate mixtures as the eluent. Fractions containing the desired material were grouped and concentrated (0.5 g). NMR and Mass spectrum analysis of the solid indicated a structure that was consistent with 3-phenyl-3-(4-methoxyphenyl)-5,7-dimorpholino-11- methoxy 13,13-dimethyl-3H,13H-indeno[2',3':3,4]naphtho[1,2-b]pyran represented by the following graphic formula:

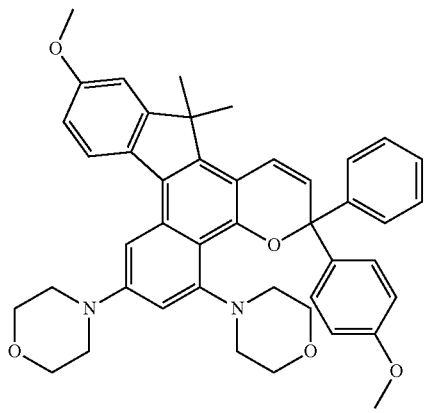 [SMILES: COc1ccc(C2(c3ccccc3)C=Cc3c4c(c5cc(N6CCOCC6)cc(N6CCOCC6)c5c3O2)-c2ccc(OC)cc2C4(C)C)cc1]

Example 21

In a dried flask, morpholine (0.3 mL) and the product of Example 17 (0.25 g) were dissolved in pyridine (4 mL) and the mixture heated to 80° C. After 3 h, the reaction was quenched with saturated NH$_4$Cl (10 mL) and extracted with ethyl acetate. The residue was purified by column chromatography using methylene chloride as the eluent. Fractions containing the desired material were grouped and concentrated (0.1 g). NMR and Mass spectrum analysis of the solid indicated a structure that was consistent with 3-phenyl-3-(4-methoxyphenyl)-5-morpholino-7-fluoro-11-methoxy-13,13-dimethyl-3H,13H-indeno[2',3':3,4]naphtho[1,2-b]pyran represented by the following graphic formula:

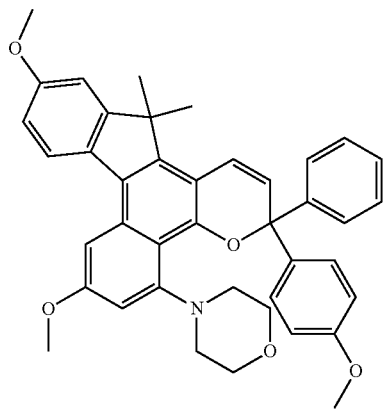 [SMILES: COc1ccc(C2(c3ccccc3)C=Cc3c4c(c5cc(OC)cc(N6CCOCC6)c5c3O2)-c2ccc(OC)cc2C4(C)C)cc1]

Example 22

The procedure from Example 19 was followed except that the product of Example 18 was used in place of the product of Example 17 to provide a solid product. NMR analysis indicated that the structure was consistent with 3-(4-butoxyphenyl)-3-(4-methoxyphenyl)-5-methoxy-7-fluoro-11-methoxy-13,13-dimethyl-3H,13H-indeno[2',3':3,4]naphtho[1,2-b]pyran represented by the following graphic formula:

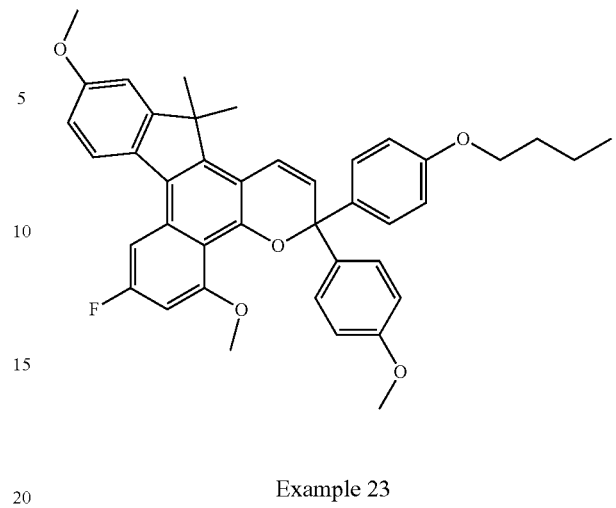

Example 23

Step 1

The product (6 g) from Step 2 of Example 16 was dissolved in methylene chloride (180 mL) and the solution cooled down in an ice bath. A solution of boron tribromide (BBr$_3$) (8 g) in methylene chloride (40 mL) was added dropwise. After 3.5 hours the reaction mixture was washed with water (400 mL) and the recovered organic solution was filtered through a silica plug [Using what element?]. After evaporation of the solvent the product (5.3 g) was collected. NMR analysis indicates the structure to be consistent with 2,4-difluoro-9-hydroxhy-7,7-dimethyl-7H-benzo[c]fluoren-5-ol.

Step 2

The product from Step 1 above (1.7 g) was dissolved in methylene chloride (50 mL) and 50 mg of p-toluensulfonic acid was added and stirred. A solution of 1-(4-methoxyphenyl)-1-phenyl-prop-2-yn-1-ol (1.2 g) in methylene chloride (70 mL) was added dropwise during a 3 hour time period. The reaction mixture was washed with water and the solvents evaporated. The product was purified by column chromatography using 1:1 hexanes methylene chloride mixtures as the eluent. Two products were collected: a less polar (0.6 g) and a more polar product (1.5 g). NMR analysis of the more polar product indicated a structure that was consistent with 3-(4-butoxyphenyl)-3-(4-methoxyphenyl)-5,7-difluoro-11-hydroxy-13,13-dimethyl-3H,13H-indeno[2',3':3,4]naphtho[1,2-b]pyran represented by the following graphic formula:

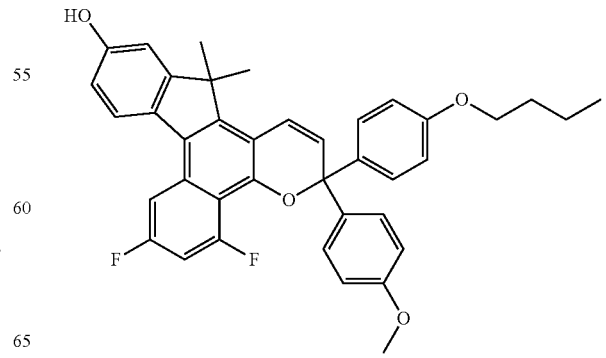

Example 24

Step 1

The product of Example 22 (1.5 g) and triethylamine (0.7 mL) were dissolved in methylene chloride (40 mL) and the mixture cooled in an ice bath. Triflic anhydride (0.4 mL) dissolved in methylene chloride (10 mL) was added in a 5 minutes period. After 5 minutes, the reaction mixture was passed through a silica gel plug and the product eluted using methylene chloride. The collected compound (1.5 g) was dissolved in ethanol (50 mL) and toluene (50 mL). Then $K_2CO_3$ (2.8 g) dissolved in water (50 mL) and 5-methylthiophene-2-boronic acid pinacol ester (0.53 mL) were added. The mixture was bubbled with nitrogen for 5 minutes and then PdCl2 2PPh3 (0.14 g) was added. The mixture was refluxed for 5 h and then extracted with ethyl acetate (150 mL). After evaporation of the solvents, the residue was purified by column chromatography using 6:1 hexanes ethyl acetate mixture as the eluent. NMR analysis indicated the structure of the product (0.7 g) to be consistent with 3-(4-butoxyphenyl)-3-(4-methoxyphenyl)-5,7-difluoro-11-(5-methythiophen-2-yl)-13,13-dimethyl-indeno[2',3':3,4]naphtho[1,2-b]pyran.

Step 2

The procedure from Example 19 was followed except that the product from Step 1 above was used in place of the product of Example 17 to provide a solid with an NMR analysis of the structure that is consistent with 3-(4-butoxyphenyl)-3-(4-methoxyphenyl)-5-methoxy-7-fluoro-11-(5-methythiophen-2-yl)-13,13-dimethyl-3H,13H-indeno[2',3':3,4]naphtho[1,2-b]pyran represented by the following graphic formula:

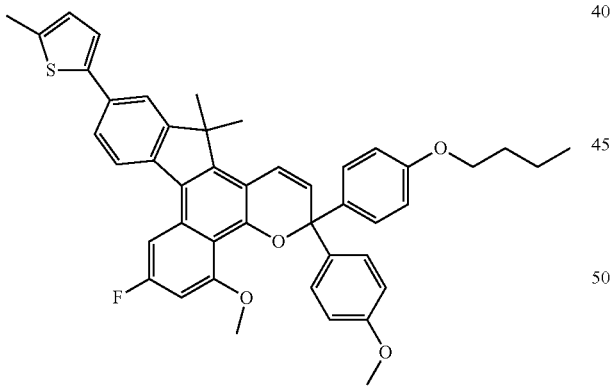

Example 25

The procedure from Step 2 of Example 23 was followed except that 1-phenyl-1-(4-methoxyphenyl)prop-2-yn-1-ol was used in place of 1-(4-butoxyphenyl)-1-(4-methoxyphenyl)prop-2-yn-1-ol. The NMR of the more polar product indicated a structure that was consistent with 3-phenyl-3-(4-methoxyphenyl)-5,7-difluoro-11-hydroxy-13,13-dimethyl-3H,13H-indeno[2',3':3,4]naphtho[1,2-b]pyran represented by the following graphic formula:

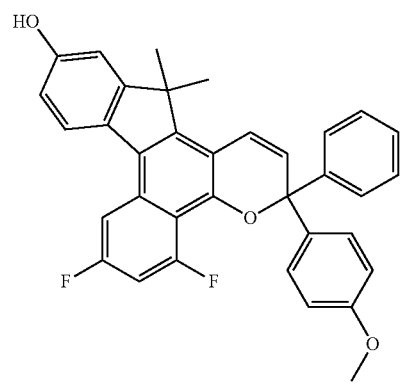 [SMILES: COc1ccc(C2(c3ccccc3)C=Cc3c4c(c5cc(F)cc(F)c5c3O2)-c2ccc(O)cc2C4(C)C)cc1]

Example 26

The procedure from Step 1 of Example 24 was followed except that the product of Example 25 was used in place of the product of Example 24 and phenyl boronic acid was used in place of methylthiophene-2-boronic acid pinacol ester to provide a solid product. NMR analysis of the product indicated a structure that was consistent with 3-phenyl-3-(4-methoxyphenyl)-5,7-difluoro-11-phenyl-13,13-dimethyl-3H,13H-indeno[2',3':3,4]naphtho[1,2-b]pyran represented by the following graphic formula:

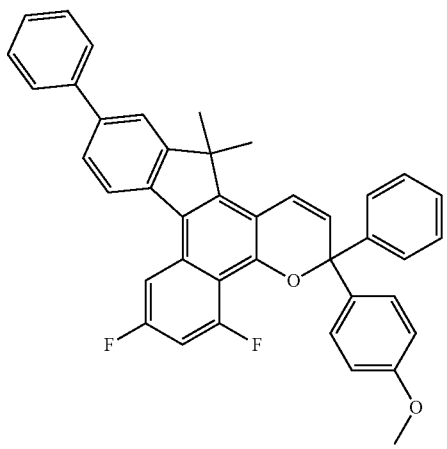 [SMILES: COc1ccc(C2(c3ccccc3)C=Cc3c4c(c5cc(F)cc(F)c5c3O2)-c2ccc(-c3ccccc3)cc2C4(C)C)cc1]

Comparative Example 1

CE-1

CE-1 was prepared following the disclosure of U.S. Pat. No. 5,645,767, which disclosure is incorporated herein by reference, and is reported to be 3,3-bis-(4-methoxyphenyl)-13,13-dimethyl-3H,13H-indeno[2',3':3,4]naphtho[1,2-b]pyran represented by the following graphic formula:

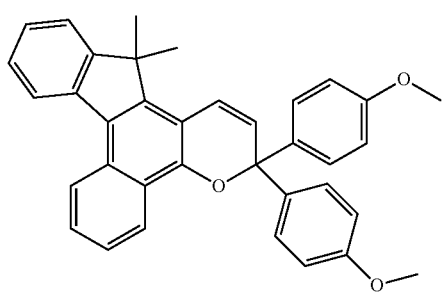 [SMILES: COc1ccc(C2(c3ccc(OC)cc3)C=Cc3c4c(c5ccccc5c3O2)-c2ccccc2C4(C)C)cc1]

Comparative Example 2

CE-2

Step 1

Maleic anhydride (36 g) was dissolved in cumene (300 mL) in a 3-necked flask (500 mL) equipped with condenser, followed by addition of tert-butyl peroxide (3-4 mL). The resulting mixture was heated to reflux and kept refluxing overnight. The solvent was removed under vacuum to provide a thick brown oil (75 g) containing 2-(2-phenylpropan-2-yl) succinic acid that was used for the next step without purification.

Step 2

The product of Step 1 (45 g) was dissolved in xylene (500 mL) in a 3-necked 1 L flask equipped with Dean-Stark Trap and condenser, followed by addition of dodecyl benzene sulphonic acid (5.9 g). The resulting mixture was heated to reflux and kept refluxing overnight. The solvent was removed under vacuum to provide a thick brown oil (49 g) that was used for the next step without purification.

Step 3

3-(2-Phenylpropan-2-yl)dihydrofuran-2,5-dione (29 g), was dissolved in dichloromethane (300 mL) in a 3-necked 1 L flask. The resulting mixture was cooled to 0-10° C. Anhydrous $AlCl_3$ (39 g) was added to the mixture slowly over 30 minutes. Three hours later, the reaction was quenched by pouring into icy water (200 mL) and acidifying with HCl (37%, 25 g). The product was extracted with ethyl acetate two times (2×100 mL). The recovered organic layers were combined, dried over anhydrous $MgSO_4$ and concentrated under vacuum to provide product (30 g). The product was purified by column chromatography using as the eluent, hexanes/EtOAc, 3/1, v/v yielding 16 g of the desired product. NMR analysis of the product indicated a structure that was consistent with 2-(1,1-dimethyl-3-oxo-2,3-dihydro-1H-inden-2-yl) acetic acid.

Step 4

The product of Step 3 (8 g), was dissolved in dry THF (100 mL) in a 3-necked 500 mL round bottom flask under nitrogen. The mixture was cooled to 0° C. Grignard reagent, 3-chlorophenyl magnesium bromide (1 M solution in diethyl ether, 200 mL), was added to the mixture slowly at 0-10° C. The addition was completed in 20 minutes and the reaction was stirred at room temperature for two hours. The reaction was worked up by pouring it into icy water (500 mL) and acidified with hydrochloric acid (37%, 25 g). The mixture was heated to 50-55° C. and stirred at that temperature for 1 h. The product was extracted with EtOAc twice (2×100 mL). The recovered organic layers were combined, dried over anhydrous $MgSO_4$ and concentrated under vacuum to provide product (23 g) that was used for the next step without purification.

Step 5

The product of Step 4 (23 g) was dissolved in acetic anhydride (300 mL) in a 3-necked 500 mL flask equipped with a condenser. The mixture was heated to reflux and kept refluxing for 8 hours. Solvent was removed to provide an oil (21 g) that contained 2-chloro-7,7-dimethyl-7H-benzo[c]fluoren-5-yl acetate that was used for the next step without purification.

Step 6

The product of Step 5 (21 g), was dissolved in methanol (100 mL) in a 3-necked 250 mL flask equipped with a condenser, followed by addition of HCl (37%, 2 mL). The mixture was heated to reflux and kept refluxing for one hour. Solvent was dried under vacuum to provide product (18 g) containing 2-chloro-7,7-dimethyl-7H-benzo[c]fluoren-5-ol.

Step 7

The product of Step 6 (4.8 g), was dissolved in dichloromethane (150 mL) in a 3-necked 100 mL round bottom flask, followed by addition of p-toluenesulfonic acid monohydrate (0.4 g). 1,1-Bis(4-methoxyphenyl)-2-propyn-1-ol (3.8 g) was added to the reaction mixture slowly. The mixture was stirred at room temperature. After one hour, more 1,1-bis (4-methoxyphenyl)-2-propyn-1-ol, (0.4 g) was added to the reaction mixture. After stirring for two hours, the reaction was worked up with the addition of saturated aqueous $NaHCO_3$ (100 mL). The resulting organic layer was collected and dried over anhydrous $MgSO_4$. The organic layer was concentrated under vacuum to provide product (8.7 g). The product was purified by column chromatography using silica gel and as eluent, a mixture of hexanes/EtOAc, (v/v, 4/1) to yield 2 g product. The product was foamed under vacuum and scratched with spatula to provide a solid material. The solid was slurried over methanol (30 mL), filtered and washed with methanol (2×20 mL) to provide a grayish product (1.4 g). NMR analysis of the product indicated a structure that was consistent with 3,3-bis-(4-methoxyphenyl)-7-chloro-13,13-dimethyl-3H,13H-indeno[2',3':3,4]naphtho[1,2-b]pyran represented by the following graphic formula:

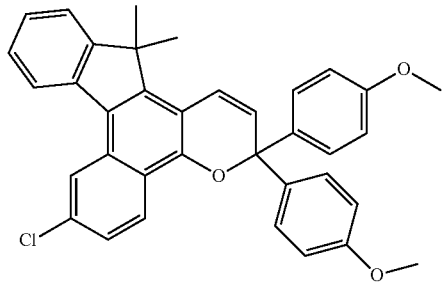 [SMILES: COc1ccc(C2(c3ccc(OC)cc3)C=Cc3c4c(c5cc(Cl)ccc5c3O2)-c2ccccc2C4(C)C)cc1]

Comparative Example 3

CE-3

CE-3 was prepared following the disclosure of Example 8 in U.S. application Ser. No. 13/313178 filed on Dec. 7, 2011, which disclosure is incorporated herein by reference, and is reported to be 3-(4-fluorophenyl)-3-(4-(piperidin-1-yl)phenyl)-10,12-dibromo-13,13-dimethyl-3H,13H-indeno[2',3':3,4]naphtho[1,2-b]pyran represented by the following graphic formula:

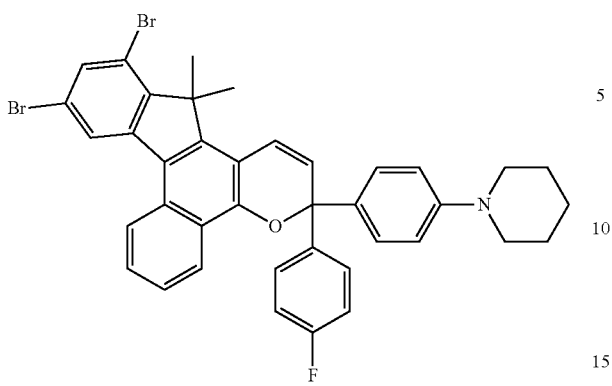

Comparative Example 4

CE-4

The procedure of Step 7 of Example 1 was followed except that the product of Step 6 of Example 5 was used in place of the product of Step 6 of Example 1 and the solvents methylene chloride and methanol were used for re-crystallization. NMR analysis indicated that the product had a structure consistent with 3,3-bis(4-methoxyphenyl)-6-methoxy-7-hydroxy-10,12-di(trifluoromethyl)-13,13-dimethyl-3H,13H-indeno[2',3':3,4]naphtho[1,2-b]pyran shown in the following graphic formula:

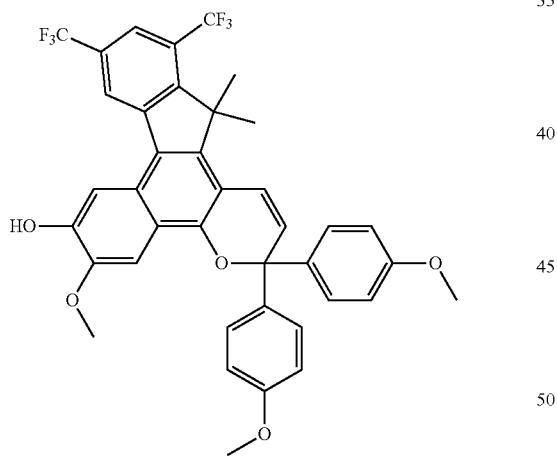

Comparative Example 5

CE-5

CE-5 was prepared following the disclosure of U.S. Pat. No. 5,645,767, which disclosure is incorporated herein by reference, and is reported to be 3-phenyl-3-(4-morpholinophenyl)-6,7-dimethoxy-13,13-dimethyl-3H,13H-indeno[2',3':3,4]naphtho[1,2-b]pyran represented by the following graphic formula:

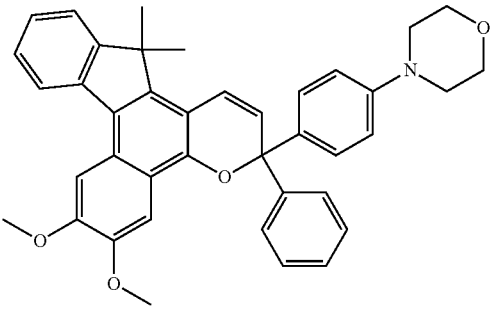 [SMILES: COc1cc2c3c(c4c(c2cc1OC)-c1ccccc1C4(C)C)C=CC(c1ccccc1)(c1ccc(N2CCOCC2)cc1)O3]

Comparative Example 6

CE-6

CE-6 was prepared following the disclosure of U.S. Patent Publication 2006/228,557A1, which disclosure is incorporated herein by reference, and is reported to be 3-(4-butoxyphenyl)-3-(4-morpholinophenyl)-11-phenyl-13,13-dimethyl-3H,13H-indeno[2,1-f]naphtho[1,2-b]pyran represented by the following graphic formula:

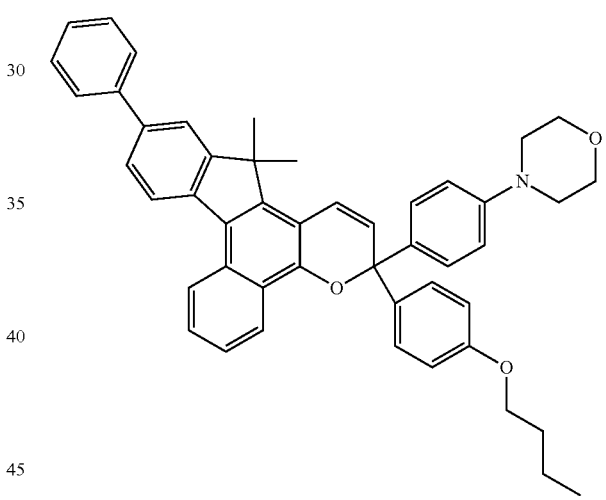

Comparative Example 7

CE-7

Step 1

To a reaction flask containing a pyridine (13 mL) solution of 7,7-dimethyl-7H-benzo[c]fluoren-5-ol (3.5 g, 13 mmol) was added a solution of trifluoromethanesulfonic anhydride (7.2 g, 26 mmol) in $CH_2Cl_2$ (10 mL) dropwise at 0° C. over a 15 min period. The reaction mixture was stirred at room temperature for 2 h. After removal of the solvent, the residue was poured into water and extracted with ether. The ether extract was evaporated to give product 5.28 g.

Step 2

Iodine monobromide (2.1 g) in glacial acetic acid (8 mL) was added into a reaction flask containing a solution of 3.37 g. of the product of Step 1 in 15 mL of glacial acetic acid which was kept cool in an ice-water bath. The reaction was allowed to stand for one hour during which time as much hydrogen bromide as possible was removed from the flask by gentle aeration. The mixture was poured into 2 wt % sodium bisulfite solution (50 mL). A saturated sodium bicarbonate suspension solution was then added and the solution was exacted with CH$_2$Cl$_2$. The product was obtained after the removal of solvent and was used directly in the next step.

Step 3

To a reaction flask containing the product obtained from Step 2 was added ethanol (25 mL) and NaOH (1.1 g, 26 mmol). The mixture was refluxed for 6 hours. Ethanol was removed by vacuum evaporation and then a saturated sodium bicarbonate suspension was then added and the resulting mixture was extracted with ethyl acetate. The recovered product (1.8 g) contained 7,7-dimethyl-9-bromo-7H-benzo[C]fluoren-5-ol and was used directly in the next step.

Step 4

The product of Step 3 (7.7 g)) and phenyl boronic acid (3.5 g) were added to a solution of dimethoxyethane (100 mL) and water (50 mL) in a 250 mL round bottom three-necked flask, followed by addition of Na$_2$CO$_3$ (5.1 g). The resulting solution was bubbled with nitrogen for 10 minutes and then the catalyst, tetrakis (triphenylphosphine) palladium (0.8 g), was added to the reaction mixture. The resulting reaction mixture was heated to reflux temperatures under a nitrogen atmosphere. The reaction was monitored by thin layer chromatography (TLC) analysis and by the end of the reaction; it was cooled to room temperature and quenched by adding water (30 mL). The pH of reaction mixture was adjusted to 5-6 by adding hydrochloric acid (37%, 9.5 g) slowly. The product was extracted with ethyl acetate (2×50 mL). The organic layers were recovered, combined, dried over anhydrous sodium sulfate, and concentrated by rotary evaporation to yield the product (11 g). The product was slurried over mixtures of hexanes and ethyl acetate (50 mL, hexanes/ethyl acetate, v/v, 9/1). The product was filtered off and washed with mixtures of hexanes and ethyl acetate (hexanes/ethyl acetate, v/v, 9/1) three times (3×20 mL) to provide yellowish solid containing 7,7-dimethyl-9-phenyl-7H-benzo[c]fluoren-5-ol (8 g).

Step 5

The product of Step 4 (2.0 g), was dissolved in dichloromethane (70 mL) in a 250 mL three-necked flask, followed by addition of p-toluenesulfonic acid (0.3 g). Then 1-(4-methoxyphenyl)-1-(4-butoxyphenyl)-2-propyn-1-ol (1.6 g) was added to the reaction mixture. The reaction was stirred at room temperature. Two hours later, trifluoroacetic acid (1 mL) was added to the reaction mixture. More, 1-(4-methoxyphenyl)-1-(4-butoxyphenyl)-2-propyn-1-ol (0.15 g), was added to the reaction mixture. The reaction was completed in another two hours. Saturated aqueous NaHCO$_3$ (20 mL) was added to the reaction mixture. It was stirred for 30 minutes. The product was extracted with dichloromethane (2×30 mL). The recovered organic layers were combined, dried over anhydrous MgSO$_4$, and concentrated under vacuum to provide the product (2.9 g). This material was purified by column chromatography (silica gel, 85% hexanes and 15% ethyl acetate as the eluant). The fractions containing product were combined, rotovaped, and dried under vacuum to provide a solid. The solid was then slurried over methanol (20 mL). The product was filtered off and washed with methanol (3×15 mL) to give product (2.3 g). An NMR spectrum showed that the structure was consistent with 3-(4-methoxyphenyl)-3-(4-butoxyphenyl)-11-phenyl-13,13-dimethyl-3H,13H-indeno[2',3':3,4]naphtho[1,2-b]pyran shown in the following graphic formula:

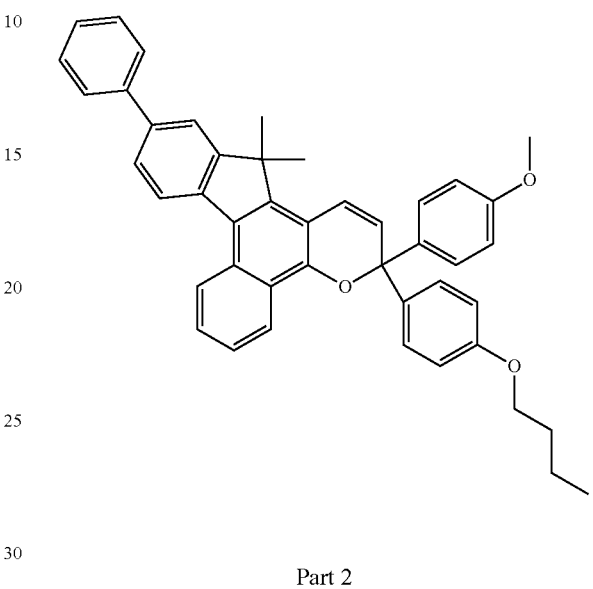

Part 2

Photochromic Property Testing

Part 2A—Test Square Preparation

Testing was done with the compounds described in Examples 1-22, 24 and 26 and CE 1-7 in the following manner. A quantity of compound calculated to yield a 1.5×10$^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis (2-methyl propionitrile) (AIBN). Each compound was dissolved into the monomer blend by stirring and gentle heating, if necessary. After a clear solution was obtained, the sample was degassed in a vacuum oven for 5-10 minutes at 25 torr. Using a syringe, the sample was poured into a flat sheet mold having an interior dimension of 2.2 mm+/−0.3 mm×6 inch (15.24 cm)×6 inch (15.24 cm). The mold was sealed and placed in a horizontal airflow, programmable oven to ramp from 40° C. to 95° C. over a 5 hour interval, hold the temperature at 95° C. for 3 hours, ramp down to 60° C. over a 2 hour interval and then hold at 60° C. for 16 hours. After curing, the mold was opened, and the polymer sheet was cut into 2 inch (5.1 cm) test squares using a diamond blade saw.

Part 2B—Response Testing

Prior to response testing on the optical bench, the photochromic test squares from Part 2A were exposed to 365 nm ultraviolet light for about 15 minutes to cause the photochromic material to transform from the ground state-form to an activated-state form, and then placed in a 75° C. oven for about 15 minutes to allow the photochromic material to revert back to the ground state-form. The test squares were then cooled to room temperature, exposed to fluorescent room lighting for at least 2 hours, and then covered (that is, in a dark environment) for at least 2 hours prior to testing on an optical bench maintained at 73° F. (23° C.). The optical bench fitted with a Schott 3 mm KG-2 band-pass filter, neutral density filter(s) and a Newport Model#67005 300-watt Xenon arc lamp with Model#69911 power supply in association with a Newport Model 689456 Digital Exposure/Timer was used to control the intensity of the irradiance beam utilized for activation of the sample. A Uniblitz model# CS25S3ZM0 with model# VMM-D3 controller) high-speed computer controlled shutter, a fused silica condensing lens for beam collimation of this activation lamp beam though a quartz glass water bath sample chamber.

A custom made broadband light source for monitoring response measurements was directed through the sample such that the angle between the activation source and the monitoring beam is 30 degrees with the sample positioned perpendicular to this monitoring beam. This broad beam light source is obtained by collecting and combining separately filtered light from a 100-Watt tungsten halogen lamp (controlled by a Lambda UP60-14 constant voltage powder supply) with a split-end, bifurcated fiber optical cable to enhance the short wavelength light intensity. After passing through the sample, this monitoring light was refocused into a 2-inch integrating sphere and fed to an Ocean Optics S2000 spectrophotometer by fiber optic cables. Ocean Optics SpectraSuite and PPG proprietary software were used to measure response and control the operation of the optical bench.

The $\lambda_{max\text{-}vis}$ is the wavelength in the visible spectrum at which the maximum absorption of the activated-state form of the photochromic compound in a test square occurs. The $\lambda_{max\text{-}vis}$ wavelength was determined by testing the photochromic test squares in a Varian Cary 4000 UV-Visible spectrophotometer.

The change in Optical density at saturation for each test sample was determined by opening the shutter from the xenon lamp and measuring the transmittance after exposing the test chip to 3 W/m2 UVA radiation for 30 minutes. The change in Optical density at saturation was calculated using the formula: $\Delta OD = \log(\% Tb/\% Ta)$, where % Tb is the percent transmittance in the bleached state, % Ta is the percent transmittance in the activated state both at the $\lambda_{max\text{-}vis}$ and the logarithm is to the base 10. The fade half life ("$T_{1/2}$") or bleach rate is the time interval in seconds for the absorbance of the activated-state form of the photochromic material in the test squares to reach one half the $\Delta OD$ at saturation value at room temperature (23° C.), after removal of the source of activating light. The Sensitivity ($\Delta OD/Min$) is a measure of how quickly the sample darkens and is calculated from the equation $\Delta OD_{sen} = \Delta OD_{5min} \times 12$.

The compounds of Examples 5 and 10 and Comparative Examples 4 and 5 exhibited dual peak absorptions in the visible spectrum (lambda max visible) in distinct color regions. For each lambda max visible, the corresponding optical density ($\Delta OD/Min$, and $\Delta OD$ at saturation) as well as fade half life are tabulated in Table 1 for the two bands (A and B) of peak absorption.

The results are listed in Table I. Comparative Examples 1 and 2 are similar in structure and should be compared to Examples 1 and 2. Comparative Examples 3 is similar in structure and should be compared to Example 4. Comparative Example 4 is similar in structure and should be compared to Example 5. Comparative Example 5 is similar in structure and should be compared to Example 10. Comparative Example 6 is similar in structure and should be compared to Example 12. Comparative Example 7 is similar in structure and should be compared to Example 13. In each comparison, the Example compound demonstrates a faster fade rate by a lower number of seconds and/or a darker coloration demonstrated by a higher number for Sensitivity and $\Delta OD$ at saturation value.

TABLE 1

Photochromic Performance Results

| Example # | $\lambda_{max\text{-}vis}$ (nm) | Sensitivity ($\Delta$ OD/Min) | $\Delta$ OD at saturation | $T^{1/2}$ (sec) |
|---|---|---|---|---|
| 1 | 563 | 0.69 | 0.53 | 46 |
| 2 | 559 | 0.77 | 0.61 | 50 |
| 3 | 560 | 0.54 | 0.26 | 22 |
| 4 | 603 | 0.33 | 0.18 | 28 |
| 5A | 441 | 0.63 | 0.48 | 61 |
| 5B | 532 | 0.83 | 0.67 | 62 |
| 6 | 519 | 0.78 | 0.97 | 135 |
| 7 | 533 | 0.79 | 0.69 | 64 |
| 8 | 527 | 0.50 | 0.18 | 14 |
| 9 | 526 | 0.44 | 0.17 | 15 |
| 10A | 471 | 0.43 | 1.30 | 514 |
| 10B | 558 | 0.68 | 2.23 | 429 |
| 11 | 561 | 0.68 | 0.80 | 96 |
| 12 | 571 | 0.91 | 2.06 | 459 |
| 13 | 546 | 0.99 | 2.16 | 608 |
| 14 | 566 | 0.52 | 0.65 | 92 |
| 15 | 572 | 0.67 | 0.97 | 175 |
| 16 | 546 | 0.61 | 1.42 | 498 |
| 17 | 558 | 0.74 | 1.42 | 275 |
| 18 | 572 | 0.71 | 0.93 | 105 |
| 19 | 542 | 0.70 | 2.05 | 1755 |
| 20 | 523 | 0.73 | 1.54 | >2000 |
| 21 | 541 | 0.71 | 1.28 | 491 |
| 22 | 551 | 0.53 | 1.29 | 696 |
| 23 | — | — | — | — |
| 24 | 556 | 0.91 | 1.49 | 454 |
| 25 | — | — | — | — |
| 26 | 552 | 0.73 | 1.11 | 164 |
| CE-1 | 558 | 0.67 | 0.86 | 121 |
| CE-2 | 561 | 0.59 | 0.55 | 61 |
| CE-3 | 608 | 0.41 | 0.29 | 37 |
| CE-4A | 457 | 0.45 | 0.46 | 60 |
| CE-4B | 572 | 0.26 | 0.28 | 60 |
| CE-5A | 484 | 0.40 | 1.24 | 471 |
| CE-5B | 594 | 0.38 | 1.16 | 470 |
| CE-6 | 598 | 0.56 | 0.69 | 103 |
| CE-7 | 572 | 0.62 | 0.83 | 134 |

The present invention has been described with reference to specific details of particular embodiments thereof. It is not intended that such details be regarded as limitations upon the scope of the invention except insofar as to the extent that they are included in the accompanying claims.

We claim:

1. A compound of Formula III:

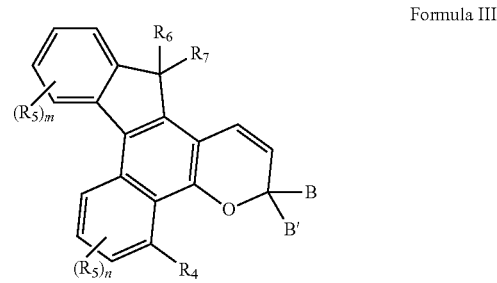

Formula III wherein $R_4$ is selected from hydroxy, halogen, optionally substituted alkyl, optionally substituted alkenyl, optionally substituted alkynyl, optionally substituted aryl, optionally substituted heteroaryl, optionally substituted alkoxy, cyano, nitro, alkoxycarbonyl, aminocarbonyl, carboxy, optionally substituted amino, carbamidyl, ureido, thioureido, silyl, —SH, siloxy, sulfanyl, and azido;

R₅ for each occurrence, is independently selected from chiral or achiral groups selected from formyl, alkyl carbonyl, alkoxycarbonyl, aminocarbonyl, arylcarbonyl, aryloxycarbonyl, aminocarbonyloxy, alkoxycarbonylamino, aryloxycarbonylamino, boronic acid, boronic acid esters, cycloalkoxycarbonylamino, heterocycloalkyloxycarbonylamino, heteroaryloxycarbonylamino, optionally substituted alkenyl, optionally substituted alkynyl, halogen, optionally substituted aryl, optionally substituted heteroaryl, optionally substituted heteroalkyl, and optionally substituted heterocycloalkyl;

m is an integer from 0 to 4;

n is an integer from 0 to 3;

R₆ and R₇ are each independently selected from hydrogen, hydroxy and chiral or achiral groups selected from optionally substituted heteroalkyl, optionally substituted alkyl, optionally substituted alkenyl, optionally substituted alkynyl, optionally substituted aryl, optionally substituted heteroaryl, optionally substituted cycloalkyl, optionally substituted heterocycloalkyl, halogen, optionally substituted amino, carboxy, alkylcarbonyl, alkoxycarbonyl, optionally substituted alkoxy, and aminocarbonyl, or R₆ and R₇ may be taken together with any intervening atoms to form a group selected from oxo, optionally substituted cycloalkyl, and optionally substituted heterocycloalkyl; and B and B' are each independently selected from hydrogen, halogen, and chiral or achiral groups selected from metallocenyl, optionally substituted alkyl, optionally substituted alkenyl, optionally substituted alkynyl, optionally substituted heteroalkyl, optionally substituted alkoxy, optionally substituted aryl, optionally substituted heteroaryl, optionally substituted heterocycloalkyl, and optionally substituted cycloalkyl, or wherein B and B' are taken together with any intervening atoms to form a group selected from optionally substituted cycloalkyl and optionally substituted heterocycloalkyl.

2. The compound of claim 1, wherein R₄ is selected from chloro, fluoro, bromo, methyl, ethyl, phenyl, perflouroalkoxy, and perfluoroalkyl R₅ for each occurrence, is independently selected from alkylcarbonyl, alkoxycarbonyl, aminocarbonyl, boronic acid ester, halogen, optionally substituted aryl, and optionally substituted heterocycloalkyl;

m and n are each independently an integer selected from 0 to 2;

R₆ and R₇ are each independently selected from hydrogen, hydroxy, and chiral groups selected from optionally substituted heteroalkyl, optionally substituted alkyl, optionally substituted aryl, optionally substituted cycloalkyl, halogen, carboxy, alkylcarbonyl, alkoxycarbonyl, optionally substituted alkoxy, and aminocarbonyl or R₆ and R₇ may be taken together with any intervening atoms to form a group selected from oxo and optionally substituted cycloalkyl; and B and B' are each independently selected from hydrogen, chiral groups selected from optionally substituted alkyl, optionally substituted alkenyl, optionally substituted aryl, optionally substituted heteroaryl, and optionally substituted cycloalkyl, or B and B' are taken together with any intervening atoms to form a group selected from optionally substituted cycloalkyl.

3. The compound of claim 2, wherein R₄ is selected from chloro, fluoro, bromo, and trifluoromethyl;

R₅ for each occurrence is independently selected from bromo, chloro, fluoro, and CF₃;

R₆ and R₇ are each independently selected from methyl, ethyl, propyl and butyl; and B and B' are each independently selected from phenyl substituted with one or more groups independently selected from aryl, heteroaryl, heterocycloalkyl, alkyl, alkenyl, alkynyl, alkoxy, halogen, amino, alkylcarbonyl, carboxy, and alkoxycarbonyl.

4. The compound of claim 1, selected from:
3,3-bis(4-methoxyphenyl)-5,7-dibromo-13,13-dimethyl-3H,13H-indeno[2',3':3,4]naphtho[1,2-b]pyran;
3,3-bis(4-methoxyphenyl)-5,7-dichloro-13,13-dimethyl-3H,13H-indeno[2',3':3,4]naphtho[1,2-b]pyran;
3-(4-butoxyphenyl)-3-(4-methoxyphenyl)-5,7-dibromo-11-trifluromethyl-13,13-dimethyl-3H,13H-indeno[2',3':3,4]naphtho[1,2-b]pyran;
3-(4-fluorophenyl)-3-(4-(N-piperidinyl)phenyl)5,7-difluoro-10,12-dibromo-13,13-dimethyl-3H,13H-indeno[2',3':3,4]naphtho[1,2-b]pyran;
3,3-bis(4-fluorophenyl)-5,7-di(trifluoromethyl)-12-bromo-13,13-dimethyl-3H,13H-indeno[2',3':3,4]naphtho[1,2-b]pyran;
3,3-bis(4-fluorophenyl)-5,7-di(trifluoromethyl)-10-bromo-13,13-dimethyl-3H,13H-indeno[2',3':3,4]naphtho[1,2-b]pyran
3-(4-methoxyphenyl)-3-(4-morpholinophenyl)-5-methoxy-11-phenyl-13,13-dimethyl-3H,13H-indeno[2,1-f]naphtho[1,2-b]pyran;
3,3-bis(4-methoxyphenyl)-5-methoxy-11-phenyl-13,13-dimethyl-3H,13H-indeno[2',3':3,4]naphtho[1,2-b]pyran;
3-(4-butoxyphenyl)-3-(4-methoxyphenyl)-5-methoxy-7-fluoro-11-(5-methythiophen-2-yl)-13,13-dimethyl-3H,13H-indeno[2',3':3,4]naphtho[1,2-b]pyran;
and
3-phenyl-3-(4-methoxyphenyl)-5,7-difluoro-11-phenyl-13,13-dimethyl-3H,13H-indeno[2',3':3,4]naphtho[1,2-b]pyran.

5. A photochromic composition comprising the compound of claim 1 and optionally at least one other photochromic compound, wherein said composition comprises:
(a) a single photochromic compound;
(b) a mixture of photochromic compounds;
(c) a material comprising at least one photochromic compound;
(d) a material to which at least one photochromic compound is chemically bonded;
(e) material (c) or (d) further comprising a coating to substantially prevent contact of the at least one photochromic compound with external materials;
(f) a photochromic polymer; or
(g) mixtures thereof.

6. A photochromic composition comprising at least one compound of claim 1 incorporated into at least a portion of an organic material, said organic material being a polymeric material, an oligomeric material, a monomeric material or a mixture or combination thereof.

7. The photochromic composition of claim 6 wherein said polymeric material comprises liquid crystal materials, self-assembling materials, polycarbonate, polyamide, polyimide, poly(meth)acrylate, polycyclic alkene, polyurethane, poly(urea)urethane, polythiourethane, polythio(urea)urethane, polyol(allyl carbonate), cellulose acetate, cellulose diacetate, cellulose triacetate, cellulose acetate propionate, cellulose acetate butyrate, polyalkene, polyalkylene-vinyl acetate, poly(vinylacetate), poly(vinyl alcohol), poly(vinyl chloride), poly (vinylformal), poly(vinylacetal), poly(vinylidene chloride), poly(ethylene terephthalate), polyester, polysulfone, polyolefin, copolymers thereof, and/or mixtures thereof.

8. The photochromic composition of claim 6 wherein the photochromic composition further comprises at least one additive chosen from dyes, alignment promoters, antioxidants, kinetic enhancing additives, photoinitiators, thermal initiators, polymerization inhibitors, solvents, light stabilizers, heat stabilizers, mold release agents, rheology control agents, leveling agents, free radical scavengers, gelators and adhesion promoters.

9. The photochromic composition of claim 8 comprising a coating composition comprising a material chosen from liquid crystal materials, self-assembling materials and film forming materials.

10. A photochromic article comprising a substrate and said compound according to claim 1 connected to at least a portion of a substrate.

11. The photochromic article of claim 10 comprising an optical element, said optical element being at least one of an ophthalmic element, a display element, a window, a mirror, packaging material and an active or passive liquid crystal cell element.

12. The photochromic article of claim 11, wherein the ophthalmic element comprises corrective lenses, non-corrective lenses, contact lenses, intra-ocular lenses, magnifying lenses, protective lenses, or visors.

13. The photochromic article of claim 12 wherein the substrate comprises a polymeric material and the photochromic material is incorporated into at least a portion of the polymeric material.

14. The photochromic article of claim 13 wherein the photochromic material is blended with at least a portion of the polymeric material, bonded to at least a portion of the polymeric material, and/or imbibed into at least a portion of the polymeric material.

15. The photochromic article of claim 10 wherein the photochromic article comprises a coating or film connected to at least a portion of the substrate, said coating or film comprising the photochromic material.

16. The photochromic article of claim 15 wherein said substrate is formed from organic materials, inorganic materials, or combinations thereof.

17. The photochromic article of claim 15 further comprising at least one additional at least partial coating chosen from photochromic coatings, anti-reflective coatings, linearly polarizing coatings, transitional coatings, primer coatings, adhesive coatings, reflective coatings, antifogging coatings, oxygen barrier coatings, ultraviolet light absorbing coatings, and protective coatings.

18. A photochromic article comprising
a substrate;
at least a partial coating of one alignment material;
at least one additional at least partial coating of a liquid crystal material; and
at least one compound of claim 1.

19. The photochromic article of claim 18 further comprising at least one additive chosen from dichroic dyes, non-dichroic dyes, alignment promoters, antioxidants, kinetic enhancing additives, photoinitiators, thermal initiators, polymerization inhibitors, solvents, light stabilizers, heat stabilizers, mold release agents, rheology control agents, leveling agents, free radical scavengers, gelators and adhesion promoters.

20. The photochromic article of claim 18, wherein the substrate is selected from glass, quartz, and polymeric organic materials.

21. The photochromic article of claim 18, wherein the at least one alignment material comprises a polymer network orientable by exposure to at least one of: a magnetic field, an electric field, linearly polarized infrared radiation, linearly polarized ultraviolet radiation, linearly polarized visible radiation and a shear force.

22. The photochromic article of claim 18, wherein said liquid crystal material is a liquid crystal polymer.

23. The photochromic article of claim 18, further comprising at least one primer coating, transitional coating, protective coating or a combination thereof.

24. The photochromic article of claim 23, wherein the transitional coating comprises an acrylate polymer.

25. The photochromic article of claim 23, wherein the protective coating comprises at least one siloxane derivative.

26. The photochromic article of claim 25, wherein the at least one primer coating comprises a polyurethane.

* * * * *

UNITED STATES PATENT AND TRADEMARK OFFICE
CERTIFICATE OF CORRECTION

PATENT NO. : 8,920,928 B2  
APPLICATION NO. : 13/325285  
DATED : December 30, 2014  
INVENTOR(S) : Meng He et al.

Page 1 of 1

It is certified that error appears in the above-identified patent and that said Letters Patent is hereby corrected as shown below:

On the Title Page of the Patent, Column 2, Item (56) OTHER PUBLICATIONS, Line 1, delete ""Photochronnism,"" and insert -- "Photochromism," --

In the Claims

Column 67, Lines 2-3, Claim 1, delete "alkyl carbonyl," and insert -- alkylcarbonyl, --

Column 67, Line 42, Claim 2, delete "perflouroalkoxy," and insert -- perfluoroalkoxy, --

Column 68, Line 16, Claim 4, delete "-trifluromethyl-" and insert -- -trifluoromethyl- --

Column 68, Line 26, Claim 4, delete "pyran" and insert -- pyran; --

Signed and Sealed this  
Twelfth Day of May, 2015

Michelle K. Lee  
*Director of the United States Patent and Trademark Office*